US011911258B2

(12) United States Patent
Center et al.

(10) Patent No.: US 11,911,258 B2
(45) Date of Patent: Feb. 27, 2024

(54) SPACE FILLING DEVICES

(71) Applicant: W. L. Gore & Associates, Inc., Newark, DE (US)

(72) Inventors: Charles J. Center, Flagstaff, AZ (US); Edward H. Cully, Flagstaff, AZ (US); Nathan L. Friedman, Flagstaff, AZ (US); Cody L. Hartman, Flagstaff, AZ (US); Nichlas L. Helder, Flagstaff, AZ (US); Brandon A. Lurie, Flagstaff, AZ (US); Steven J. Masters, Flagstaff, AZ (US); Thomas R. McDaniel, Flagstaff, AZ (US); Nathan K. Mooney, Elkton, MD (US); Aaron L. Paris, Flagstaff, AZ (US); Roark N. Wolfe, Flagstaff, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 766 days.

(21) Appl. No.: 14/315,246

(22) Filed: Jun. 25, 2014

(65) Prior Publication Data
US 2015/0005810 A1   Jan. 1, 2015

Related U.S. Application Data

(60) Provisional application No. 61/839,824, filed on Jun. 26, 2013, provisional application No. 61/907,326, filed on Nov. 21, 2013.

(51) Int. Cl.
*A61F 2/01* (2006.01)
*A61B 17/00* (2006.01)
*A61B 17/12* (2006.01)

(52) U.S. Cl.
CPC ............ *A61F 2/01* (2013.01); *A61B 17/0057* (2013.01); *A61B 17/12109* (2013.01);
(Continued)

(58) Field of Classification Search
CPC ............... A61F 2/01; A61F 2002/9511; A61B 17/12109; A61B 17/12113;
(Continued)

(56) References Cited

U.S. PATENT DOCUMENTS

| 654,799 A | 7/1900 | Levett |
| 1,851,314 A | 3/1932 | Knoche |

(Continued)

FOREIGN PATENT DOCUMENTS

| CN | 1342056 A | 3/2002 |
| CN | 2820130 Y | 9/2006 |

(Continued)

OTHER PUBLICATIONS

International Search Report for PCT/US2014/044258 dated Oct. 29, 2014, corresponding to U.S. Appl. No. 14/315,246, p. 4.
(Continued)

*Primary Examiner* — Sarah W Aleman
*Assistant Examiner* — Rachel S Highland
(74) *Attorney, Agent, or Firm* — GREENBERG TRAURIG, LLP

(57) ABSTRACT

An occlusive device includes a covering component configured to modulate passage of blood or thrombus therethrough, and an occlusion frame that includes a plurality of elongate occlusion frame members. The elongate occlusion frame members are arranged to form a generally disc-shaped member. The occlusion frame is at least partially covered by the covering component. The device further includes an anchor frame that includes a plurality of elongate anchor frame members. The device further includes a first hub component from which the elongate frame members extend, and a second hub component from which the elongate frame members extend.

14 Claims, 53 Drawing Sheets

(52) U.S. Cl.
CPC .. *A61B 17/12113* (2013.01); *A61B 17/12122* (2013.01); *A61B 17/12172* (2013.01); *A61B 17/12177* (2013.01); *A61B 2017/00592* (2013.01); *A61B 2017/00597* (2013.01); *A61B 2017/00606* (2013.01); *A61B 2017/00615* (2013.01); *A61B 2017/00628* (2013.01); *A61B 2017/00641* (2013.01); *A61B 2017/00986* (2013.01); *A61F 2002/016* (2013.01)

(58) Field of Classification Search
CPC ........ A61B 17/12122; A61B 17/12177; A61B 17/12172; A61B 17/0057; A61B 2017/00986; A61B 2017/00641; A61B 2017/00628; A61B 2017/00592; A61B 2017/00597; A61B 2017/00606; A61B 2017/00

See application file for complete search history.

(56) References Cited

U.S. PATENT DOCUMENTS

| | | |
|---|---|---|
| 3,625,451 A | 12/1971 | Anderson |
| 3,915,167 A | 10/1975 | Waterman |
| 3,953,566 A | 4/1976 | Gore |
| 4,222,126 A | 9/1980 | Boretos et al. |
| 4,265,694 A | 5/1981 | Boretos et al. |
| 4,339,831 A | 7/1982 | Johnson |
| 4,340,091 A | 7/1982 | Skelton et al. |
| 4,349,498 A | 9/1982 | Ellis et al. |
| 4,425,908 A | 1/1984 | Simon |
| 4,626,255 A | 12/1986 | Reichart et al. |
| 4,629,459 A | 12/1986 | Ionescu et al. |
| 4,655,246 A | 4/1987 | Philipot et al. |
| 4,692,369 A | 9/1987 | Nomi |
| 4,731,074 A | 3/1988 | Rousseau et al. |
| 4,851,000 A | 7/1989 | Gupta |
| 4,858,810 A | 8/1989 | Intlekofer |
| 4,877,661 A | 10/1989 | House et al. |
| 4,955,899 A | 9/1990 | Della et al. |
| 5,026,513 A | 6/1991 | House et al. |
| 5,071,609 A | 12/1991 | Tu et al. |
| 5,217,486 A | 6/1993 | Rice et al. |
| 5,325,746 A | 7/1994 | Anderson |
| 5,344,427 A | 9/1994 | Cottenceau et al. |
| 5,397,355 A | 3/1995 | Marin |
| 5,476,589 A | 12/1995 | Bacino |
| 5,527,338 A | 6/1996 | Purdy |
| 5,534,007 A | 7/1996 | St et al. |
| 5,549,663 A | 8/1996 | Cottone, Jr. |
| 5,554,183 A | 9/1996 | Nazari |
| 5,562,726 A | 10/1996 | Chuter |
| 5,693,083 A | 12/1997 | Baker et al. |
| 5,707,376 A | 1/1998 | Kavteladze et al. |
| 5,708,044 A | 1/1998 | Branca |
| 5,709,704 A | 1/1998 | Nott et al. |
| 5,713,917 A | 2/1998 | Leonhardt et al. |
| 5,713,948 A | 2/1998 | Ulfacker |
| 5,718,973 A | 2/1998 | Lewis et al. |
| 5,720,776 A | 2/1998 | Chuter et al. |
| 5,725,552 A | 3/1998 | Kotula |
| 5,759,192 A | 6/1998 | Saunders |
| 5,769,884 A | 6/1998 | Solovay |
| 5,772,884 A | 6/1998 | Tanaka et al. |
| 5,776,141 A | 7/1998 | Klein et al. |
| 5,776,186 A | 7/1998 | Uflacker |
| 5,782,909 A | 7/1998 | Quiachon et al. |
| 5,824,043 A | 10/1998 | Cottone, Jr. |
| 5,824,050 A | 10/1998 | Karwoski et al. |
| 5,843,158 A | 12/1998 | Lenker et al. |
| 5,843,161 A | 12/1998 | Solovay |
| 5,843,162 A | 12/1998 | Inoue |
| 5,904,703 A | 5/1999 | Gilson |
| 5,935,162 A | 8/1999 | Dang |
| 5,961,546 A | 10/1999 | Robinson et al. |
| 6,010,529 A | 1/2000 | Herweck et al. |
| 6,013,093 A | 1/2000 | Nott et al. |
| 6,013,854 A | 1/2000 | Moriuchi |
| 6,015,431 A | 1/2000 | Thornton et al. |
| 6,019,785 A | 2/2000 | Strecker |
| 6,027,779 A | 2/2000 | Campbell et al. |
| 6,042,588 A | 3/2000 | Munsinger et al. |
| 6,042,606 A | 3/2000 | Frantzen |
| 6,143,021 A | 11/2000 | Staeghle |
| 6,152,144 A | 11/2000 | Lesh |
| 6,165,195 A | 12/2000 | Wilson |
| 6,174,331 B1 | 1/2001 | Moe et al. |
| 6,190,406 B1 | 2/2001 | Duerig et al. |
| 6,214,025 B1 | 4/2001 | Thistle et al. |
| 6,231,561 B1 | 5/2001 | Frazier et al. |
| 6,231,581 B1 | 5/2001 | Shank et al. |
| 6,231,589 B1 | 5/2001 | Wessman et al. |
| 6,245,012 B1 | 6/2001 | Kleshinski |
| 6,245,939 B1 | 6/2001 | Hsu et al. |
| 6,261,320 B1 | 7/2001 | Tam et al. |
| 6,264,671 B1 | 7/2001 | Stack |
| 6,273,900 B1 | 8/2001 | Nott et al. |
| 6,283,994 B1 | 9/2001 | Moe et al. |
| 6,322,585 B1 | 11/2001 | Khosravi et al. |
| 6,328,727 B1 | 12/2001 | Frazier et al. |
| 6,346,117 B1 | 2/2002 | Greenhalgh |
| 6,352,561 B1 | 3/2002 | Leopold et al. |
| 6,372,870 B1 | 4/2002 | Kitahara et al. |
| 6,436,132 B1 | 8/2002 | Patel et al. |
| 6,451,051 B2 | 9/2002 | Drasler et al. |
| 6,451,396 B1 | 9/2002 | Zumbrum et al. |
| 6,485,513 B1 | 11/2002 | Fan |
| 6,488,701 B1 | 12/2002 | Nolting et al. |
| 6,491,704 B2 | 12/2002 | Gifford et al. |
| 6,524,335 B1 | 2/2003 | Hartley et al. |
| 6,527,779 B1 | 3/2003 | Rourke |
| 6,541,589 B1 | 4/2003 | Baillie |
| 6,551,303 B1 | 4/2003 | Tessel et al. |
| 6,551,350 B1 | 4/2003 | Thornton et al. |
| 6,562,069 B2 | 5/2003 | Cai et al. |
| 6,572,643 B1 | 6/2003 | Gharibadeh |
| 6,572,646 B1 | 6/2003 | Boylan et al. |
| 6,620,190 B1 | 9/2003 | Colone |
| 6,626,939 B1 | 9/2003 | Burnside et al. |
| 6,652,556 B1 * | 11/2003 | VanTassel ........ A61B 17/12159 606/200 |
| 6,666,885 B2 | 12/2003 | Moe |
| 6,673,455 B2 | 1/2004 | Zumbrum et al. |
| 6,689,150 B1 | 2/2004 | Van Tassel |
| 6,705,563 B2 | 3/2004 | Luo et al. |
| 6,712,836 B1 | 3/2004 | Berg et al. |
| 6,712,842 B1 | 3/2004 | Gifford, III et al. |
| 6,726,715 B2 | 4/2004 | Sutherland |
| 6,730,108 B2 | 5/2004 | Van Tassel |
| 6,730,120 B2 | 5/2004 | Berg et al. |
| 6,743,210 B2 | 6/2004 | Hart et al. |
| 6,746,472 B2 | 6/2004 | Frazier et al. |
| 6,755,854 B2 | 6/2004 | Gillick et al. |
| 6,755,856 B2 | 6/2004 | Fierens et al. |
| 6,755,857 B2 | 6/2004 | Peterson et al. |
| 6,758,858 B2 | 7/2004 | McCrea et al. |
| 6,770,579 B1 | 8/2004 | Dawson et al. |
| 6,776,604 B1 | 8/2004 | Chobotov et al. |
| 6,827,731 B2 | 12/2004 | Armstrong et al. |
| 6,866,669 B2 | 3/2005 | Buzzard et al. |
| 6,884,259 B2 | 4/2005 | Tran et al. |
| 6,926,732 B2 | 8/2005 | Derus et al. |
| 6,939,352 B2 | 9/2005 | Buzzard et al. |
| 6,945,990 B2 | 9/2005 | Greenan |
| 6,949,113 B2 | 9/2005 | Van Tassel |
| 6,953,332 B1 | 10/2005 | Kurk et al. |
| 6,974,471 B2 | 12/2005 | Van Shie et al. |
| 6,994,092 B2 | 2/2006 | Van Der Burg et al. |
| 7,033,368 B2 | 4/2006 | Rourke |
| 7,044,134 B2 | 5/2006 | Khairkhahan |
| 7,049,380 B1 | 5/2006 | Chang |
| 7,052,511 B2 | 5/2006 | Weldon et al. |
| 7,066,951 B2 | 6/2006 | Chovotov |
| 7,083,642 B2 | 8/2006 | Sirhan et al. |

(56) References Cited

U.S. PATENT DOCUMENTS

| | | |
|---|---|---|
| 7,105,018 B1 | 9/2006 | Yip et al. |
| 7,122,050 B2 | 10/2006 | Randall et al. |
| 7,128,073 B1 | 10/2006 | Van Der Burg et al. |
| 7,147,657 B2 | 12/2006 | Chiang et al. |
| 7,169,160 B1 | 1/2007 | Middleman et al. |
| 7,198,636 B2 | 4/2007 | Cully et al. |
| 7,208,003 B2 | 4/2007 | Davis et al. |
| 7,238,200 B2 | 7/2007 | Lee et al. |
| 7,252,680 B2 | 8/2007 | Freitag |
| 7,306,729 B2 | 12/2007 | Bacino et al. |
| 7,331,992 B2 | 2/2008 | Randall et al. |
| 7,396,359 B1 | 7/2008 | DeRowe |
| 7,419,678 B2 | 9/2008 | Falotico |
| 7,448,122 B1 | 11/2008 | Kokish et al. |
| 7,462,675 B2 | 12/2008 | Chang et al. |
| 7,531,611 B2 | 5/2009 | Sabol et al. |
| 7,566,336 B2 * | 7/2009 | Corcoran .......... A61B 17/0057 606/151 |
| 7,572,289 B2 | 8/2009 | Sisken et al. |
| 7,601,159 B2 | 10/2009 | Ewers et al. |
| 7,611,528 B2 | 11/2009 | Goodson et al. |
| 7,628,803 B2 | 12/2009 | Pavcnik et al. |
| 7,655,034 B2 | 2/2010 | Mitchell et al. |
| 7,678,123 B2 | 3/2010 | Chanduszko |
| 7,771,455 B2 | 8/2010 | Ken |
| 7,789,908 B2 | 9/2010 | Sowinski et al. |
| 7,803,186 B1 | 9/2010 | Li et al. |
| 7,811,314 B2 | 10/2010 | Fierens et al. |
| 7,815,591 B2 | 10/2010 | Levine et al. |
| 7,815,763 B2 | 10/2010 | Fierens et al. |
| 7,833,565 B2 | 11/2010 | O'Connor et al. |
| 7,846,179 B2 | 12/2010 | Belef et al. |
| 7,887,580 B2 | 2/2011 | Randall et al. |
| 7,927,364 B2 | 4/2011 | Fierens et al. |
| 7,927,365 B2 | 4/2011 | Fierens et al. |
| 7,935,141 B2 | 5/2011 | Randall et al. |
| 7,967,829 B2 | 6/2011 | Gunderson et al. |
| 7,976,575 B2 | 7/2011 | Hartley |
| 7,998,189 B2 | 8/2011 | Kolbel et al. |
| 8,029,557 B2 | 10/2011 | Sobrino-Serrano et al. |
| 8,029,559 B2 | 10/2011 | Sisken et al. |
| 8,029,563 B2 | 10/2011 | House et al. |
| 8,048,440 B2 | 11/2011 | Chang |
| 8,062,349 B2 | 11/2011 | Moore et al. |
| 8,080,032 B2 | 12/2011 | van der Burg |
| 8,157,810 B2 | 4/2012 | Case et al. |
| 8,167,935 B2 | 5/2012 | McGuckin et al. |
| 8,231,650 B2 | 7/2012 | Cully |
| 8,241,350 B2 | 8/2012 | Randall et al. |
| 8,273,105 B2 | 9/2012 | Cohen et al. |
| 8,287,583 B2 | 10/2012 | LaDuca et al. |
| 8,349,000 B2 | 1/2013 | Schreck |
| 8,424,166 B2 | 4/2013 | Dorneman et al. |
| 8,449,595 B2 | 5/2013 | Ouellette et al. |
| 8,469,990 B2 | 6/2013 | McGuckin |
| 8,475,512 B2 | 7/2013 | Hunt |
| 8,523,897 B2 | 9/2013 | van der Burg |
| 8,529,597 B2 | 9/2013 | Linder |
| 8,585,757 B2 | 11/2013 | Agathos |
| 8,637,144 B2 | 1/2014 | Ford |
| 8,685,055 B2 | 4/2014 | Van Tassel |
| 8,709,077 B2 | 4/2014 | Schreck |
| 8,801,746 B1 | 8/2014 | Kreidler |
| 8,834,519 B2 | 9/2014 | van der Burg |
| 8,870,947 B2 | 10/2014 | Shaw |
| 8,945,212 B2 | 2/2015 | Bruchman et al. |
| 8,961,599 B2 | 2/2015 | Bruchman et al. |
| 9,109,310 B2 | 8/2015 | Baaijens et al. |
| 9,254,204 B2 | 2/2016 | Roeder |
| 9,314,249 B2 | 4/2016 | Kreidler |
| 9,504,565 B2 | 11/2016 | Armstrong |
| 9,554,806 B2 | 1/2017 | Larsen et al. |
| 9,554,900 B2 | 1/2017 | Bruchman et al. |
| 9,597,086 B2 | 3/2017 | Larsen et al. |
| 9,743,932 B2 | 8/2017 | Amplatz |
| 9,744,033 B2 | 8/2017 | Bruchman et al. |
| 9,770,327 B2 | 9/2017 | Bruchman et al. |
| 9,795,475 B2 | 10/2017 | Bruchman et al. |
| 9,801,712 B2 | 10/2017 | Bruchman et al. |
| 10,022,219 B2 | 7/2018 | Bruchman et al. |
| 10,342,658 B2 | 7/2019 | Bruchman et al. |
| 10,470,878 B2 | 11/2019 | Bruchman et al. |
| 2001/0037142 A1 | 11/2001 | Stelter et al. |
| 2001/0051824 A1 | 12/2001 | Hopkins et al. |
| 2002/0007208 A1 | 1/2002 | Strecker et al. |
| 2002/0029077 A1 | 3/2002 | Leopold et al. |
| 2002/0045936 A1 | 4/2002 | Moe |
| 2002/0055773 A1 | 5/2002 | Campbell et al. |
| 2002/0099431 A1 | 7/2002 | Armstrong et al. |
| 2002/0151953 A1 | 10/2002 | Chobotov et al. |
| 2002/0198588 A1 | 12/2002 | Armstrong et al. |
| 2002/0198594 A1 | 12/2002 | Schreck |
| 2003/0004559 A1 | 1/2003 | Lentz et al. |
| 2003/0004560 A1 | 1/2003 | Chobotov et al. |
| 2003/0012905 A1 | 1/2003 | Zumbrum et al. |
| 2003/0023303 A1 | 1/2003 | Palmaz et al. |
| 2003/0040771 A1* | 2/2003 | Hyodoh ................ A61F 2/90 606/200 |
| 2003/0055492 A1 | 3/2003 | Shaolian et al. |
| 2003/0055495 A1 | 3/2003 | Pease et al. |
| 2003/0055496 A1 | 3/2003 | Cai et al. |
| 2003/0057156 A1* | 3/2003 | Peterson .......... A61B 17/12022 210/645 |
| 2003/0060871 A1 | 3/2003 | Hill et al. |
| 2003/0097175 A1 | 5/2003 | O'Connor et al. |
| 2003/0098383 A1 | 5/2003 | Luo et al. |
| 2003/0114917 A1 | 6/2003 | Holloway et al. |
| 2003/0139806 A1 | 7/2003 | Haverkost et al. |
| 2003/0149467 A1 | 8/2003 | Linder et al. |
| 2003/0181942 A1 | 9/2003 | Sutton |
| 2003/0211264 A1 | 11/2003 | Farnsworth et al. |
| 2003/0229394 A1 | 12/2003 | Ogle et al. |
| 2004/0019374 A1 | 1/2004 | Hojeibane et al. |
| 2004/0024442 A1 | 2/2004 | Sowinski et al. |
| 2004/0024448 A1 | 2/2004 | Chang et al. |
| 2004/0034366 A1 | 2/2004 | Van der Burg et al. |
| 2004/0044361 A1 | 3/2004 | Frazier et al. |
| 2004/0054396 A1 | 3/2004 | Hartley |
| 2004/0073289 A1 | 4/2004 | Hartley |
| 2004/0093070 A1 | 5/2004 | Hojeibane et al. |
| 2004/0122503 A1 | 6/2004 | Campbell et al. |
| 2004/0138734 A1 | 7/2004 | Chobotov et al. |
| 2004/0143315 A1 | 7/2004 | Bruun et al. |
| 2004/0167619 A1 | 8/2004 | Case et al. |
| 2004/0176839 A1 | 9/2004 | Huynh et al. |
| 2004/0260393 A1 | 12/2004 | Rahdert et al. |
| 2005/0038470 A1 | 2/2005 | Van Der Burg et al. |
| 2005/0049667 A1 | 3/2005 | Arbefeuille et al. |
| 2005/0070820 A1 | 3/2005 | Boutillette |
| 2005/0080476 A1 | 4/2005 | Gunderson et al. |
| 2005/0085890 A1 | 4/2005 | Rasmussen |
| 2005/0113861 A1 | 5/2005 | Corcoran |
| 2005/0125031 A1 | 6/2005 | Pipenhagen et al. |
| 2005/0137682 A1 | 6/2005 | Justino |
| 2005/0240257 A1 | 10/2005 | Ishimaru et al. |
| 2005/0261765 A1 | 11/2005 | Liddicoat |
| 2005/0283224 A1 | 12/2005 | King |
| 2005/0288767 A1 | 12/2005 | Kujawski et al. |
| 2006/0004433 A1 | 1/2006 | Greenberg et al. |
| 2006/0015171 A1 | 1/2006 | Armstrong |
| 2006/0036311 A1 | 2/2006 | Nakayama et al. |
| 2006/0058833 A1 | 3/2006 | Vancamp |
| 2006/0058889 A1 | 3/2006 | Case et al. |
| 2006/0135947 A1 | 6/2006 | Soltesz et al. |
| 2006/0155366 A1 | 7/2006 | LaDuca et al. |
| 2006/0190074 A1 | 8/2006 | Hill et al. |
| 2006/0254569 A1 | 11/2006 | Chipman |
| 2006/0259133 A1 | 11/2006 | Sowinski et al. |
| 2006/0264980 A1 | 11/2006 | Khairkhahan |
| 2006/0265053 A1 | 11/2006 | Hunt |
| 2006/0276883 A1 | 12/2006 | Greenberg et al. |
| 2006/0276888 A1 | 12/2006 | Lee et al. |
| 2006/0290027 A1 | 12/2006 | O'Connor et al. |
| 2007/0012624 A1 | 1/2007 | Bacino et al. |

(56) References Cited

U.S. PATENT DOCUMENTS

| | | |
|---|---|---|
| 2007/0027528 A1 | 2/2007 | Agnew |
| 2007/0027535 A1 | 2/2007 | Purdy et al. |
| 2007/0060999 A1 | 3/2007 | Randall et al. |
| 2007/0066993 A1 | 3/2007 | Kreidler |
| 2007/0067021 A1 | 3/2007 | Haverkost et al. |
| 2007/0088424 A1 | 4/2007 | Greenberg |
| 2007/0100427 A1 | 5/2007 | Perouse |
| 2007/0118209 A1 | 5/2007 | Strecker |
| 2007/0118210 A1 | 5/2007 | Pinchuk |
| 2007/0129786 A1 | 6/2007 | Beach et al. |
| 2007/0162048 A1 | 7/2007 | Quinn et al. |
| 2007/0167955 A1 | 7/2007 | Arnault de la Menardiere et al. |
| 2007/0198077 A1 | 8/2007 | Cully et al. |
| 2007/0198078 A1 | 8/2007 | Berra et al. |
| 2007/0208421 A1 | 9/2007 | Quigley |
| 2007/0213800 A1 | 9/2007 | Fierens et al. |
| 2007/0219467 A1 | 9/2007 | Clark |
| 2007/0248640 A1 | 10/2007 | Karabey et al. |
| 2007/0249980 A1 | 10/2007 | Carrez et al. |
| 2007/0250146 A1 | 10/2007 | Cully et al. |
| 2007/0250153 A1 | 10/2007 | Cully et al. |
| 2007/0254012 A1 | 11/2007 | Ludwig et al. |
| 2007/0255390 A1 | 11/2007 | Ducke et al. |
| 2007/0270891 A1 | 11/2007 | McGuckin |
| 2007/0288087 A1 | 12/2007 | Fearnot et al. |
| 2008/0027529 A1 | 1/2008 | Hartley et al. |
| 2008/0178434 A1 | 1/2008 | Bulanda |
| 2008/0033527 A1 | 2/2008 | Nunez et al. |
| 2008/0033534 A1 | 2/2008 | Cook |
| 2008/0039925 A1 | 2/2008 | Ishimaru et al. |
| 2008/0051876 A1 | 2/2008 | Ta et al. |
| 2008/0091261 A1 | 4/2008 | Long et al. |
| 2008/0114440 A1 | 5/2008 | Hlavka et al. |
| 2008/0119943 A1 | 5/2008 | Armstrong et al. |
| 2008/0125711 A1 | 5/2008 | Alpini et al. |
| 2008/0133004 A1 | 6/2008 | White |
| 2008/0147111 A1 | 6/2008 | Johnson |
| 2008/0200977 A1 | 8/2008 | Paul et al. |
| 2008/0208329 A1 | 8/2008 | Bishop |
| 2008/0269785 A1 | 10/2008 | Lampropoulos |
| 2008/0319531 A1 | 12/2008 | Doran et al. |
| 2009/0004239 A1 | 1/2009 | Ladet et al. |
| 2009/0005854 A1 | 1/2009 | Huang et al. |
| 2009/0030499 A1 | 1/2009 | Bebb et al. |
| 2009/0036976 A1 | 2/2009 | Beach et al. |
| 2009/0043373 A1 | 2/2009 | Arnault et al. |
| 2009/0048656 A1 | 2/2009 | Wen |
| 2009/0054723 A1 | 2/2009 | Khairkhahan et al. |
| 2009/0062838 A1 | 3/2009 | Brumleve et al. |
| 2009/0082844 A1 | 3/2009 | Zacharias et al. |
| 2009/0099596 A1 | 4/2009 | McGuckin, Jr. |
| 2009/0099640 A1 | 4/2009 | Weng |
| 2009/0112249 A1 | 4/2009 | Miles |
| 2009/0157175 A1 | 6/2009 | Benichou |
| 2009/0171386 A1 | 7/2009 | Amplatz |
| 2009/0182413 A1 | 7/2009 | Burkart et al. |
| 2009/0187197 A1 | 7/2009 | Roeber et al. |
| 2009/0216308 A1 | 8/2009 | Hartley |
| 2009/0216321 A1 | 8/2009 | Osborne et al. |
| 2009/0259291 A1 | 10/2009 | Kolbel et al. |
| 2010/0011564 A1 | 1/2010 | Millwee et al. |
| 2010/0016943 A1 | 1/2010 | Chobotov |
| 2010/0023048 A1 | 1/2010 | Mach |
| 2010/0023114 A1 | 1/2010 | Chambers et al. |
| 2010/0057195 A1 | 3/2010 | Roeder et al. |
| 2010/0094394 A1 | 4/2010 | Beach et al. |
| 2010/0094401 A1 | 4/2010 | Kolbel |
| 2010/0094405 A1 | 4/2010 | Cottone |
| 2010/0106240 A1 | 4/2010 | Duggal et al. |
| 2010/0159171 A1 | 6/2010 | Clough |
| 2010/0190254 A1 | 7/2010 | Chian et al. |
| 2010/0211052 A1 | 8/2010 | Brown et al. |
| 2010/0248324 A1 | 9/2010 | Xu et al. |
| 2010/0249922 A1 | 9/2010 | Li et al. |
| 2010/0280591 A1 | 11/2010 | Shin |
| 2011/0039690 A1 | 2/2011 | Niu |
| 2011/0040366 A1 | 2/2011 | Goetz et al. |
| 2011/0049757 A1 | 3/2011 | O'Connor et al. |
| 2011/0054515 A1* | 3/2011 | Bridgeman ........ A61B 17/0057 606/200 |
| 2011/0054519 A1 | 3/2011 | Neuss |
| 2011/0064781 A1 | 3/2011 | Cleek et al. |
| 2011/0066221 A1 | 3/2011 | White et al. |
| 2011/0125252 A1 | 5/2011 | Goddard |
| 2011/0130821 A1 | 6/2011 | Styrc |
| 2011/0142804 A1 | 6/2011 | Gaudette et al. |
| 2011/0218619 A1 | 9/2011 | Benichou et al. |
| 2011/0250689 A1 | 10/2011 | Baaijens et al. |
| 2011/0311746 A1 | 12/2011 | Ma et al. |
| 2011/0313503 A1 | 12/2011 | Berra et al. |
| 2012/0022630 A1 | 1/2012 | Wubbeling |
| 2012/0022638 A1 | 1/2012 | Leewood et al. |
| 2012/0046652 A1 | 2/2012 | Sokel |
| 2012/0058100 A1 | 3/2012 | Shastri et al. |
| 2012/0061314 A1 | 3/2012 | Choi et al. |
| 2012/0065667 A1 | 3/2012 | Javois et al. |
| 2012/0078357 A1 | 3/2012 | Conklin |
| 2012/0116496 A1 | 5/2012 | Chuter et al. |
| 2012/0123529 A1 | 5/2012 | Levi et al. |
| 2012/0123530 A1 | 5/2012 | Carpentier et al. |
| 2012/0129150 A1 | 5/2012 | Carbonell |
| 2012/0130473 A1 | 5/2012 | Norris et al. |
| 2012/0130474 A1 | 5/2012 | Buckley |
| 2012/0130475 A1 | 5/2012 | Shaw |
| 2012/0143242 A1 | 6/2012 | Masters |
| 2012/0143305 A1 | 6/2012 | Berra et al. |
| 2012/0172927 A1 | 7/2012 | Campbell et al. |
| 2012/0172965 A1 | 7/2012 | Kratzberg et al. |
| 2012/0172968 A1 | 7/2012 | Chuter et al. |
| 2012/0253450 A1 | 10/2012 | Case et al. |
| 2012/0253453 A1 | 10/2012 | Bruchman et al. |
| 2012/0283585 A1 | 11/2012 | Werneth et al. |
| 2012/0283773 A1 | 11/2012 | Van Tassel |
| 2012/0290082 A1 | 11/2012 | Quint et al. |
| 2012/0296360 A1 | 11/2012 | Norris et al. |
| 2012/0296418 A1 | 11/2012 | Bonyuet et al. |
| 2012/0323211 A1 | 12/2012 | Ogle et al. |
| 2012/0323270 A1 | 12/2012 | Lee |
| 2012/0323315 A1 | 12/2012 | Bruchman et al. |
| 2013/0023981 A1 | 1/2013 | Dierking et al. |
| 2013/0046371 A1 | 2/2013 | Greenberg et al. |
| 2013/0073029 A1 | 3/2013 | Shaw |
| 2013/0103074 A1* | 4/2013 | Riina ............... A61B 17/12022 606/200 |
| 2013/0123896 A1 | 5/2013 | Bloss et al. |
| 2013/0123908 A1 | 5/2013 | Hinchliffe et al. |
| 2013/0138138 A1 | 5/2013 | Clark |
| 2013/0150947 A1 | 6/2013 | Kaufmann et al. |
| 2013/0158647 A1 | 6/2013 | Norris et al. |
| 2013/0166021 A1 | 6/2013 | Bruchman et al. |
| 2013/0178889 A1 | 7/2013 | Miles |
| 2013/0184807 A1 | 7/2013 | Kovach et al. |
| 2013/0197631 A1 | 8/2013 | Bruchman et al. |
| 2013/0245666 A1 | 9/2013 | Larsen et al. |
| 2013/0245742 A1 | 9/2013 | Norris |
| 2013/0296912 A1 | 11/2013 | Ottma |
| 2013/0310924 A1 | 11/2013 | Groothuis et al. |
| 2013/0331929 A1 | 12/2013 | Mitra et al. |
| 2014/0005773 A1 | 1/2014 | Wheatley |
| 2014/0012303 A1 | 1/2014 | Heipl |
| 2014/0018841 A1 | 1/2014 | Peiffer |
| 2014/0031927 A1 | 1/2014 | Bruchman et al. |
| 2014/0046360 A1 | 2/2014 | van der Burg |
| 2014/0135817 A1 | 5/2014 | Tischler |
| 2014/0135897 A1 | 5/2014 | Cully et al. |
| 2014/0142617 A1 | 5/2014 | Larsen |
| 2014/0163671 A1 | 6/2014 | Bruchman et al. |
| 2014/0163673 A1 | 6/2014 | Bruchman et al. |
| 2014/0172066 A1 | 6/2014 | Goepfrich et al. |
| 2014/0172080 A1 | 6/2014 | Bruchman et al. |
| 2014/0172081 A1 | 6/2014 | Bruchman et al. |
| 2014/0172082 A1 | 6/2014 | Bruchman et al. |
| 2014/0172083 A1 | 6/2014 | Bruchman et al. |
| 2014/0180400 A1 | 6/2014 | Bruchman et al. |

(56) References Cited

U.S. PATENT DOCUMENTS

| | | |
|---|---|---|
| 2014/0180402 A1 | 6/2014 | Bruchman et al. |
| 2014/0188220 A1 | 7/2014 | Seguin |
| 2014/0253453 A1 | 9/2014 | Lo |
| 2014/0288642 A1 | 9/2014 | Yoshida et al. |
| 2014/0296908 A1 | 10/2014 | Ottma |
| 2014/0296909 A1 | 10/2014 | Heipl |
| 2014/0350592 A1 | 11/2014 | Kreidler |
| 2014/0379019 A1 | 12/2014 | Larsen |
| 2015/0005809 A1 | 1/2015 | Ayres et al. |
| 2015/0005810 A1 | 1/2015 | Center |
| 2015/0051695 A1 | 2/2015 | Shaw |
| 2015/0135537 A1 | 5/2015 | Bruchman et al. |
| 2015/0223757 A1 | 8/2015 | Werneth et al. |
| 2015/0224231 A1 | 8/2015 | Bruchman et al. |
| 2015/0257875 A1 | 9/2015 | Bruchman et al. |
| 2015/0257876 A1 | 9/2015 | Bruchman et al. |
| 2015/0257882 A1 | 9/2015 | Bortlein et al. |
| 2015/0265744 A1 | 9/2015 | Baaijens |
| 2015/0283297 A1 | 10/2015 | Baaijens et al. |
| 2015/0305749 A1 | 10/2015 | Alferness |
| 2015/0305862 A1 | 10/2015 | Bruchman et al. |
| 2015/0306277 A1 | 10/2015 | Pathak et al. |
| 2015/0351904 A1 | 12/2015 | Cooper et al. |
| 2015/0366663 A1 | 12/2015 | Bruchman et al. |
| 2016/0008133 A9 | 1/2016 | Day et al. |
| 2016/0067374 A1 | 3/2016 | Puckett et al. |
| 2016/0074161 A1 | 3/2016 | Bennett |
| 2016/0100939 A1 | 4/2016 | Armstrong et al. |
| 2016/0175095 A1 | 6/2016 | Dienno et al. |
| 2016/0175096 A1 | 6/2016 | Dienno et al. |
| 2016/0317299 A1 | 11/2016 | Alkhatib |
| 2016/0331382 A1 | 11/2016 | Center |
| 2017/0042674 A1 | 2/2017 | Armstrong |
| 2017/0181751 A1 | 6/2017 | Larsen |
| 2017/0319338 A1 | 11/2017 | Bruchman et al. |
| 2018/0008406 A1 | 1/2018 | Bruchman et al. |
| 2018/0200050 A1 | 7/2018 | Bruchman et al. |
| 2019/0110880 A1 | 4/2019 | Fox et al. |
| 2019/0114303 A1 | 4/2019 | Peloski |
| 2019/0258641 A1 | 8/2019 | Peloski |
| 2019/0269506 A1 | 9/2019 | Bruchman et al. |
| 2021/0038230 A1 | 2/2021 | Larsen et al. |

FOREIGN PATENT DOCUMENTS

| | | |
|---|---|---|
| CN | 2904980 Y | 5/2007 |
| CN | 101304693 A | 11/2008 |
| CN | 101554343 | 10/2009 |
| CN | 101780306 | 7/2010 |
| CN | 101965161 | 2/2011 |
| CN | 201879866 U | 6/2011 |
| CN | 201930098 U | 8/2011 |
| CN | 102908174 | 2/2013 |
| CN | 103347467 A | 10/2013 |
| DE | 102014102725 A1 | 9/2015 |
| EP | 0150608 A1 | 8/1985 |
| EP | 0293090 A2 | 11/1988 |
| EP | 0313263 A2 | 4/1989 |
| EP | 0664107 A1 | 7/1995 |
| EP | 0679372 A2 | 11/1995 |
| EP | 0815806 A2 | 1/1998 |
| EP | 0893108 A2 | 1/1999 |
| EP | 0773971 B1 | 6/1999 |
| EP | 1318775 A1 | 6/2003 |
| EP | 1977719 A2 | 10/2008 |
| EP | 2074953 A1 | 7/2009 |
| EP | 2481381 | 8/2012 |
| EP | 2596754 A1 | 5/2013 |
| FR | 2896405 A1 | 7/2007 |
| GB | 2344054 A | 5/2000 |
| JP | 02-000645 A | 1/1990 |
| JP | 1996126704 | 5/1996 |
| JP | 09-501759 A | 2/1997 |
| JP | 09-241412 A | 9/1997 |
| JP | 2001506902 A | 7/1998 |
| JP | 11-290448 A | 10/1999 |
| JP | 2002503114 A | 1/2002 |
| JP | 2002518086 A | 6/2002 |
| JP | 2004-510471 A | 4/2004 |
| JP | 2004167239 | 6/2004 |
| JP | 2004188219 A | 7/2004 |
| JP | 2005-505320 A | 2/2005 |
| JP | 2005-530549 A | 10/2005 |
| JP | 2007502689 A1 | 2/2007 |
| JP | 2007518465 A | 7/2007 |
| JP | 2008-506459 A | 3/2008 |
| JP | 2008-531117 A | 8/2008 |
| JP | 2009-542421 A | 12/2009 |
| JP | 2010527742 A | 8/2010 |
| JP | 2010-535075 A | 11/2010 |
| JP | 2011-005292 | 1/2011 |
| JP | 2011509117 A | 3/2011 |
| JP | 2011511693 A | 4/2011 |
| JP | 2011516202 | 5/2011 |
| JP | 2013-545515 A | 12/2013 |
| JP | 2014501563 A | 1/2014 |
| JP | 2014501565 A | 1/2014 |
| JP | 2014502180 A | 1/2014 |
| JP | 2014-533189 A | 12/2014 |
| JP | 2014-533970 A | 12/2014 |
| JP | 2015-534881 A | 12/2015 |
| RU | 2124986 C1 | 1/1999 |
| WO | 95/05555 A1 | 2/1995 |
| WO | 95/28899 A1 | 11/1995 |
| WO | WO-1996018361 A1 | 6/1996 |
| WO | 97/10871 A1 | 3/1997 |
| WO | WO-1997048350 A1 | 12/1997 |
| WO | 98/26731 A2 | 6/1998 |
| WO | WO-1999065420 A1 | 12/1999 |
| WO | WO-2000013613 A1 | 3/2000 |
| WO | 00/41649 A1 | 7/2000 |
| WO | 00/62716 A1 | 10/2000 |
| WO | WO-2001021109 A1 | 3/2001 |
| WO | WO-2001030266 A1 | 5/2001 |
| WO | 01/74272 A2 | 10/2001 |
| WO | 02/24118 A1 | 3/2002 |
| WO | 02/24119 A1 | 3/2002 |
| WO | WO-2002028317 A2 | 4/2002 |
| WO | 02/60506 A1 | 8/2002 |
| WO | 2002/100454 A1 | 12/2002 |
| WO | 03/47468 A1 | 6/2003 |
| WO | 2004/000375 A1 | 12/2003 |
| WO | WO-2007092354 A2 | 8/2004 |
| WO | WO-2008063464 A2 | 5/2005 |
| WO | WO-2005072652 | 8/2005 |
| WO | 2006/000763 A2 | 1/2006 |
| WO | WO-2006007389 A1 | 1/2006 |
| WO | 2006/019626 A1 | 2/2006 |
| WO | 2006/091382 A1 | 8/2006 |
| WO | 2006/127756 A2 | 11/2006 |
| WO | 2007/002320 A1 | 1/2007 |
| WO | 2007/016251 A2 | 2/2007 |
| WO | 2008/006003 A2 | 1/2008 |
| WO | 2008/028964 A2 | 3/2008 |
| WO | 2008/036870 A2 | 3/2008 |
| WO | 2008/049045 A2 | 4/2008 |
| WO | WO-2008047092 A1 | 4/2008 |
| WO | 2009/017827 A1 | 2/2009 |
| WO | 2009/038761 A1 | 3/2009 |
| WO | 2009/045332 A2 | 4/2009 |
| WO | WO-2009088905 | 7/2009 |
| WO | 2009/100210 A1 | 8/2009 |
| WO | WO-2009102441 A1 | 8/2009 |
| WO | WO-2009126227 A2 | 10/2009 |
| WO | 2009/149462 A2 | 12/2009 |
| WO | WO-2009148594 A1 | 12/2009 |
| WO | 2010/006783 A1 | 1/2010 |
| WO | WO-2010001012 A1 | 1/2010 |
| WO | 2010/030766 A1 | 3/2010 |
| WO | WO-2010024881 | 3/2010 |
| WO | WO-2010041038 A1 | 4/2010 |
| WO | WO-2010044854 A1 | 4/2010 |
| WO | WO-2010063795 A1 | 6/2010 |
| WO | WO-2010081041 | 7/2010 |

(56) References Cited

FOREIGN PATENT DOCUMENTS

| | | |
|---|---|---|
| WO | WO-2010090699 A1 | 8/2010 |
| WO | WO-2010105195 A2 | 9/2010 |
| WO | 2010/132707 A1 | 11/2010 |
| WO | WO-2011031981 | 3/2011 |
| WO | WO-2011062858 A1 | 5/2011 |
| WO | 2011/065809 A2 | 6/2011 |
| WO | WO-2012068257 A2 | 5/2012 |
| WO | 2012/109297 | 8/2012 |
| WO | 2012/135603 A2 | 10/2012 |
| WO | 2012/163257 | 12/2012 |
| WO | 2012/167131 A1 | 12/2012 |
| WO | WO-2013040431 A1 | 3/2013 |
| WO | WO-2013137977 A1 | 9/2013 |
| WO | 2014/036439 A2 | 3/2014 |
| WO | 2014/078078 A1 | 5/2014 |
| WO | 2014/078531 A1 | 5/2014 |
| WO | 2014/210263 A1 | 12/2014 |
| WO | 2015/085138 A1 | 6/2015 |
| WO | WO-2015132668 A1 | 9/2015 |
| WO | 2016/028591 A1 | 2/2016 |
| WO | 2016/044223 A1 | 3/2016 |
| WO | 2016/183495 A2 | 11/2016 |

OTHER PUBLICATIONS

European Search Report from EP17166472.5, dated Nov. 7, 2017, 7 pages.
International Preliminary Report on Patentability for PCT/US2012/055537, dated Mar. 18, 2014, 10 pages.
International Search Report and Written Opinion for PCT/US2012/055537, dated Dec. 5, 2012, 5 pages.
International Search Report and Written Opinion for PCT/US2013/022404 dated May 8, 2013, corresponding to U.S. Appl. No. 13/743,118, 7 pages.
International Search Report and Written Opinion from PCT/US2016/032487, dated Dec. 14, 2016, 20 pages.
Ueda et al, Incomplete Endograft Apposition to the Aortic Arch: Bird-Beak Configuration Increases Risk of Endoleak Formation after Thoracic Endovascular Aortic Repair, Radiology: vol. 255 No. 2; May 2010, pp. 645-652.
Search Report and Written Opinion from PCT/US2018/056031, dated Feb. 1, 2019, 18.
European Search Report and Search Opinion Received for EP Application No. 19179823.0, dated Oct. 1, 2019, 10 pages.
European Search Report for European Application No. 16155556.0 dated Aug. 1, 2016, 10 pages.
International Preliminary Report on Patentability for PCT/US2012055445 dated Mar. 18, 2014, 9 pages.
International Preliminary Report on Patentability received for PCT Patent Application No. PCT/US2014/044258, dated Jan. 7, 2016, 7 pages.
International Preliminary Report on Patentability received for PCT Patent Application No. PCT/US2016/032487, dated Nov. 23, 2017, 13 pages.
International Search Report & Written Opinion in International Application No. PCT/US2012/055445, dated Dec. 5, 2012, 15 pages.
International Search Report and Written Opinion for PCT/US2012/061928 dated Jan. 22, 2013, corresponding to U.S. Appl. No. 13/658,597, 8 pages.
International Search Report and Written Opinion for PCT/US2014/066153 dated Feb. 17, 2015, corresponding to U.S. Appl. No. 14/084,592, 5 pages.
International Written Opinion received for PCT Patent Application No. PCT/US14/044258, dated Oct. 29, 2014, 5 pages.
Nakayama, Yasuhide. Microporous Stent Achieves Brain Aneurysm Occlusion Without Disturbing Branching Flow. NeuroNews Nov. 2012; 8:1-2.
Nishi S, Nakayama Y, Ishibashi-Ueda H, Okamoto Y, Yoshida M. Development of microporous self-expanding stent grafts for treating cerebral aneurysms: designing micropores to control intimal hyperplasia. J Artif Organs 2011; 14:348-356.

* cited by examiner

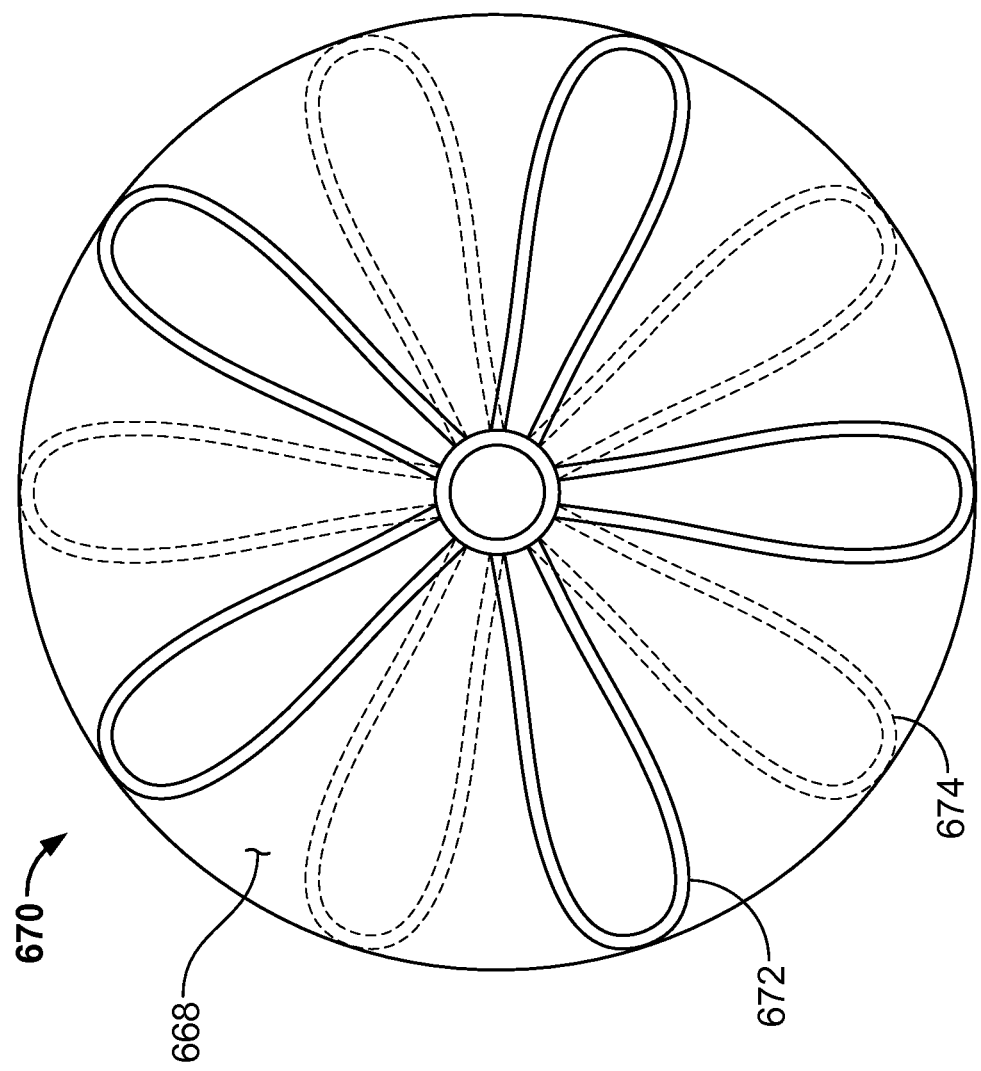
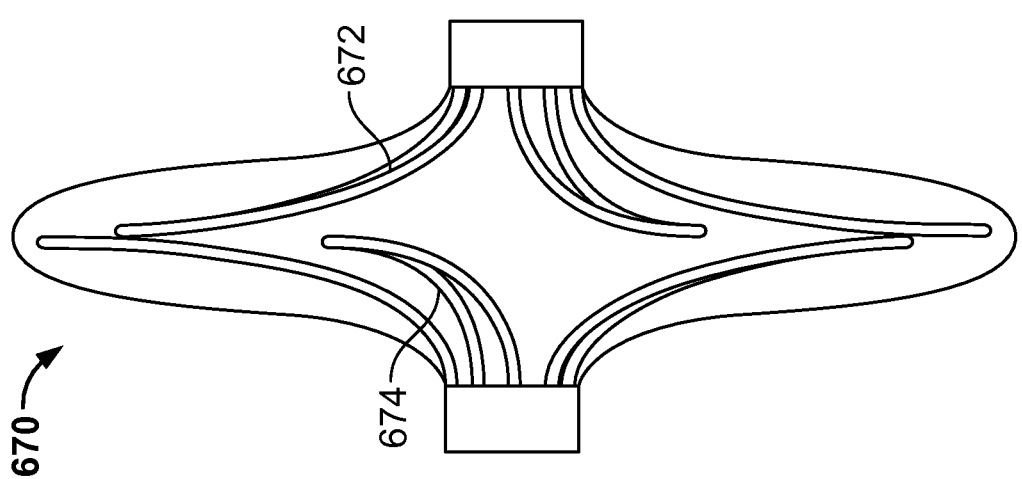

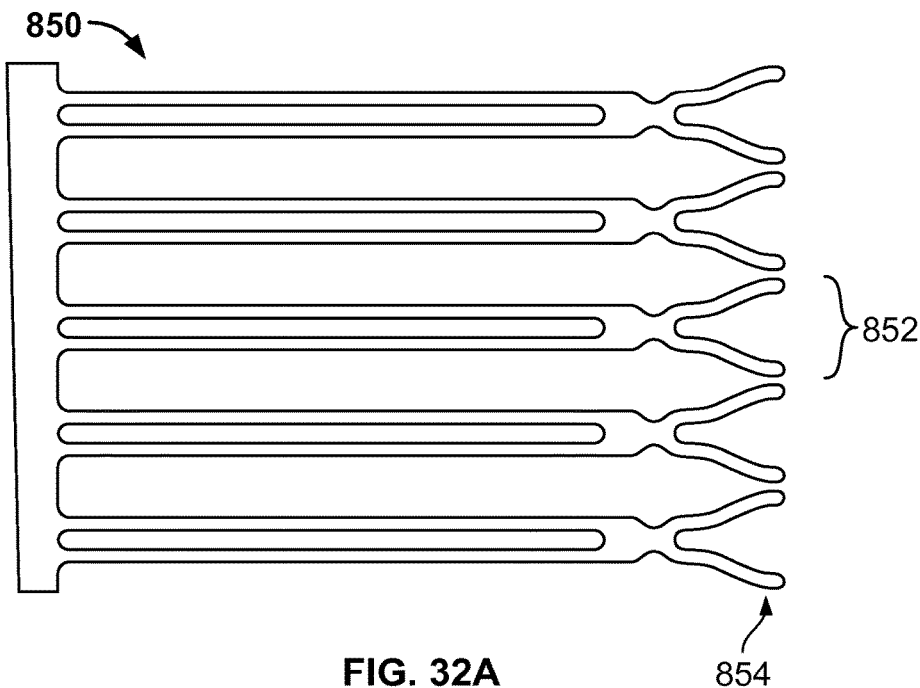
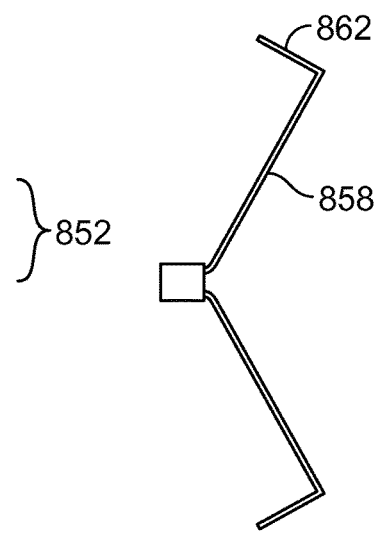
FIG. 32A   FIG. 32B
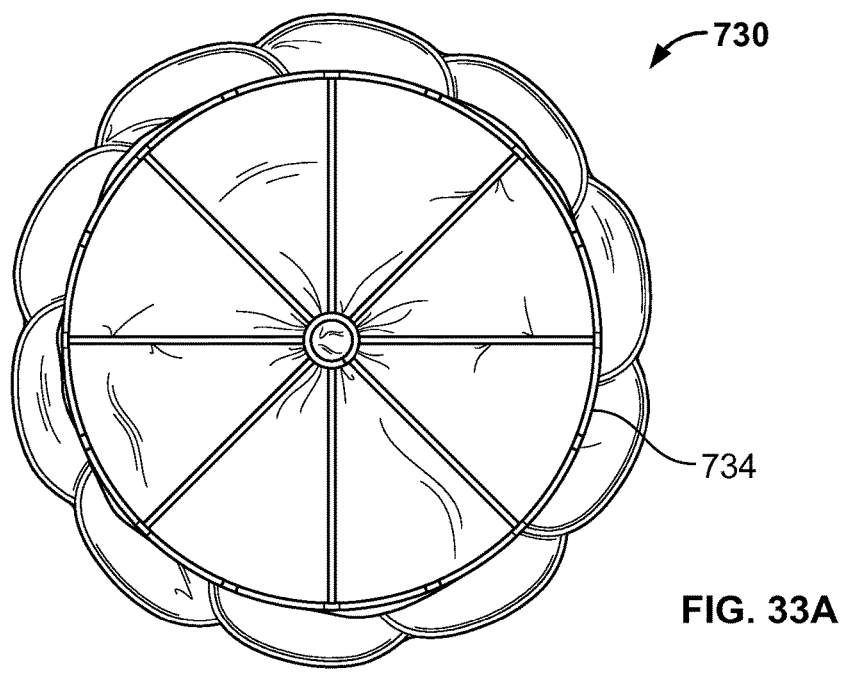
FIG. 33A

SPACE FILLING DEVICES

TECHNICAL FIELD

The present disclosure relates to implantable medical devices that may be used to occlude apertures, conduits, or structures within a patient.

BACKGROUND

Cardiac features such as atrial appendages can contribute to cardiac blood flow disturbance, which is associated with a number of cardiac-related pathologies. For example, complications caused by blood flow disturbance within the left atrial appendage (LAA) and associated with atrial fibrillation can contribute to embolic stroke. The LAA is a muscular pouch extending from the anterolateral wall of the left atrium of the heart and serves as a reservoir for the left atrium. During a normal cardiac cycle, the LAA contracts with the left atrium to pump blood from the LAA, which generally prevents blood from stagnating within the LAA. However, during cardiac cycles characterized by arrhythmias (e.g., atrial fibrillation), the LAA often fails to sufficiently contract, which can allow blood to stagnate within the LAA. Stagnant blood within the LAA is susceptible to coagulating and forming a thrombus, which can dislodge from the LAA and ultimately result in an embolic stroke.

SUMMARY

In a first general aspect, an occlusive device includes a covering component configured to modulate passage of blood or thrombus through the covering component. The occlusive device also includes an occlusion frame that includes a plurality of elongate frame members, each of which includes a portion of a tube. The elongate frame members are arranged to form a generally disc-shaped member when the occlusion frame assumes an expanded configuration, and each of the elongate frame members forms a petal of the generally disc-shaped member. Adjacent petals of the generally disc-shaped member at least partially overlap one another, and the occlusion frame is at least partially covered by the covering component. The occlusive device further includes an anchor frame that includes a plurality of anchor members configured to anchor the occlusive device at an implant location. The occlusive device further includes a first hub component from which the plurality of elongate frame members extend, where the first hub component is disposed between the occlusion frame and the anchor frame. The occlusive device further includes a second hub component from which the anchor members extend, where the second hub component is disposed between the occlusion frame and the anchor frame. The occlusive device further includes a connecting member that connects the first hub component to the second hub component.

Various implementations may include one or more of the following. Each anchor member of the plurality of anchor members may include a wire. Each anchor member of the plurality of anchor members may include a portion of the tube. Each anchor member of the plurality of anchor members may include a portion of a second tube. The connecting member may include one or more nitinol wires. The first hub component, the second hub component, and the connecting member may be covered by the covering component. The anchor frame may be at least partially covered by the covering component. Each of the anchor members may include a first portion that extends generally distally and radially from the second hub component, a second portion that extends from the first portion in a generally distal and radial direction, and a third portion that extends from the second portion in a generally proximal and radial direction. The first portion may extend from the second hub component at an angle that is about 30 degrees distal from a directly radial direction, wherein the second portion may extend from the first portion at an angle that is about 75 degrees distal from a directly radial direction, and wherein the third portion may extend from the second portion at an angle that is about 60 degrees proximal from a directly radial direction. Each of the anchor members may include a first portion that extends generally radially from the second hub component, a second portion that extends from the first portion in a generally proximal direction. The connecting member may be flexible and may include a first end portion that is attached to the first hub component and a second end portion that is attached to the second hub component. The tube may include nitinol.

In a second general aspect, an occlusive device includes a covering component configured to modulate passage of blood or thrombus through the covering component, and an occlusion frame that includes a plurality of elongate frame members. The elongate frame members are arranged to form a generally disc-shaped member when the occlusion frame assumes an expanded configuration, and each of the elongate frame members forms a petal of the generally disc-shaped member. Adjacent petals of the generally disc-shaped member at least partially overlap one another, and the occlusion frame is at least partially covered by the covering component. The occlusive device also includes an anchor frame that includes a plurality of anchor members, each of which includes a portion of a tube, wherein the anchor members are configured to anchor the occlusive device at an implant location. The occlusive device also includes a first hub component from which the plurality of elongate frame members extend, and the first hub component is disposed between the occlusion frame and the anchor frame. The occlusive device further includes a second hub component from which the anchor members extend, and the second hub component is disposed between the occlusion frame and the anchor frame. The occlusive device further includes a connecting member that connects the first hub component to the second hub component.

In a third general aspect, an occlusive device includes a covering component configured to modulate passage of blood or thrombus through the covering component, and an occlusion frame that includes a plurality of elongate frame members arranged to form a generally disc-shaped member when the occlusion frame assumes an expanded configuration. Each of the elongate frame members forms a generally disc-shaped member, wherein adjacent petals of the generally disc-shaped member at least partially overlap one another, and wherein the occlusion frame is at least partially covered by the covering component. The occlusive device further includes an anchor frame that includes first and second anchor arms configured to anchor the occlusive device at an implant location, where the first anchor arm is oriented opposite the second anchor arm. The occlusive device further includes a first hub component from which the plurality of elongate frame members extend, and the first hub component is disposed between the occlusion frame and the anchor frame. The occlusive device further includes a second hub component from which the first and second anchor arms extend, and the second hub component is disposed between the occlusion frame and the anchor frame.

The occlusive device further includes a flexible connecting member that includes first and second end portions, wherein the first end portion is attached to the first hub component and the second end portion is attached to the second hub component.

In a fourth general aspect, an occlusive device includes a frame and a covering component attached to the frame such that the covering component at least partially modulates passage of blood or thrombus through at least a portion of the occlusive device. The frame comprises a hub, a plurality of curved radial struts extending radially outward from the hub and defining an occlusive face of the frame, and a plurality of cells extending from the plurality of curved radial struts and arranged in interconnected rows of cells to define a lateral outer surface of the frame.

Various implementations of such an occlusive device may optionally include one or more of the following features. The frame may further comprise a plurality of anchor elements that extend radially outward from the lateral outer surface of the frame. The plurality of anchor elements may be at least partially positioned in the interstitial spaces defined by at least some cells of the plurality cells. The frame may be formed from a single tubular piece of precursor material. The cells may be helically biased to comprise rectangular shapes. The occlusive device may further comprise a gathering member, wherein the gathering member is interwoven through apices of an end-most row of cells. The gathering member may be in tension such that each cell of the end-most row of cells is made to be positioned nearer to the other cells of the end-most row of cells than without the tension. In some embodiments, the cells are diamond-shaped cells. In some embodiments, the cells are hexagonal cells.

The details of one or more embodiments are set forth in the accompanying drawings and the description below. Other features, objects, and advantages will be apparent from the description and drawings, and from the claims.

BRIEF DESCRIPTION OF THE DRAWINGS

FIG. 7A is a side view of another example disc-shaped member that can be used with occlusive devices provided herein.

FIG. 7B is an end view of the disc-shaped member of FIG. 7A.

FIGS. 30A, 31A, and 32A are views of an example cutting patterns that can be used in cutting a tube (or a portion of a tube) to create an anchor frame.

FIGS. 30B, 31B, and 32B are views showing portions of anchor frames created using the cutting patterns of FIGS. 30A, 31A, and 32A.

FIG. 33A is a top view of another example occlusive device in accordance with embodiments provided herein.

Like reference symbols in the various drawings indicate like elements.

DETAILED DESCRIPTION

Figure 1:
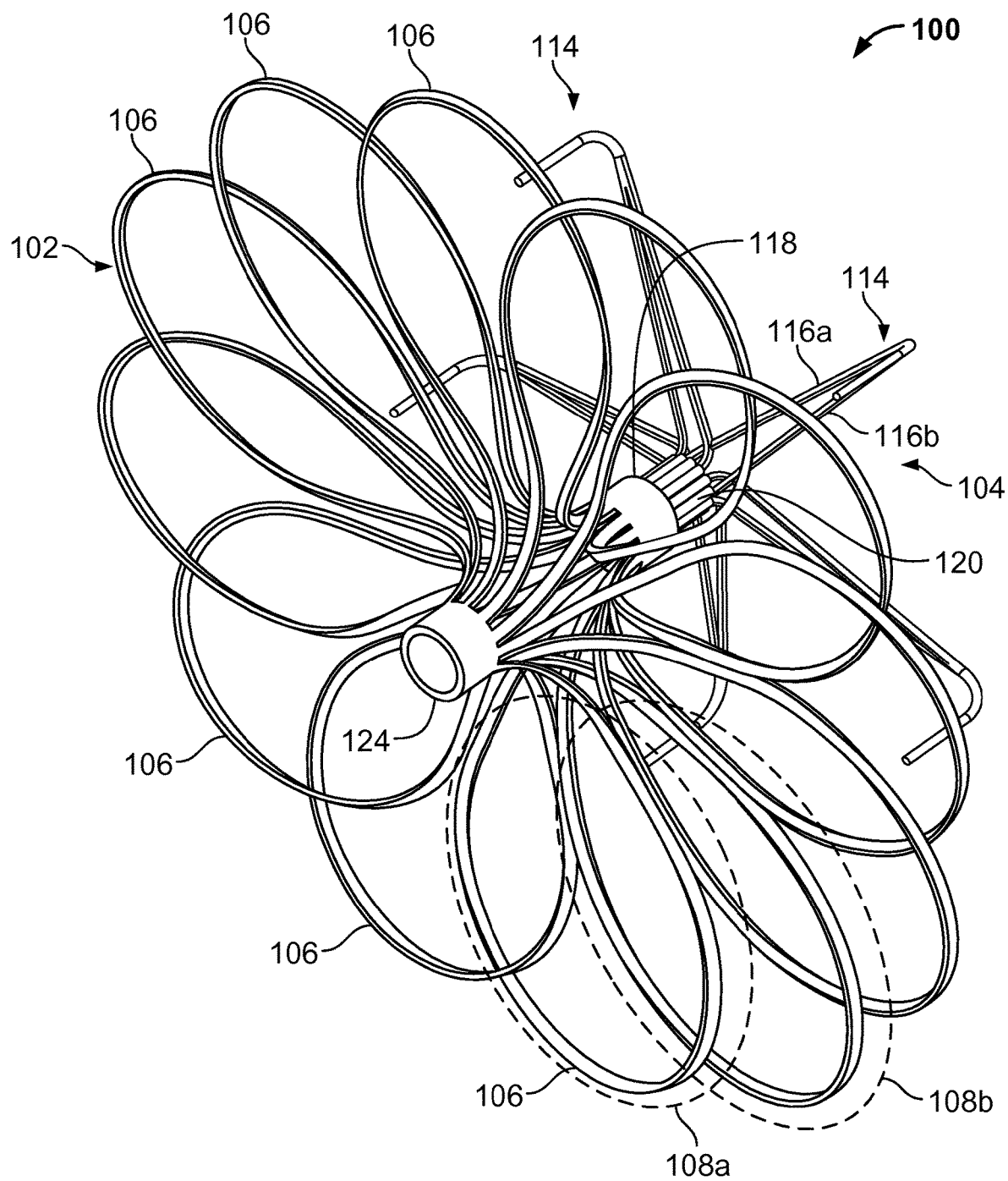
FIG. 1 is a perspective view of an example device frame that can be used to occlude a hole, defect, aperture, or appendage within a body of a patient.

This document describes devices, systems and methods that are useful, for example, for fully, partially, or substantially occluding spaces, holes, defects, apertures, appendages, vessels or conduits within a body of a patient. An additional use, in some implementations, can include filtering. Several implantable medical devices are described herein, and in general any of the features described with respect to a particular device may also be used with any of the other devices described herein. In some examples, one or more features described with respect to a particular device may replace or be substituted for one or more features of another device. In some examples, one or more features described with respect to a particular device may be added to or included with another device. Also, various combinations or sub-combinations of any of the features described herein may generally be used with any of the devices described herein.

For example, devices described herein can include an occlusion portion and an anchor portion, and several different types of occlusion portions and anchor portions are described. While a particular embodiment may include a particular occlusion portion and a particular anchor portion, in general, any of the occlusion portions described herein can be used with any of the anchor portions described herein, and vice versa, in various embodiments. In similar fashion, for devices where the occlusion portion and the anchor portion are not integral, several types of connecting members or techniques are described for combining an occlusion portion with an anchor portion to form an occlusion device, and in general any of the connecting members or techniques described herein may be used with any combination of an occlusion portion and an anchor portion. In some examples, the occlusion portion and the anchor portion may be constructed separately and then combined to form the device. In some examples, the occlusion portion and the anchor portion may be constructed simultaneously.

In general, any of the implantable medical devices described herein can be delivered to, and deployed at, an in vivo deployment site within a body of a patient using various minimally invasive transcatheter deployment techniques. For example, any of the implantable medical devices described herein may be releasably attached to a delivery catheter, and the device and delivery catheter may be loaded into a delivery sheath. The delivery sheath may be introduced to the vasculature of the patient and advanced through the vasculature, until a distal end of the delivery sheath is located at or near the target in vivo deployment site. The implantable medical device may be deployed at the deployment site, for example by pushing the device out the distal end of the delivery sheath using the delivery catheter and detaching the device from the delivery catheter. In some examples, the device can be deployed by retracting the delivery sheath while maintaining (or advancing) a position of the delivery catheter and the implantable medical device, and then detaching the device from the delivery catheter. In some implementations, a first portion of the device (e.g., an anchor portion) is released from the delivery sheath while a second portion of the device (e.g., an occlusion portion) remains constrained by the delivery sheath, a positioning of the first portion of the device is verified, and then the second portion of the device is released from the delivery sheath. The delivery catheter and delivery sheath can then be withdrawn or retracted from the body of the patient. In some examples, a retrieval element such as a tether, suture, or cable, is releasably attached to a portion of the device. The retrieval element can be used to retrieve or recapture the device after deployment, if desired.

Some embodiments of the implantable medical devices described herein can be used to occlude a left atrial appendage (LAA) of a human heart. The implantable medical devices can be delivered in an endovascular manner through or over a catheter system to a delivery site, such as the LAA or other appropriate delivery site, and deployed at the site. The implantable medical devices can be deployed within the LAA and/or across the ostium of the LAA to isolate the LAA from the main chamber of the left atrium (left atrial chamber), for example. This may prevent thrombus formation within the LAA and/or thrombus exit from the LAA. In this manner, a risk of stroke may be reduced or minimized.

Without limitation devices described here can be used to occlude spaces, holes, defects, apertures, vessels, conduits, or appendages within a body of a patient, including the heart, such as right or left atrial appendages, fistulas, aneurysms, patent ductus arteriousus, atrial septal defects, ventricular septal defects, paravalvular leaks, arteriovenous malformations, or body vessels including but not limited to the GI tract. For example, in some embodiments the occlusive devices provided herein can be used to occlude an opening in the wall of a body vessel such as the colon. The occlusive devices provide a frame that is compliant enough to conform to a wide variety of opening geometries and sizes, and offer a high degree of conformability to conform to various structural geometries at the deployment site. Particularly, embodiments of the devices can provide a left atrial appendage occlusion device frame that provides firm, secure anchoring with significantly reduced clinical sequela from piercing or without traumatic piercing of the left atrial appendage tissue.

In some implementations, the devices described herein can assume two or more configurations. For example, while the device is being delivered to the deployment site within the delivery sheath, the device may assume a collapsed or delivery configuration. Following deployment of the device, the device may assume an expanded or deployed configuration. While the device is being deployed, for example, the device may assume one or more partially expanded or partially deployed configurations.

Figure 2:
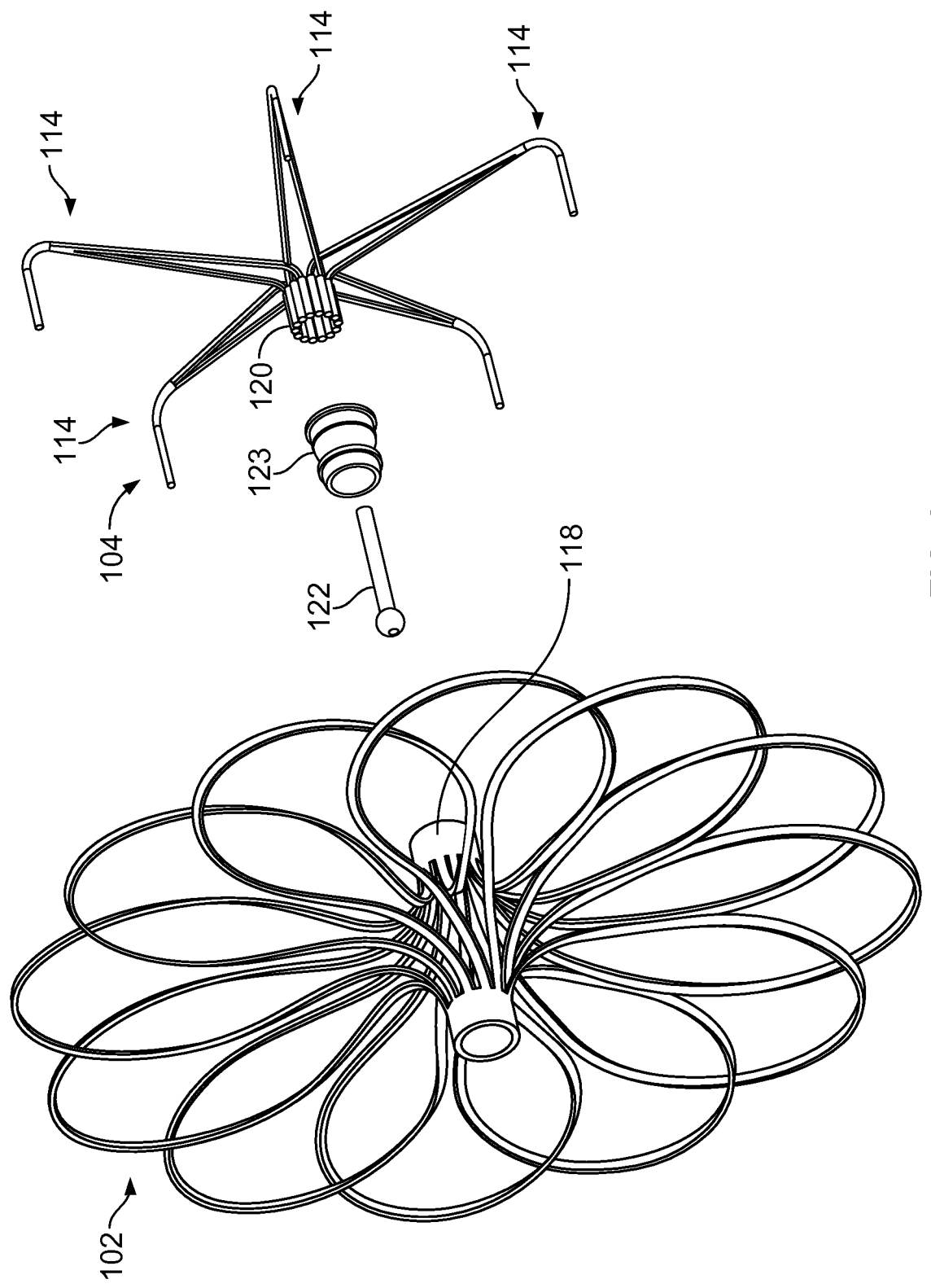
FIG. 2 is an exploded view of the example device frame of FIG. 1.

FIG. 1 is a perspective view of an example device frame 100 that can be used to occlude a hole, defect, aperture, or appendage within a body of a patient. The device frame 100 includes two sub-frames: an occlusion frame 102 and an anchor frame 104, each of which is also shown in FIG. 2, which is an exploded view of the device frame 100 of FIG. 1. While the device frames discussed herein will generally be described as including an occlusion frame because the examples are generally described with reference to occlusion applications, for filtering applications where occlusion is not desired, the occlusion frame may be referred to as a filter frame. That is, any of the described occlusion frames may also be filter frames, for example. As will be described further below, at least a portion of the occlusion frame 102 can be covered by a covering component (not shown) that is configured to modulate the passage of blood or thrombus through the covering component, i.e., to substantially occlude the flow of blood and/or thrombus through the covering component. In some embodiments, the anchor frame 104 is not covered by the covering component. In some embodiments, a portion of the anchor frame 104 is covered by the covering component, and in some embodiments the anchor frame is substantially covered by the covering component (or by a second covering component).

The occlusion frame 102, in this example, includes twelve elongate frame members 106. In other examples, the occlusion frame 102 can include two, three, four, five, six, seven, eight, nine, ten, or more elongate frame members 106. Each of the elongate frame members 106 is configured to form a petal 108 (see e.g., petal 108a and petal 108b) of the occlusion frame 102, and together the petals 108 form a generally disc-shaped member 110 (see FIG. 3) of the occlusion frame 102. As can be seen with reference to FIG. 1, adjacent petals (e.g., petal 108a and petal 108b) of the occlusion frame 102 partially overlap with one another in some embodiments. The generally disc-shaped member 110 may have a generally circular shape in some embodiments, and in other embodiments may have an oval or a generally elliptical shape, or other appropriate shape for occluding according to the intended purpose. In some embodiments, the generally disc-shaped member is symmetric about a longitudinal axis of the device. In some embodiments, the generally disc-shaped member is asymmetric or eccentric about a longitudinal axis of the device. This example disc-shaped member 110 having elongate frame members 106 that are configured to form petals is one type of disc-shaped member and many others that do not include petals are also envisioned, including but not limited to those described in reference to FIGS. 6A-10 and 34B-36B.

The anchor frame 104 includes, in this example, five elongate anchor members 114 that can be used to secure the device to tissue and anchor the occlusion device 100 at an implant location. In other examples, the anchor frame 104 can include two, three, four, six, seven, eight, nine, ten, or more anchor members 114. The elongate anchor members 114 can have various shapes, sizes, and configurations. Each of the elongate anchor members 114 in this example includes a first anchor arm 116a and a second anchor arm 116b. By including two anchor arms (116a and 116b) for each anchor member 114, radial opposition force of the anchor members 114 may be increased. In some cases, a lateral stiffness may also be increased. In other examples, the elongate anchor members 114 may include a single anchor arm.

The elongate frame members 106 extend from a first hub component 118, and the elongate anchor members 114 extend from a second hub component 120. The first hub component 118 and the second hub component are each disposed between the occlusion frame 102 and the anchor frame 104. A connecting member 122 (see FIG. 2) connects the first hub component 118 and the second hub component. In some embodiments, connecting member 122 is flexible. In this context 'flexible' means being easily moved under application of little force. In other embodiments, connecting member 122 may be relatively inflexible. In some of the discussion that follows, it may be assumed that connecting member 122 is flexible. For example, the flexible connecting member 122 can include a first end that is connected to the first hub component 118, and a second end that is connected to the second hub component 120. The flexible connecting member 122 may permit articulation between the occlusion frame 102 and the anchor frame 104. For example, the flexible connecting member 122 can provide an articulation joint between the occlusion frame 102 and the anchor frame 104. Flexible connecting member 122 of FIG. 2 includes a ball end (e.g., a laser-welded ball) at its first end, and the ball end may be received by the first hub component 118. In other examples, the flexible connecting member can also include a second ball on its second end, and the second ball can be received by the second hub component 120. The ball ends (or other retaining feature) may function to retain the first and second hub components 118, 120, in various embodiments. In some examples, the connecting member 122 can have a helical shape, or a coiled shape. In some examples, connecting member 122 can include a linkage. In some examples, connecting member includes a beaded chain.

In some examples, the second hub component 120 can be attached to the first hub component 118 with the flexible connecting member 122 and a collar lock component 123. The collar lock component 123 can optionally be used as an engagement feature, and may be attached to the first hub component 118 with tab features or other means of a mechanical stop. For example, the collar lock 123 can include a groove on an inside surface of the collar lock, and the first hub component 118 can include tab features that can lock into the groove of the collar lock. As such, the collar lock 123 may facilitate a snap-fit assembly of the device, for example.

Referring again to the occlusion frame 102 and elongate frame members 106, occlusion frame 102 is formed by cutting a tube of material. For example, a tube is cut according to a prescribed pattern to form elongate frame members 106, where a first end of the elongate frame members 106 extend from the first hub component 118. A third hub component 124 terminates the other end of the elongate frame members 106 in the depicted example. The first hub component 118 and the third hub component 124 may be cylindrical portions of the tube. First hub component 118, third hub component 124, and elongate frame members 106 may all be considered portions of a tube, as they comprise the remaining portions of the tube following the cutting process. In some embodiments, the elongate frame members 106 extend helically between the first hub component 118 and the third hub component 120.

The tube used to form the occlusion frame 102 (and the frames of the other devices provided herein) can be made of nitinol (NiTi), L605 steel, stainless steel, or any other appropriate biocompatible material. In some embodiments, bioresorbable or bioabsorbable materials may be used, for example a bioresorbable or bioabsorbable polymer. The tube of material may be cut in variety of ways. For example, the tube may be cut by a laser. Alternatively, the tube may be cut by a blade, by a water jet, or electrochemically milled, to list just a few examples.

In some embodiments, some or all portions of the occlusion frame 102 (and the frames of the other devices provided herein) are coated (e.g., sputter coated) with a radiopaque coating for enhanced radiographic visibility. For example, in some such embodiments portions or all of the frames can be coated with a noble metal such as, but not limited to, tantalum, platinum, and the like.

Referring again to anchor frame 104, the elongate anchor members 114 are formed by wires that extend from second hub component 120. The second hub component 120 can have various configurations. In the depicted example, the second hub component 120 has a generally ring shape, with a series of holes axially through the wall of the ring. First ends of wires that form the anchor members 114 can be attached to the second hub component 120, for example by welding or by a mechanical termination. As can be seen with reference to FIG. 3, first portions 126 of the wires that form the anchor members 114 extend generally radially from the second hub component 120, at an angle that is about 10 degrees distal from a directly radial direction. Second portions 128 of the wires that form the anchor members 114 are directed in a proximal direction toward the disc 110.

Figure 3:
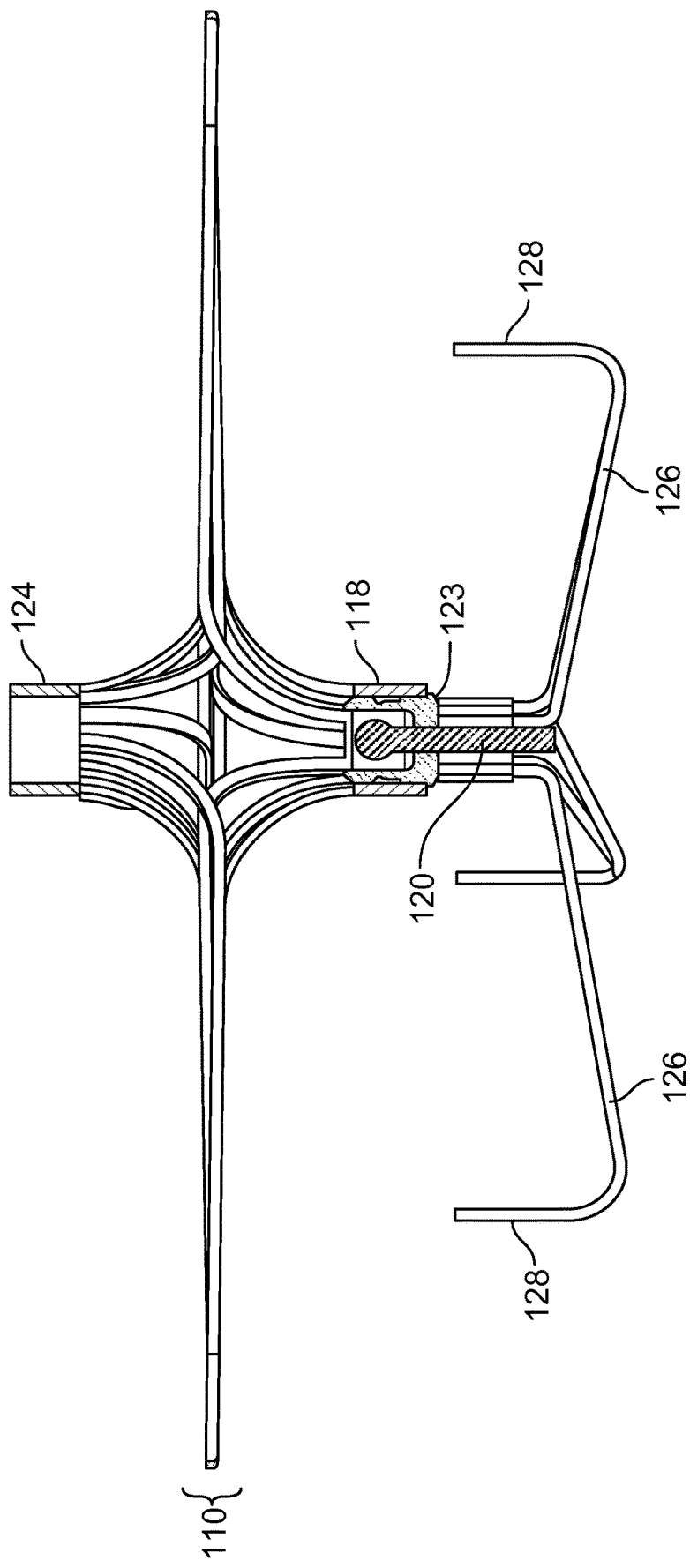
FIG. 3 is side view of the example device frame of FIG. 1.
Figure 4A:
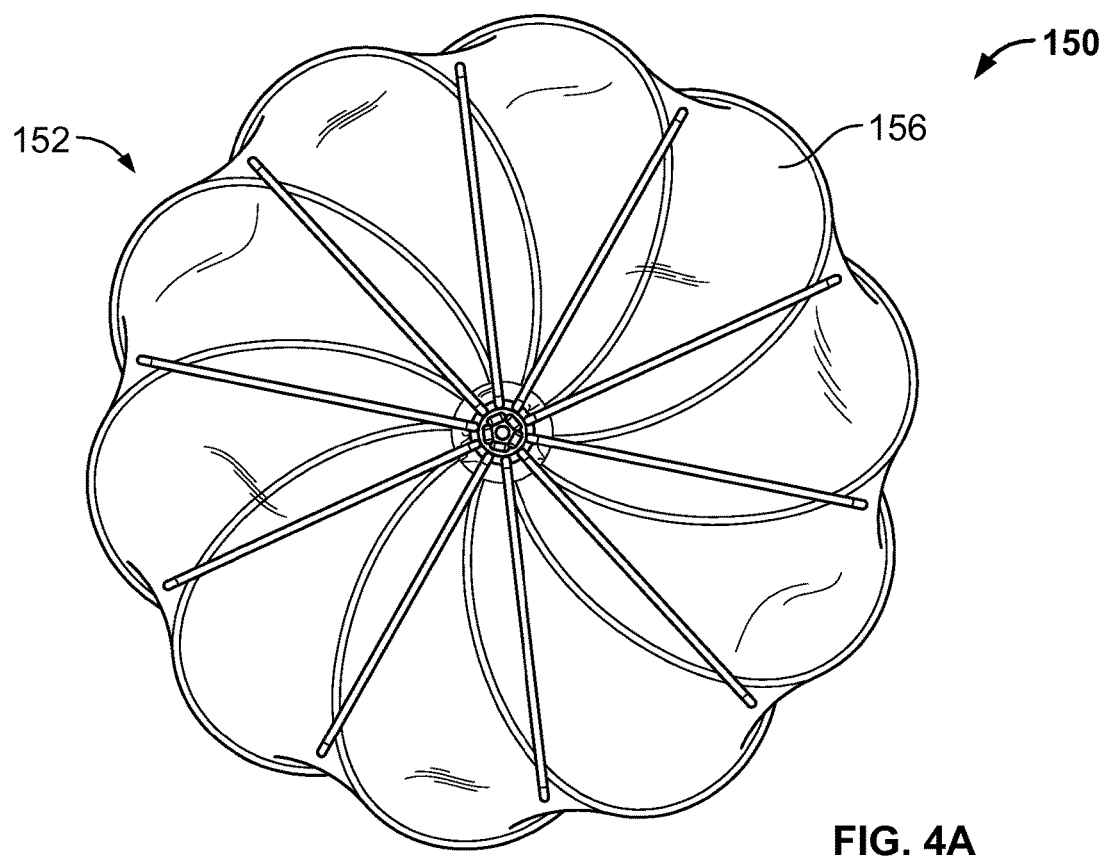
FIG. 4A is a back view of the of an example occlusive device.
Figure 4B:
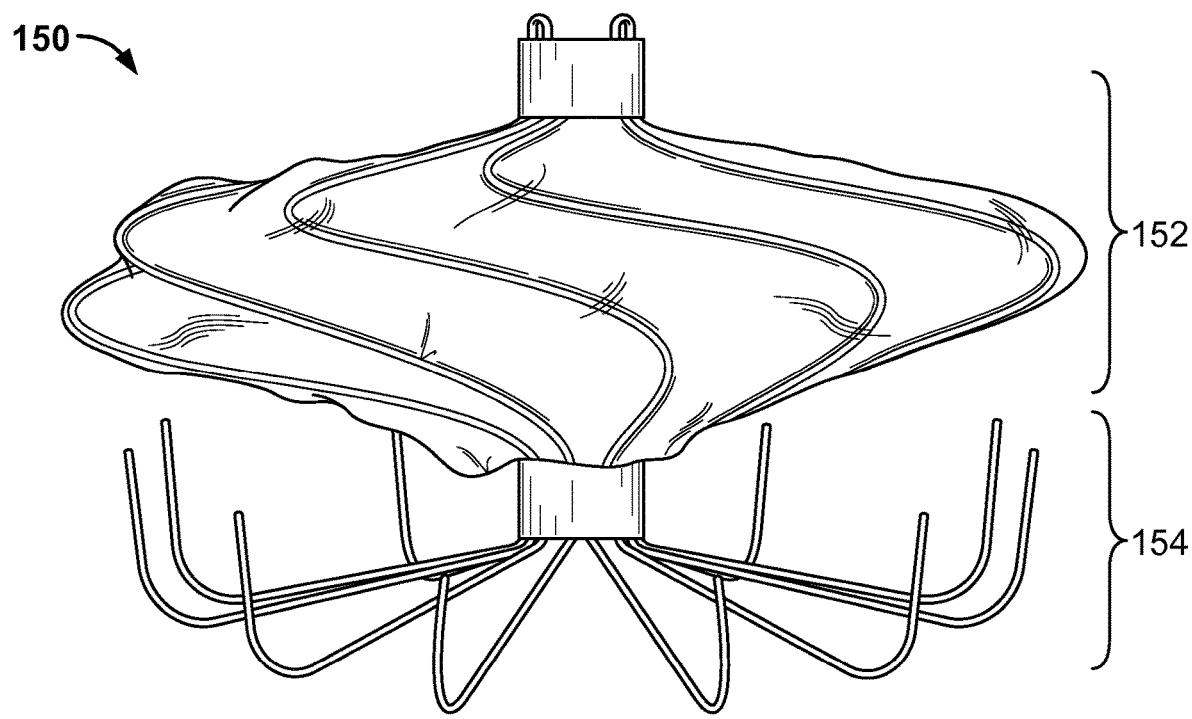
FIG. 4B is a side view of the example occlusive device of FIG. 4A.

FIG. 4A is a front view, and FIG. 4B is a perspective view, of an example occlusive device 150. The device 150 includes an occlusion frame 152 that is similar to the occlusion frame 102, discussed above with reference to FIGS. 1-3, but occlusion frame 152 includes ten elongate frame members rather than twelve. The device 150 includes an anchor frame 154 that is similar to the anchor frame 104, discussed above with reference to FIGS. 1-3, but anchor frame 154 includes ten elongate anchor members rather than five.

The device 150 includes a covering component 156 that covers the occlusion frame 152. In this example, the covering component 156 covers the occlusion frame 152 and is attached to portions of the elongate frame members. In some embodiments, the covering component 156 is attached to at least some portions of the elongate frame members using an adhesive. In some embodiments, FEP (fluorinated ethylene propylene) is used as an adhesive to attach the covering component 156 to elongate frame members. For example, an FEP coating can be applied to portions of the elongate frame members, and the FEP can act as a bonding agent to adhere the covering component 156 to the elongate frame members. In some embodiments, a radiopaque material can be combined with the adhesive that is used to attach the covering component 156 to the elongate frame members. For example, in some embodiments a radiopaque powder (e.g., tungsten powder) can be mixed with the adhesive. When such a radiopaque material is used in conjunction with the adhesive for attaching the covering component 156 to the elongate frame members, the occlusive device 150 (and other devices described herein that include such radiopaque material) can be enhanced from a radiographic visualization standpoint (e.g., using fluoroscopy).

In some embodiments, portions of the covering component 156 can be attached to the elongate members by banding the covering component 156 thereto. For example, in some embodiments portions of the covering component 156, such as but not limited to the ends of the covering component 156, are attached to the elongate members, or to the hub members, using banding. The banding can be a variety of materials, including but not limited to biocompatible film materials, suture materials, metallic materials, and the like, and combinations thereof. Such attachment materials and techniques can also be used for other embodiments of the occlusive devices provided herein.

In some embodiments, the covering component 156 is attached to selected regions of the occlusion frame 152 (and other portions such as the anchor frame 154) and not attached to other regions of the occlusion frame 152. This technique can facilitate enhanced conformability of the occlusive device 150 to the topography of a patient's anatomy at the implant site. Such techniques can also be used with other embodiments of the occlusive devices provided herein.

The covering component 156 is configured to modulate, and in some examples, filter or substantially modulate or inhibit the passage of blood and/or thrombus through the covering component 156. Some embodiments provide a covering component that is configured to induce rapid tissue ingrowth and immediately occludes the passage of blood and/or thrombus through the covering component. The covering component 156 may be a porous, elastic member that can stretch and collapse to accommodate extension and collapse, respectively, of the elongate frame members. Pores of the covering component 156 may be sized to substantially, or in some examples completely, prevent passage of blood, other bodily fluids, thrombi, and emboli. In some implementations, the covering component 156 prevents or substantially prevents passage of blood, other bodily fluids, thrombi, emboli, or other bodily materials through the covering component 156. The covering component 156 can have a microporous structure that provides a tissue ingrowth scaffold for durable occlusion and supplemental anchoring strength of the occlusion device 150. Some embodiments of the covering component 156 comprise a fluoropolymer, such as an expanded polytetrafluoroethylene (ePTFE) polymer. In some embodiments, the covering component 156 can be a membranous covering. In some embodiments, the covering component 156 can be a film. In some embodiments, the covering component 156 can be a filtering medium.

In some embodiments, the covering component 156 is configured such that the modulation of fluid passage through the covering component 156 is immediate and does not rely on a thrombotic process. In some embodiments, the covering component 156 can be modified by one or more chemical or physical processes that enhance certain physical properties of the covering component 156. For example, a hydrophilic coating may be applied to the covering component 156 to improve the wettability and echo translucency of the covering component 156. In some embodiments, the covering component 156 may be modified with chemical moieties that promote one or more of endothelial cell attachment, endothelial cell migration, endothelial cell proliferation, and resistance to thrombosis. In some embodiments, the covering component 156 may be modified with covalently attached heparin or impregnated with one or more drug substances that are released in situ to promote wound healing or reduce tissue inflammation. In some embodiments, the drug may be a corticosteroid, a human growth factor, an anti-mitotic agent, an antithrombotic agent, or dexamethasone sodium phosphate.

In some embodiments, covering component 156 is pre-perforated to modulate fluid flow through the covering component, to create filtering properties, and/or to affect the propensity for tissue ingrowth to the covering component 156. In some embodiments, the covering component 156 is treated to make the covering component 156 stiffer or to add surface texture. For example, in some embodiments the covering component 156 is treated with FEP powder to provide a stiffened covering component 156 or roughened surface on the covering component 156. In some embodiments, selected portions of the covering component 156 are so treated, while other portions of the covering component 156 are not so treated. Other covering component 156 material treatment techniques can also be employed to provide beneficial mechanical properties and tissue response interactions. Such materials and techniques can be used for any of the occlusive devices provided herein.

In some embodiments, the covering component 156 may be formed of a fluoropolymer (e.g., expanded PTFE (ePTFE) or PTFE). In some embodiments, the covering component 156 may be formed of a polyester, a silicone, a urethane, or another biocompatible polymer, or combinations thereof. In some embodiments, bioresorbable or bioabsorbable materials may be used, for example a bioresorbable or bioabsorbable polymer. In some embodiments, the covering component 156 can comprise Dacron. In some embodiments, the covering component 156 can comprise knits or fibers. The covering component 156 may be woven or non-woven in various embodiments. In some embodiments, the covering component 156 may be formed of a copolymer. In some examples, a first portion of the covering component 156 may be formed of a first material and a second portion of the covering component 156 may be formed of a second material. For example, the portion of the covering component 156 that covers the occlusion frame of the device may be formed of a first material, and a portion of the covering component 156 that covers an anchor frame of the device may be formed of a second material.

Referring again to FIG. 1, the anchor frame 104 is referred to as being distal of the occlusion frame 102 because, after deployment, the position of the anchor frame 104 is generally distal of the occlusion frame 102 with respect to the delivery system. By contrast, the occlusion frame 102 is referred to as being proximal of the anchor frame 104 because its deployed position is generally proximal to the delivery system as compared to anchor frame 104. In some examples, the anchor frame 104 is deployed first from the delivery sheath, and the occlusion frame 102 is deployed thereafter from the delivery sheath. With respect to a LAA, following deployment of the device, the anchor frame 104 may be generally deeper within the interior of the LAA, while the occlusion frame 102 and the generally disc-shaped member 110 may be oriented to face the left atrial chamber of the heart.

In the examples described thus far, the elongate frame members of the occlusion frame have been portions of a tube, but in other examples the elongate frame members are wires. Similarly, while the anchor members of the anchor frame described thus far have comprised wires, in some examples the anchor members can be formed from a tube (e.g., either from the same tube from which the occlusion frame is formed, or from a separate, second tube).

For embodiments where one or both of the occlusion frame and/or the anchor frame include elongate members that are wires, such wires may be, for example, spring wires, shape memory alloy wires, or super-elastic alloy wires for self-expanding devices. The elongate members can be made of nitinol (NiTi), L605 steel, stainless steel, or any other appropriate biocompatible material. In some embodiments, drawn wire tubes such as Nitinol tubes with a platinum, tantalum, iridium, palladium, or the like, fill can be used. In some embodiments, bioresorbable or bioabsorbable materials may be used, for example a bioresorbable or bioabsorbable polymer. The super-elastic properties of NiTi make it a particularly good candidate material for the elongate members (e.g., NiTi wires can be heat-set into a desired shape), according to some implementations. NiTi can be heat-set so that an elongate member can self-expand into a desired shape when the elongate member is placed in a less restrictive environment, such as when it is deployed from the delivery sheath to a body cavity. The elongate members can provide structure and shape for the respective frame, and for the device in general. In general, the devices described herein include elongate members that are shaped as desired to suit the purpose of the device. The elongate members may generally be conformable, fatigue resistant, and elastic such that the elongate members have a stored length. The elongate members may have a spring nature that allows them to collapse and elongate to a pre-formed shape (e.g., the frame of a device may have a pre-formed shape).

In some embodiments, the diameter or thickness of the elongate members may be within a range of about 0.008" to about 0.015", or about 0.009" to about 0.030", but in other embodiments elongate members having smaller or larger diameters or thicknesses may be used. In some embodiments, each of the elongate members has the same diameter. In some embodiments, one or more portions of the elongate members may be diametrically tapered. The elongate members may have a round cross-sectional shape or may have a cross-sectional shape that is not round, such as a rectangle or other polygon. Examples of other cross-sectional shapes that the elongate members may have include a square, oval, rectangle, triangle, D-shape, trapezoid, or irregular cross-sectional shape formed by a braided or stranded construct. In some embodiments, an occlusion device may include flat elongate members. In some examples, the elongate members may be formed using a centerless grind technique, such that the diameter of the elongate members varies along the length of the elongate members.

As described above, the devices discussed herein may assume a collapsed configuration, in which the occlusion frame and anchor frame of the device may be elongated so that the device assumes a low crossing profile for positioning within a delivery sheath. In some examples, the elongate frame members and anchor members are caused to collapse or elongate as the device is pulled into the delivery sheath. The sheath may provide a constraining environment and may maintain the device in the delivery configuration while the device is located within the sheath. The device may be configured to self-expand as a result of a bias or shape-memory property of the elongate members, where the device may self-expand upon liberation from the constraining environment, as by exiting the delivery sheath.

Figure 5:
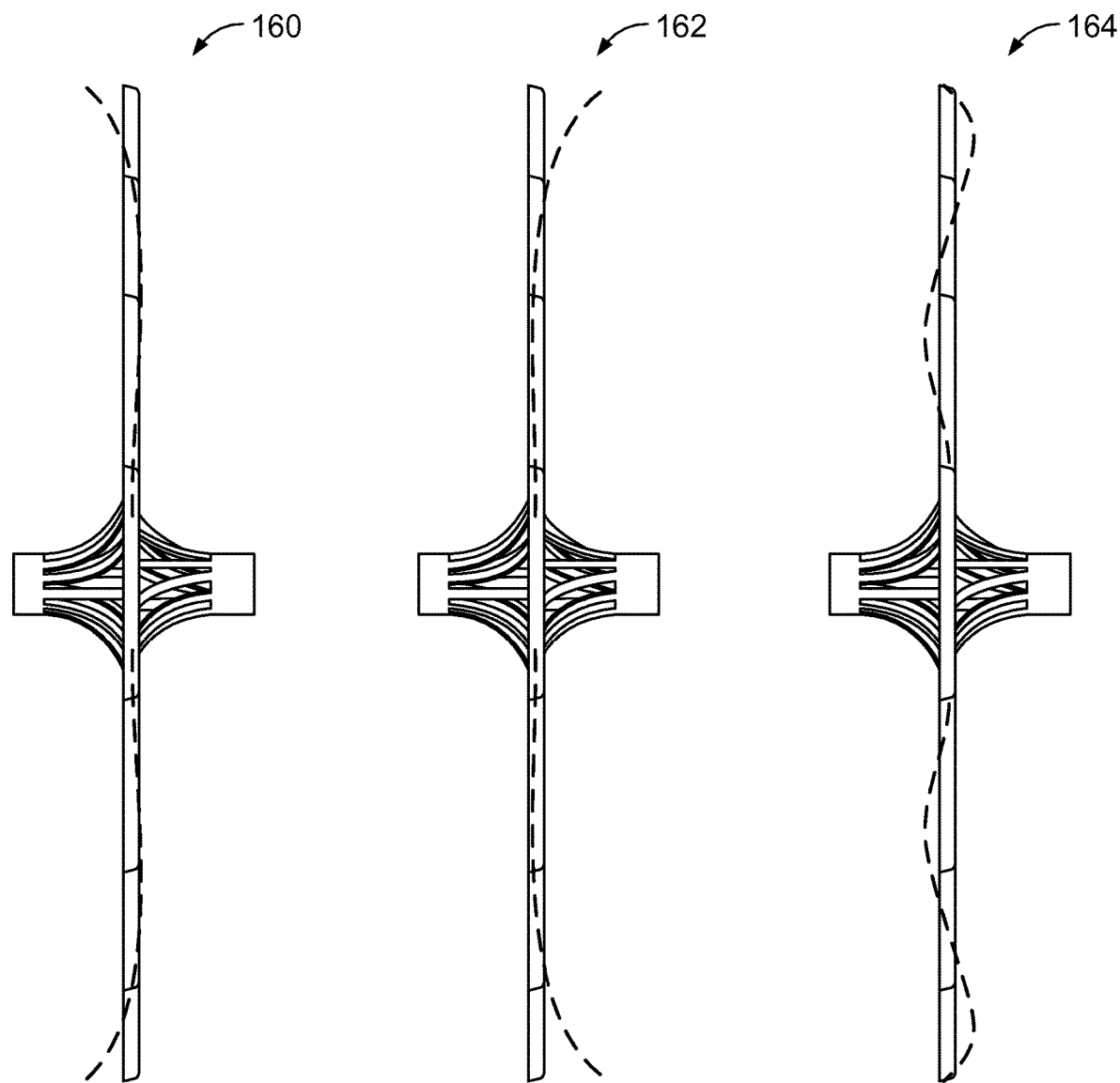
FIG. 5 is a side view of example disc-shaped members having various profiles.

FIG. 5 shows that, in contrast to the generally flat disc-shaped member 110 of FIG. 3, the disc-shaped member can have different shape profiles. For example, the disc-shaped member can have a proximally oriented concave profile 160, a distally oriented concave profile 162, or an "S" shaped profile, where the edge portion of the disc is generally proximally oriented concave. Another alternative (not shown), is an "S" shaped profile, where the edge portion of the disc is generally distally oriented concave. In addition, in some embodiments (e.g., refer to FIGS. 4B, 6A, 7A, 8B, 9A, 10, 11, etc.) the disc-shaped member has a bulbous shape rather than being generally planar. Such bulbous-shaped disc-shaped members can be used with any of the occlusive devices provided herein.

Figure 6B:
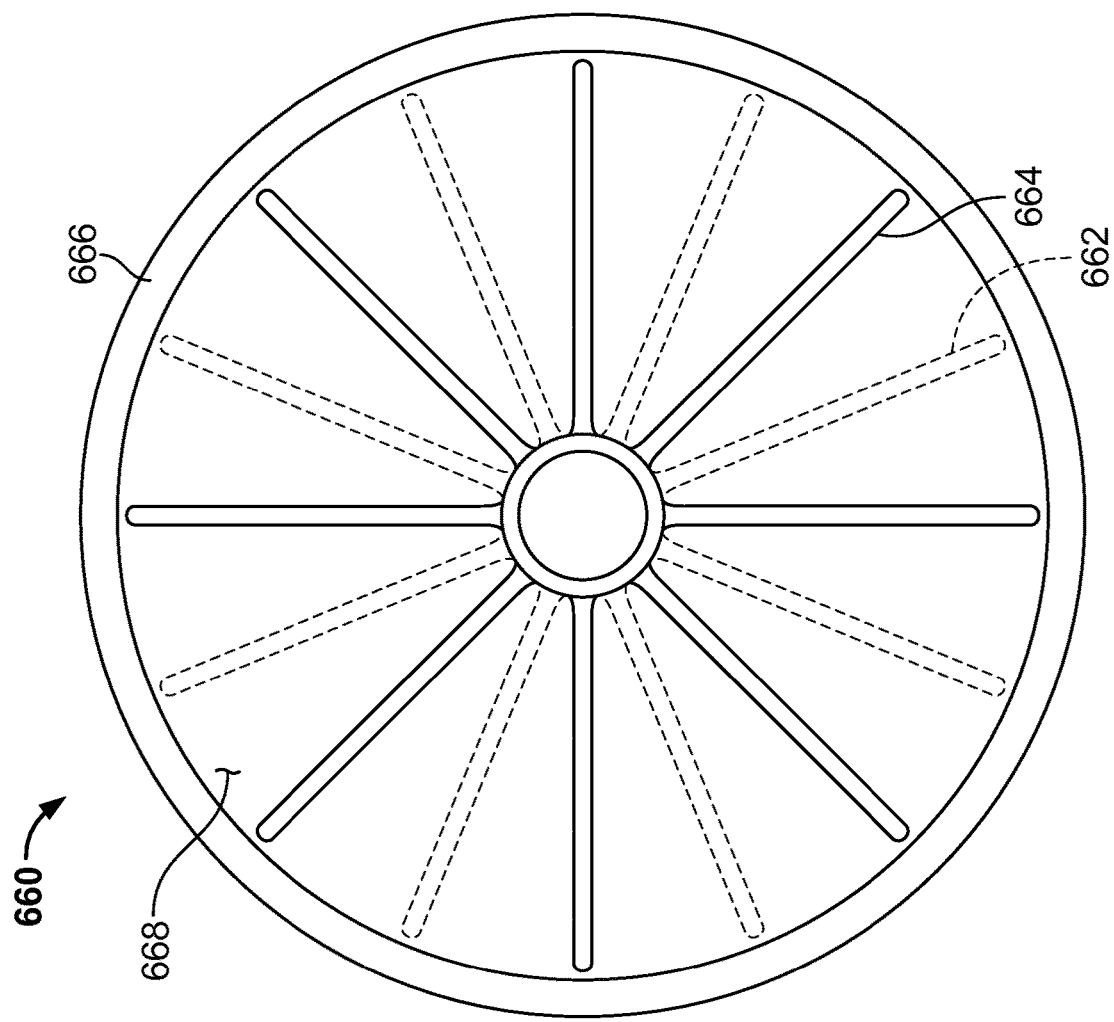
FIG. 6B is an end view of the disc-shaped member of FIG. 6A.
Figure 6A:
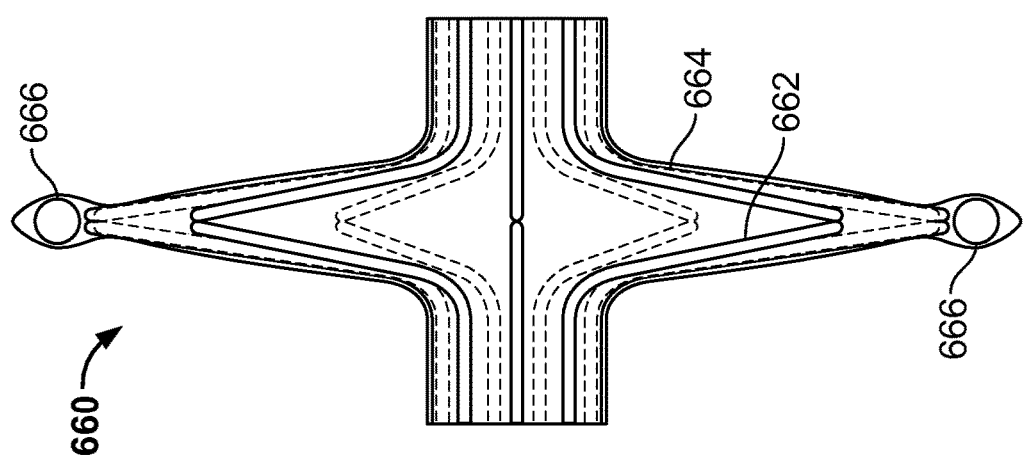
FIG. 6A is a side view of another example disc-shaped member that can be used with occlusive devices provided herein.

FIGS. 6A and 6B show another example embodiment of a disc-shaped member 660 that is used with embodiments of the occlusive devices provided herein. The disc-shaped member 660 includes a first frame portion 662, a second frame portion 664, a peripheral member 666, and a covering 668. The peripheral member 666 is disposed at the generally circular peripheries of the first and second frame portions 662 and 664. The covering 668 is disposed on top of the first and second frame portions 662 and 664 and the peripheral member 666.

The first and second frame portions 662 and 664 each include a center hub and multiple spoke members that project radially from the center hub. The first and second frame portions 662 and 664 can be made of any of the frame materials described elsewhere herein. In some embodiments, the first and second frame portions 662 and 664 have the same design configuration, but in some embodiments the first and second frame portions 662 and 664 have different design configurations. In the depicted embodiment, each frame portion 662 and 664 has the same design configuration with a center hub and eight spoke members. When the first and second frame portions 662 and 664 are assembled into disc-shaped member 660, the first frame portion 662 is simply flipped 180 degrees in relation to the second frame portion 664, so that the first frame portion 662 is the mirror image of the second frame portion 664. In addition, in the depicted embodiment the first frame portion 662 is rotated about 22.5 degrees so that the spoke members of the first and second frame portions 662 and 664 are offset from each other. In some disc-shaped member embodiments that are configured similar to disc-shaped member 660, different numbers of spoke members are included, such as two, three, four, five, six, seven, nine, ten, eleven, twelve, or more than twelve spoke members. The first and second frame portions 662 and 664 can be made of any of the materials of elongate members described elsewhere herein.

The peripheral member 666 is generally circumferentially disposed around the periphery of the disc-shaped member 660. In some embodiments, the peripheral member 666 is disposed near to and may be in contact with the ends (e.g., tips) of the spoke members of the first and second hubs 662 and 664, however the peripheral member 666 is independent of the spoke members. In some embodiments, the peripheral member 666 is a compliant outer rim cording of the disc-shaped device 660. The peripheral member 666 can be made from materials including, but not limited to, elastic polymeric material such as silicone, polyurethane, and the like, or metallic wire such as NiTi wire including stranded NiTi wire or solid NiTi wire. In some embodiments, the peripheral member 666 is attached to the covering 668. For example, the peripheral member 666 may be sewn, adhered, clipped, and the like, to the covering 668. In some embodiments, the peripheral member 666 is sandwiched between portions of the covering 668 that are attached together to provide a result that is akin to upholstery piping trim.

The first and second frame portions 662 and 664, and the peripheral member 666, can be structurally held in place by the covering 668 to form the disc-shaped member 660. The covering 668 can be made of any of the covering materials described elsewhere herein.

The disc-shaped member 660 can be axially elongated to a low-profile configuration for placement within the lumen of a delivery sheath. In the low-profile configuration, the spoke members of the first and second frame portions 662 and 664 can fold about 90 degrees to become general parallel with the central axis of the disc-shaped member 660. The peripheral member 666 can be elongated axially to become generally parallel with the central axis of the disc-shaped member while remaining configured as a loop. Upon deployment from the delivery sheath, the disc-shaped member 660 can radially expand and axially contract to assume the expanded configuration shown.

FIGS. 7A and 7B show another example embodiment of a disc-shaped member 670 that is used with embodiments of the occlusive devices provided herein. The disc-shaped member 670 includes a first frame portion 672, a second frame portion 674, and a covering 678. Optionally, the disc-shaped member 670 may also include a peripheral member (not shown) like the peripheral member 666 described above.

The first and second frame portions 672 and 674 have petal-shaped spokes that project generally radially from the center hubs of the first and second frame portions 672 and 674. In this embodiment, each of the first and second frame portions 672 and 674 has five petal-shaped spokes, but in other embodiments other numbers of petal-shaped spokes are included, such as two, three, four, six, seven, eight, nine, ten, or more than ten petal-shaped spokes. The first and second frame portions 672 and 674 can be made of any of the materials of elongate members described elsewhere herein.

The widths of the petal-shaped spokes can be selected as desired. While in some embodiments all the petal-shaped spokes have the same width, in some embodiments the petal-shaped spokes have two or more different widths. Embodiments having fewer numbers of petal-shaped spokes may have wider petal-shaped hubs, and embodiments having greater numbers of petal-shaped spokes may have narrower petal shaped spokes, but such a design convention is not required. In some embodiments, adjacent petal-shaped spokes of the first and second frame portions 672 and 674 are spaced apart from each other (as shown), but it some embodiments adjacent petal-shaped spokes overlap each other. While in some embodiments petal-shaped spokes overlap only adjacent spokes, in some embodiments petal-shaped spokes overlap adjacent and non-adjacent petal-shaped spokes.

As described above in regard to disc-shaped member 660, in some embodiments the first and second frame portions 672 and 674 of disc-shaped member 670 have the same design configuration (as shown), but the frame portions can have dissimilar design configurations in other embodiments. In an example embodiment having five spokes, the first frame portion 672 is flipped 180 degrees in relation to the second frame portion 674 and rotated about 36 degrees so that the petal-shaped spokes of the first and second frame portions 672 and 674 are off-set from each other.

The disc-shaped member 670 includes a covering 668 that can be made of any of the covering materials and include any of the covering material treatments described elsewhere herein. In some embodiments, the first and second frame portions 672 and 674 can be attached to the covering 668 using any of the techniques described elsewhere herein, including but not limited to, sewing, adhering, clipping, sandwiching the frame portions 672 and 674 between multiple layers of covering 668, and so on. In some embodiments of disc-shaped member 670, the petal-shaped spokes are at least partially individually covered with covering 668. For example, in embodiments that have overlapping adjacent petal-shaped spokes, each spoke may be generally individually covered with covering 668. Such a configuration may provide a disc-shaped member 670 that is significantly conformable to the anatomy where the member 670 is deployed. In some embodiments, the covering 668 may generally cover the first and second frame portions 672 and 674 as a whole. In some embodiments, the covering 668 may cover the petal-shaped spokes individually. In some embodiments, a combination of individual coverings and covering as a whole may be combined on a disc-shaped member.

Figure 8A:
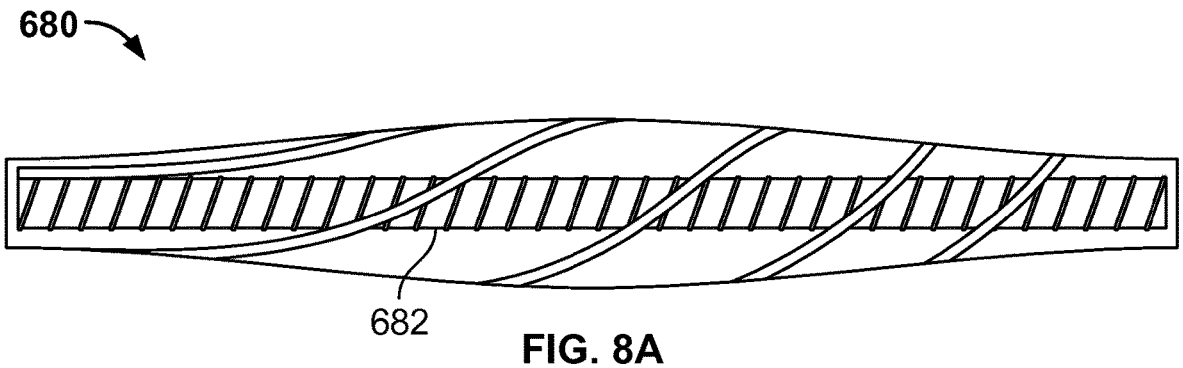
FIG. 8A is another example disc-shaped member, shown in a collapsed configuration, that can be used with occlusive devices provided herein.
Figure 8B:
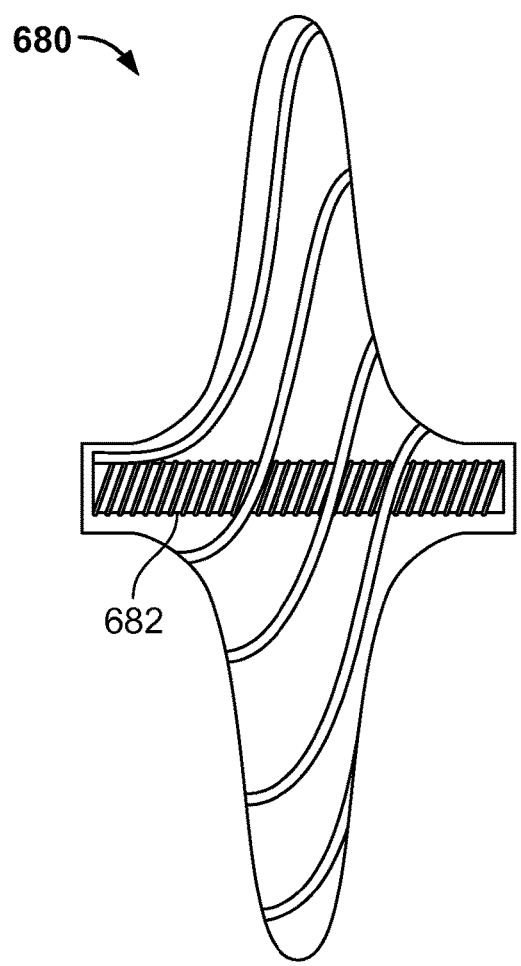
FIG. 8B is a side view of the example disc-shaped member of FIG. 8A shown in an expanded configuration.

FIGS. 8A and 8B show another example embodiment of a disc-shaped member 680. The disc-shaped member 680 includes an elastic member 682. In some embodiments, the elastic member 682 connects the proximal and distal hubs of the disc-shaped member 680. In some embodiments, the proximal and distal hubs may be eyelets, tubes, rings, crimp collars, and the like.

The disc-shaped member 680 is shown in a collapsed low-profile configuration in FIG. 8A. This configuration can be used, for example, while the disc-shaped member 680 is contained within a delivery sheath or catheter used to deliver the occlusive device of which disc-shaped member 680 is a part. The disc-shaped member 680 is shown in an expanded configuration in FIG. 8B. This is the configuration that the disc-shaped member 680 will seek when the restraints of a delivery sheath are removed from the disc-shaped member 680, such as when the disc-shaped member 680 emerges from the delivery sheath during a transcatheter implant procedure.

The elastic member 682 may be optionally included on any the disc-shaped member embodiments provided herein. In some disc-shaped member embodiments, the elastic member 682 can cause, or encourage, the disc-shaped member to expand to the deployed configuration as depicted by disc-shaped member 680 in FIG. 8B. In some embodiments, the elastic member 682 acts as an inner shaft and radial filler when the disc-shaped member 680 is in the low-profile configuration. In some embodiments, the elastic member 682 enhances axial alignment between the hubs of the disc-shaped member 680, and reduces the likelihood of the elongate members becoming engaged with each other when the disc-shaped member 680 is in the low-profile configuration within a delivery sheath. Keeping the individual elongate members spaced away and not interfering with each other inside the sheath will facilitate proper expansion of the frame when the disc-shaped member 680 is deployed from the delivery sheath. The elastic member 682 can also provide a tensile force property to encourage the hubs of the disc-shaped member 680 to move towards each other during deployment to reach the intended expanded shape in situ. The elastic member 682 can be made from a biocompatible elastic material such as silicone, another suitable elastomeric thermoplastic, or a polymer.

Figure 9B:
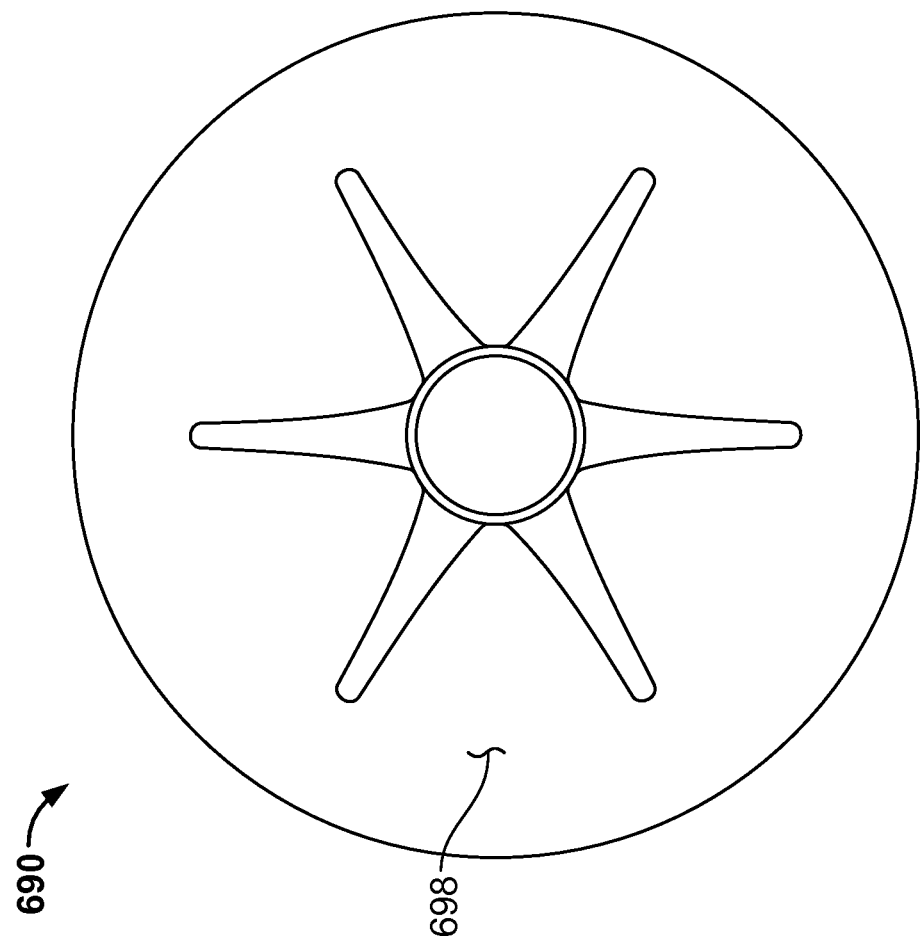
FIG. 9B is an end view of the disc-shaped member of FIG. 9A.
Figure 9A:
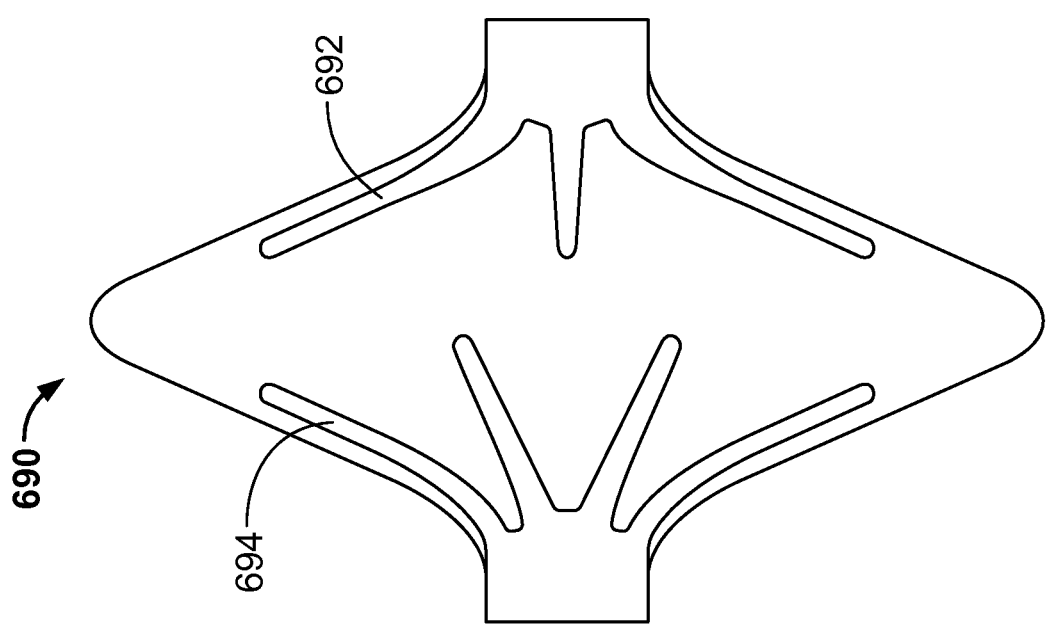
FIG. 9A is a side view of another example disc-shaped member that can be used with occlusive devices provided herein.

FIGS. 9A and 9B show another example embodiment of a disc-shaped member 690 that is used with some embodiments of the occlusive devices provided herein. The disc-shaped member 690 includes a first frame portion 692, a second frame portion 694, and a covering 698. Optionally, the disc-shaped member 690 may also include a perimeter member (not shown) like the peripheral member 666 described above, and/or an elastic member (not shown) like the elastic member 682 described above.

The first and second frame portions 692 and 694 can have any of the spoke configurations of the disc-shaped members described elsewhere herein. For example, in some embodiments the first and second frame portions 692 and 694 have petal-shaped spokes that project generally radially from the center hubs of the first and second frame portions 692 and 694. In some embodiments, the first and second frame portions 692 and 694 may have spokes that are made of individual elongate members. As described above in regard to disc-shaped member 660, in some embodiments the first and second frame portions 692 and 694 of disc-shaped member 690 have the same design configuration (as shown), but the frame portions can have dissimilar design configurations in other embodiments. In some embodiments having six spokes, the first frame portion 692 is flipped 180 degrees in relation to the second frame portion 694 and rotated about 30 degrees so that the petal-shaped spokes of the first and second frame portions 692 and 694 are off-set from each other. But in some embodiments of disc-shaped members, no such offsetting of the spokes is used. In the depicted embodiment, each of the first and second frame portions 692 and 694 has six narrow petal-shaped spokes, but in other embodiments other numbers of spokes are included, such as two, three, four, five, seven, eight, nine, ten, or more than ten spokes. The first and second frame portions 692 and 694 can be made of any of the materials of elongate members described elsewhere herein.

The disc-shaped member 690 includes a covering 698 that can be made of any of the covering materials described herein and include any of the covering material treatments described elsewhere herein. In some embodiments, the covering 698 is a composite material that is semi-rigid. For example, in some embodiments multiple layers of materials are sandwiched together with FEP bonding therebetween, to increase the rigidity of the covering 668. In some embodiments, the spokes of the first and second frame portions 692 and 694 are also sandwiched between the layers of covering material. In some embodiments, the first and second frame portions 692 and 694 are attached to the covering 698 using any of the techniques described elsewhere herein, including but not limited to, sewing, adhering, clipping, and the like.

In some embodiments, the free ends of some or all of the spokes of the first and second frame portions 692 and 694 do not extend all the way to the periphery of the disc-shaped member 690 (as shown). Such a configuration may provide a disc-shaped member 690 that is significantly conformable to the anatomy where the member 690 is deployed, and the semi-rigid nature of the covering 698 may help facilitate the conformance. In some embodiments, the spokes extend substantially all the way to the periphery of the disc-shaped member 690.

Figure 10:
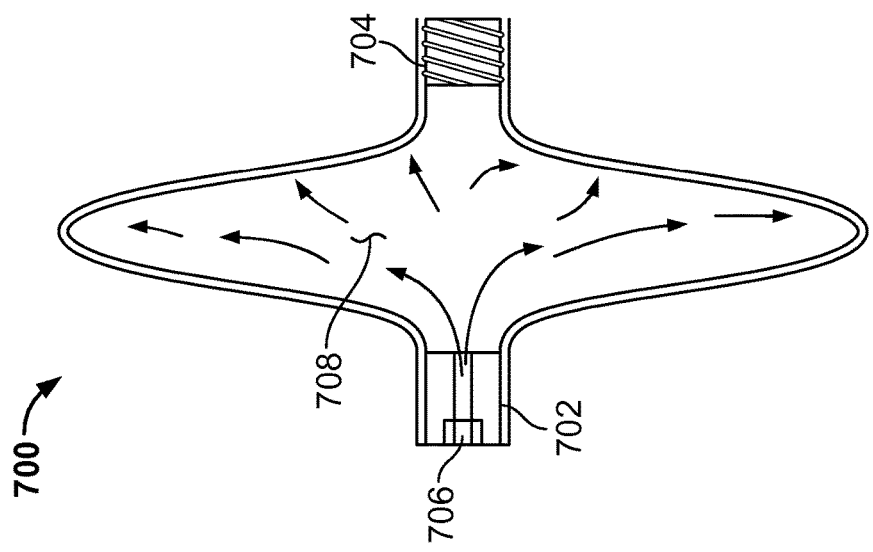
FIG. 10 is a side view of another example disc-shaped member that can be used with occlusive devices provided herein.

FIG. 10 shows another example embodiment of a disc-shaped member 700 that is used with some embodiments of the occlusive devices provided herein. The disc-shaped member 700 includes a first hub 702, a second hub 704, and a covering 708. Optionally, the disc-shaped member 700 may also include a perimeter member (not shown) like the peripheral member 666 described above, an elastic member (not shown) like the elastic member 682 described above, and frame portions with spokes, petals, or struts like any of those embodiments described elsewhere herein.

In some embodiments, the disc-shaped member 700 is expandable (to the general shape shown, or any other desired shape) by inflation of the disc-shaped member 700. During transcatheter deployment, while the disc-shaped member 700 is contained within a delivery sheath in a low-profile configuration, the disc-shaped member 700 is not inflated. Thereafter, when the disc-shaped member 700 has been deployed from the delivery sheath, an inflation medium can be supplied to the disc-shaped member 700 to cause the disc-shaped member to expand.

In some embodiments, the disc-shaped member 700 includes a first hub 702 and a second hub 704. A covering 708 is attached to the first and second hubs 702 and 704. The first hub 702 may include a valve 706. In some embodiments, the valve is a one-way valve that permits an inflation medium to enter the internal compartment defined by the covering 708 while restricting the inflation medium from exiting the internal compartment defined by the covering 708. A typical duckbill-type valve system or an umbrella valve system can be used in some implementations. The valve may be predisposed to be in the closed position, and increased internal pressure may contribute to its sealing efficiency. In some embodiments, the disc-shaped member 700 can be deflated for repositioning or retrieval purposes.

The covering 708 can be formed of one or more of a variety of biocompatible materials and composite materials as described elsewhere herein, including but not limited to densified PTFE or ePTFE, silicone, or an elastomeric fluoropolymer, such as described in one or more of U.S. Pat. Nos. 7,049,380, 7,462,675, and 8,048,440, the contents of which are each incorporated by reference herein.

In some embodiments, the inflation medium supplied to disc-shaped member 700 can include two or more substances. In some embodiments, the inflation medium reacts with, combines with, or interacts with one or more materials included in the disc-shaped member 700 prior to delivery of the inflation medium. For example, an inner surface of the wall of the covering 708 may be pre-imbibed with a first filler reagent substance of a two-part filler system, and an inflation medium that comprises a second reagent substance may be delivered thereto. The second reagent material may activate the first filling reagent material, in some examples. For example, the first filling material may be a calcium-containing solution, and the second material may be an alginate-containing solution. The alginate-containing solution may react with the calcium-containing solution, and they may expand. In some examples, the first and second filling materials may differ in physical phase type. For example, the first filling material may be one of a solid, liquid, or gas (or other type), and the second filling material may be a different one of a solid, liquid or gas (or other type) as compared to the first filling material. In some examples, the filling material comprises at least one of a bioinert material and a biocompatible material. The inflation medium may also include biocompatible liquids, solids, foams, gels, and gases. In some examples, the inflation medium may be a radiopaque liquid. In some embodiments, the inflation medium may be a saline solution. In some embodiments, the inflation medium may include gels and/or foams. As defined herein, the term "gel" refers to any multi-part biocompatible substance that can be activated in situ or be caused to swell or increase in viscosity. As defined herein, the term "foam" refers to any substance that includes entrapped regions of gas. Open-cell foams may be used, for example. An open-cell polyurethane (PU) foam may be used. In some examples, the inflation medium may be a silicone gel. In some embodiments, the inflation medium may be a polyurethane gel. In some embodiments, the inflation medium may be a solid material. For example, in some such embodiments the inflation medium may be a granular solid material, a string-like solid material, or a super-elastic wire material.

Figure 11:
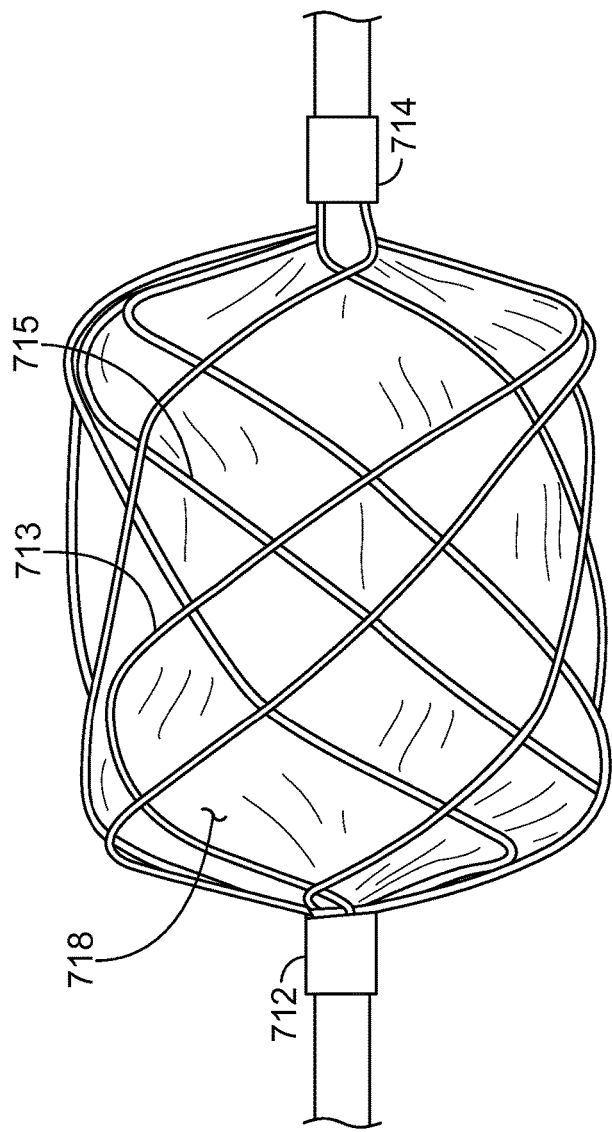
FIG. 11 is a side view of another example disc-shaped member that can be used with occlusive devices provided herein.

FIG. 11 shows another example embodiment of a disc-shaped member 710 that is used with some embodiments of the occlusive devices provided herein. The disc-shaped member 710 is illustrated in an elongated configuration so that the arrangement of the inner and outer frame structures can be readily visualized. The disc-shaped member 710 includes a first nested hub assembly 712, a second nested hub assembly 714, an outer frame structure 713, an inner frame structure 715, and a covering 718. Optionally, the disc-shaped member 710 may also include a perimeter member (not shown) like the peripheral member 666 described above, and/or an elastic member (not shown) like the elastic member 682 described above.

Disc-shaped member 710 includes two elongate member frame structures (the outer and inner frame structures 713 and 715) that are nested within each other. The inner frame structure 715 is nested inside of the outer frame structure 713. In other words, the hubs of the inner frame structure 715 are located within the hubs of the outer frame structure 713 at the first and second nested hub assemblies 712 and 714. Further the elongate members of the inner frame structure 715 (that extend between the hubs of the inner frame structure 715) are located within the elongate members of the outer frame structure 713 (that extend between the hubs of the outer frame structure 713).

In some embodiments, the outer and inner frame structures 713 and 715 include elongate members that follow a spiral pattern between a proximal and distal hub of the outer and inner frame structures 713 and 715. In some embodiments, other types of elongate member frame structures may be included, including, but not limited to, spokes, struts, petals, loops, and so on. In this embodiment, the spiral patterns of the outer and inner frame structure 713 and 715 are not parallel to each other. Rather, in some embodiments the elongate members of the outer and inner frame structures 713 and 715 crisscross each other. For example, in some embodiments, the outer and inner frame structures 713 and 715 are formed to have reversed helical patterns. Such a relative construct of the outer and inner frame structures 713 and 715 may facilitate the frame structures 713 and 715 to expand from a low-profile configuration to an expanded configuration in a balanced manner such that frame malformations, such as twisting ("phone cording"), can be reduced or eliminated.

Figure 12:
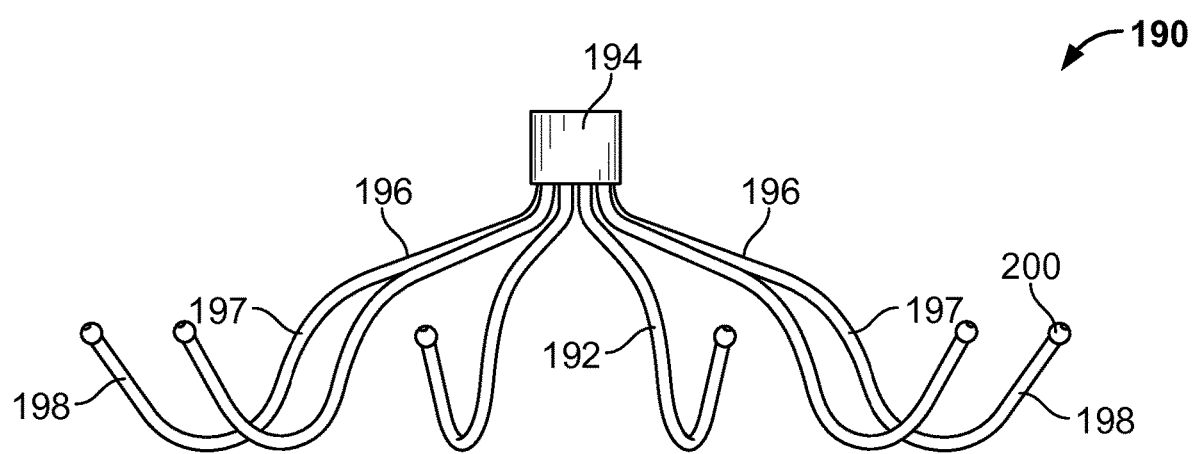
FIG. 12 is a perspective view of an example anchor frame.

FIG. 12 is a perspective view of an example anchor frame 190. Anchor members 192 extend from a second hub component 194. In the example of FIG. 12, the anchor members 192 comprise wires, but in other embodiments, the anchor members can be formed from a tube, as by laser-cutting, to be discussed further below with reference to FIG. 23. The anchor frame 190 includes twelve anchor members 192, but for clarity only six of the twelve anchor members 192 are shown in FIG. 12. In other examples, a different number of anchor members 192 may be used (e.g., two, three, four, five, six, seven, eight, nine, ten, eleven, or more).

First portions 196 of the wires that form the anchor members 192 extend generally distally and radially from the second hub component 194, at an angle that is about 30 degrees distal from a directly radial direction. Second portions 197 of the wires that form the anchor members 192 extend from the first portions 196 in a generally distal and radial direction, at an angle that is about 75 degrees distal from a directly radial direction. Third portions 198 of the wires that form the anchor members 192 extend from the second portions 197 in a generally proximal and radial direction, at an angle that is about 60 degrees proximal from a directly radial direction. As can be seen in FIG. 12, a profile of the anchor frame 190 has the shape of an umbrella or a bell, formed by first and second portions 196 and 197, with a lip formed by third portion 198.

Each of the anchor members 192 includes one or more generally spherically shaped member 200. The generally spherically shaped members 200, (or ball ends) are adapted for atraumatically engaging body tissue and securing the device in place, for example by friction, pressure, or entanglement. In some examples, the ball ends 200 may be formed on the end of the fixation anchor wire by laser welding. The ball ends 200 may provide anchoring and may reduce a potential for perforation or pericardial effusion, in some implementations. In general, the ball ends 200 or other passive anchor features discussed herein may cause less friction on an inside surface of a delivery sheath as compared to some active anchor elements with sharp edges, in some implementations, which may reduce particulation with respect to the delivery system in some cases.

In some embodiments, a diameter of the ball ends 200 may be about two times the diameter of the frame anchor wire. In some examples, the diameter of the ball end 200 may range from about 1× (with just a round wire end) to about 2× the diameter of the frame anchor wire, for example, the diameter may be about 1.5× the diameter of the frame anchor wire, or about 1.6×, 1.7×, 1.8×, or 1.9× the diameter of the frame anchor wire. The ball end may be created by applying a laser pulse to the end of the frame anchor wire, for example. For example, in some embodiments, spherical members or ball ends may be formed directly on ends of the frame anchor wires using a precision laser weld technique (e.g., using an Nd:YAG laser).

The ball ends 200 may serve as anchor points for anchoring devices that include the frame anchor 190 to tissue at a deployment site. The surface of the third portions 198 of anchor members 192 may serve as a landing zone for tissue. Additionally, the surface of the first portions 196 may serve as a landing zone for tissue.

Figure 13:
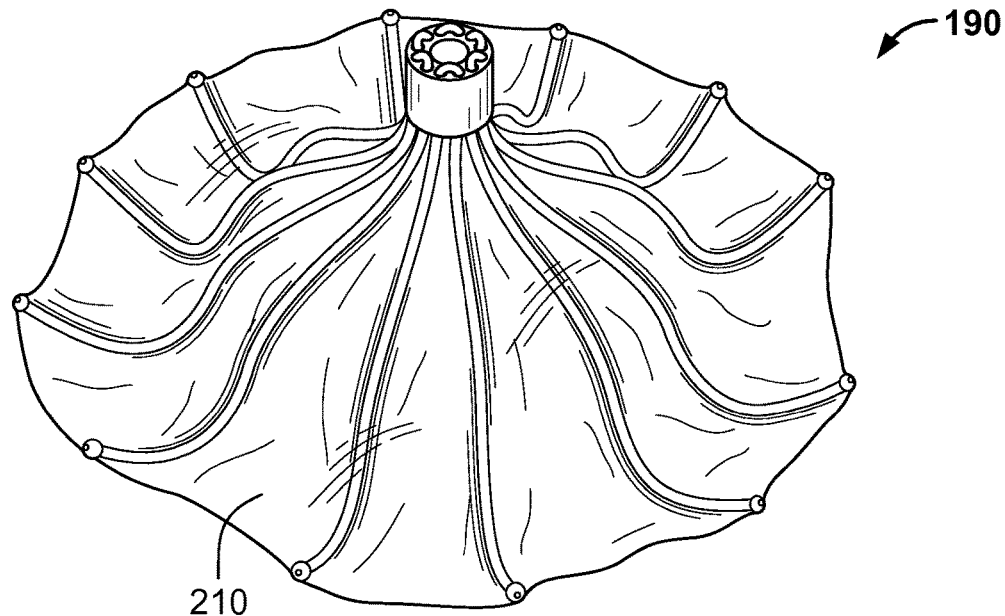
FIG. 13 is a perspective view of the anchor frame of FIGS. 12A and 12B, including an example covering component.

FIG. 13 is a perspective view of the anchor frame 190 of FIGS. 6A and 6B, including a covering component 210 that covers the anchor frame 190. In this example, the covering component 210 covers substantially all of the anchor frame 190, but in other examples the covering component 210 may cover only a portion of the anchor frame 190.

Figure 14:
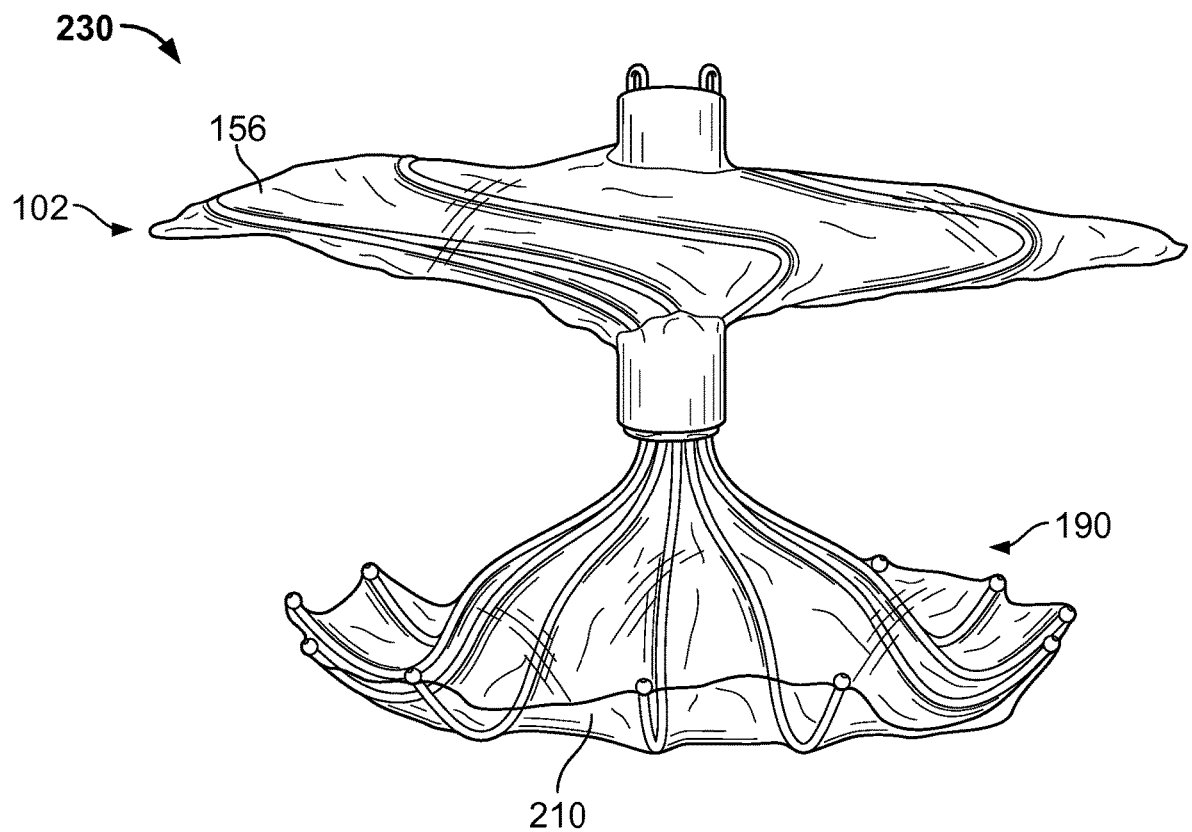
FIG. 14 is a perspective view of an example occlusive device.

FIG. 14 is a perspective view of an example occlusive device 230. Device 230 includes the occlusion frame 102 of FIGS. 1-3 and the anchor frame 190 of FIG. 7. In this example, a first covering component 156 covers the occlusion frame 102, and a second covering component 210 covers the anchor frame 190.

Figure 15:
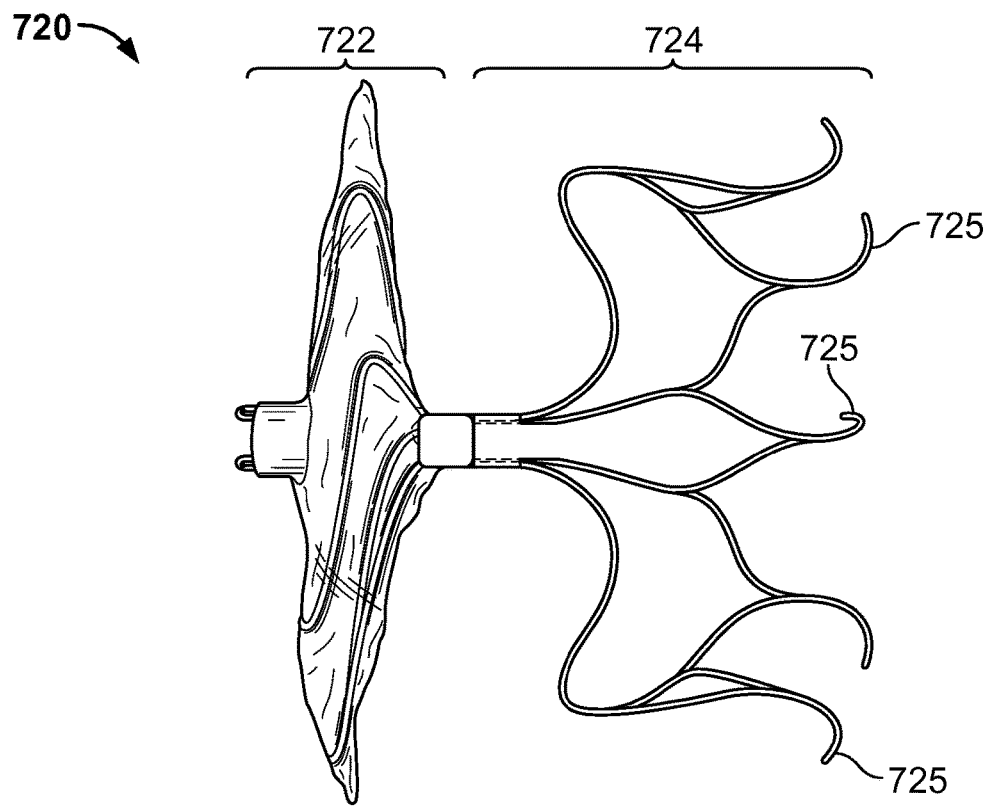
FIG. 15 is a side view of another example occlusive device in accordance with embodiments provided herein.

FIG. 15 is an illustration of another example device 720 that can be used to occlude a hole, defect, aperture, or appendage within a body of a patient. The device 720 includes two sub-frames: an occlusion frame 722 (or disc-shaped member) and an anchor frame 724. While the device frames discussed herein are generally described as including an occlusion frame because the examples are generally described with reference to occlusion applications, for filtering applications where occlusion is not desired, the occlusion frame may be a filter frame. That is, any of the described occlusion frames may also be filter frames, for example. In some embodiments, at least a portion of the occlusion frame 722 is be covered by a covering component (not shown) that is configured to inhibit the passage of blood and/or thrombus through the covering component, i.e., to substantially occlude the flow of blood and/or thrombus through the covering component. In some embodiments, the anchor frame 724 is not covered by the covering component.

In some embodiments, a portion of the anchor frame 724 is covered by the covering component, and in some embodiments the anchor frame 724 is substantially covered by the covering component (or by a second covering component).

In some embodiments, the anchor frame 724 is constructed from material that is cut and expanded. For example, in some embodiments the anchor frame 724 is made from a tube of material that is laser-cut and then expanded (and heat-set in some embodiments) to the configuration substantially as shown. In some embodiments, NiTi is used as the material, but other materials such as stainless steel and polymers may also be used. The design of the anchor frame 724 can facilitate the application of a radial force from the anchor frame 724 to the surrounding tissue that can assist with the anchoring performance of the occlusive device 720. In addition, the configuration of the anchor frame 724 may include one or more portions made of curved elongate members. Such curved portions can provide axial and radial flexibility and springiness whereby the anchor frame is resistant to device migration within the anatomy of the patient. Further, in some embodiments the anchor frame 724 includes multiple free ends 725 that can abut or penetrate tissue to provide anchorage of the occlusive device 720 in relation to the surrounding tissue.

Figure 16A:
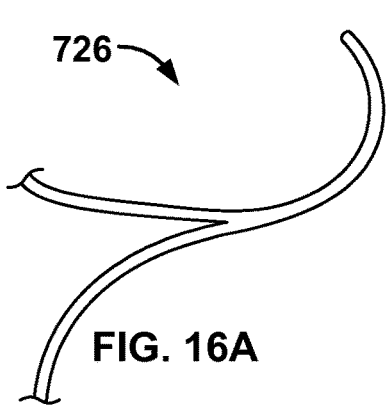
FIGS. 16A-16D are examples of anchor features that can be used with occlusive devices provided herein.
Figure 16B:
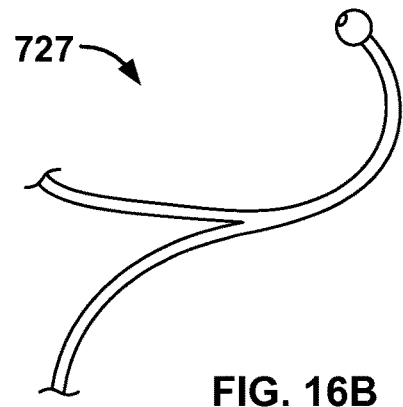
Figure 16C:
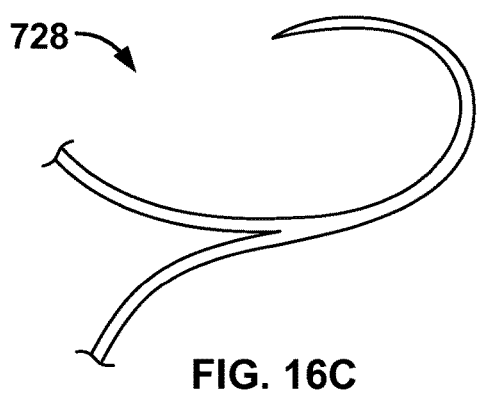
Figure 16D:
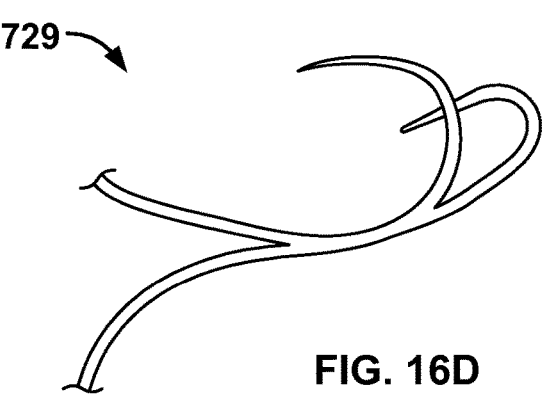

FIGS. 16A through 16D are additional example configurations of anchor frame free ends that can be included with some embodiments of the occlusive devices provided herein. Such anchor frame free ends can facilitate the resilient anchorage of occlusive devices to the tissue of a patient. FIG. 16A illustrates an anchor frame free end 726 that is curved radially outward from the axis of the occlusive device. As such, at least the tip of the anchor frame free end 726 can contact tissue and provide an anchoring function to resist migration of an occlusive device in relation to the tissue that the anchor frame free end 726 is in contact with. FIG. 16B illustrates an anchor frame free end 727 that includes an atraumatic tip. In this example, the atraumatic tip is a ball end that is analogous to ball ends 200 described above. FIG. 16C illustrates an anchor frame free end 728 that is configured to have a sharp tip. In some implementations, such a sharp tip may penetrate tissue to provide anchorage and resistance to migration of the occlusive device of which the anchor frame free end 728 is a part. FIG. 16D illustrates another example anchor frame free end 729. In this embodiment, the anchor frame free end 729 is bifurcated to include two free ends. The two free ends of anchor frame free end 729 are illustrated as sharpened, but in some embodiments the two free ends may have atraumatic ends (e.g., ball ends), or any of the other example anchor frame free ends described herein, or combinations thereof.

Figure 17:
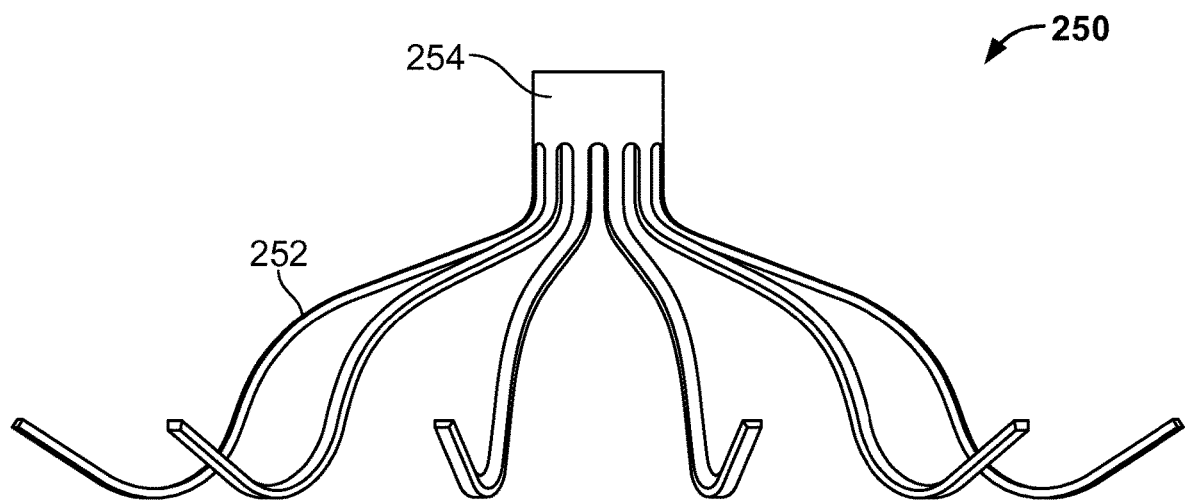
FIG. 17 is a perspective view of an example anchor frame.

FIG. 17 is a perspective view of an example anchor frame 250 that is similar to the anchor frame 190 of FIGS. 12A, 12B, and 13, except that the anchor members 252 are not wires, but rather are elongate members formed by laser-cutting a tube of material, in a similar manner as described above with reference to occlusion frame 102. A second hub component 254 comprises a cylindrical portion of the tube, and the anchor members 252 extend from the second hub component 254. While frame 250 does not include ball end members, in other examples a ball end member similar to ball end 200 could be included, as could other types of anchor features.

Figure 18:
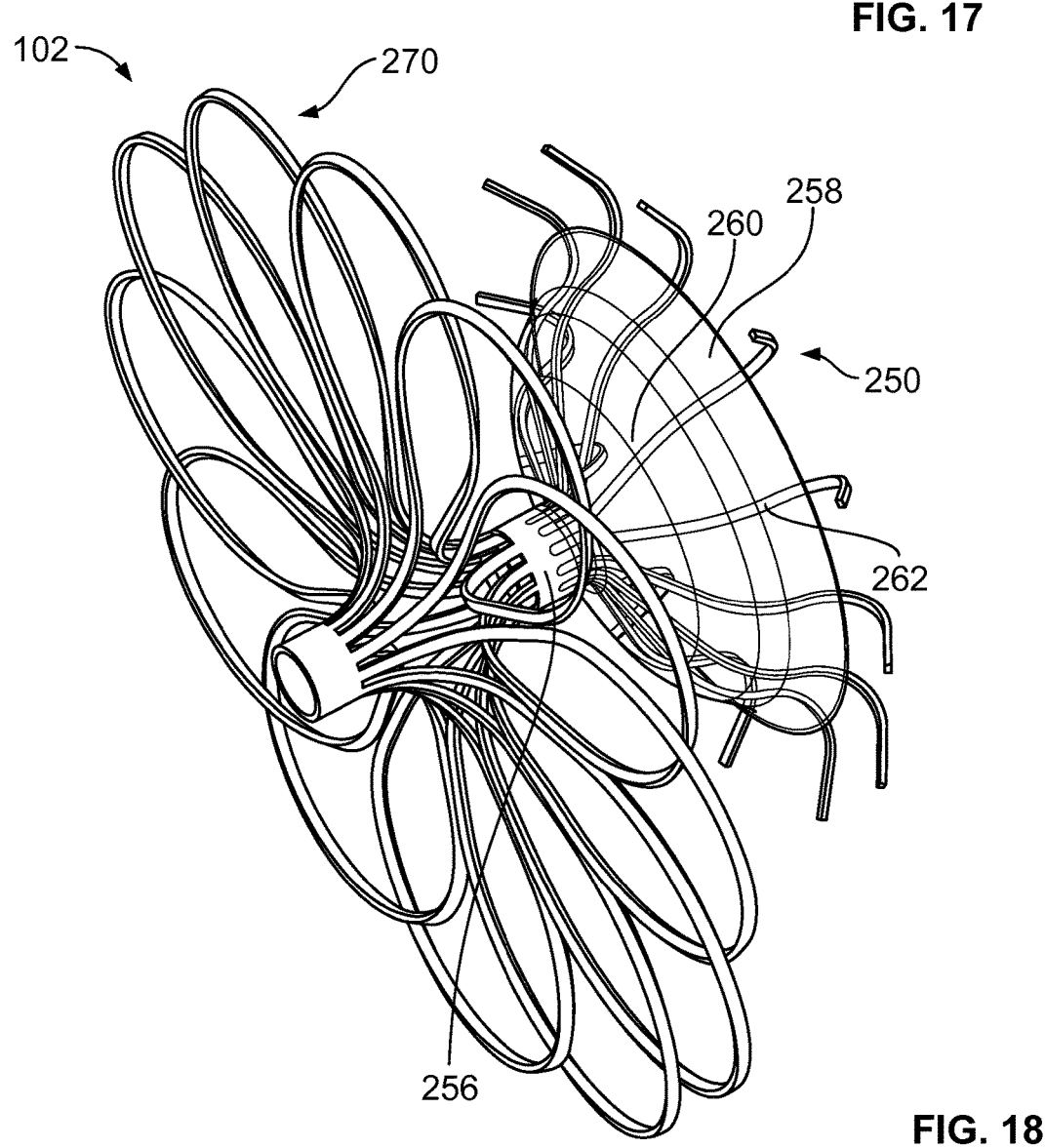
FIG. 18 is a perspective view of another example device frame.

FIG. 18 is a perspective view of another example device frame 270. Device frame 270 includes occlusion frame 102 and anchor frame 250, and is laser-cut from a single tube of material. That is, both occlusion frame 102 and anchor frame 250 are laser-cut from the same tube of material. In this example, the elongate frame members 106 and the anchor members 252 each extend from a first hub component 256. In this example, the anchor frame 250 is only partially covered by a covering component 258. Covering component 258 covers the first hub component 256, the first portions 260 of the elongate members that form the anchor members 252 and a majority of the second portions 262 of the elongate members that form the anchor members 252. In some embodiments, the covering component 258 can act as a pledget in relation to the anchor members 252. In some embodiments, supplemental pledget members can be added to one or more of the anchor members of this embodiment and any other occlusive device embodiment provided herein.

Figure 19A:
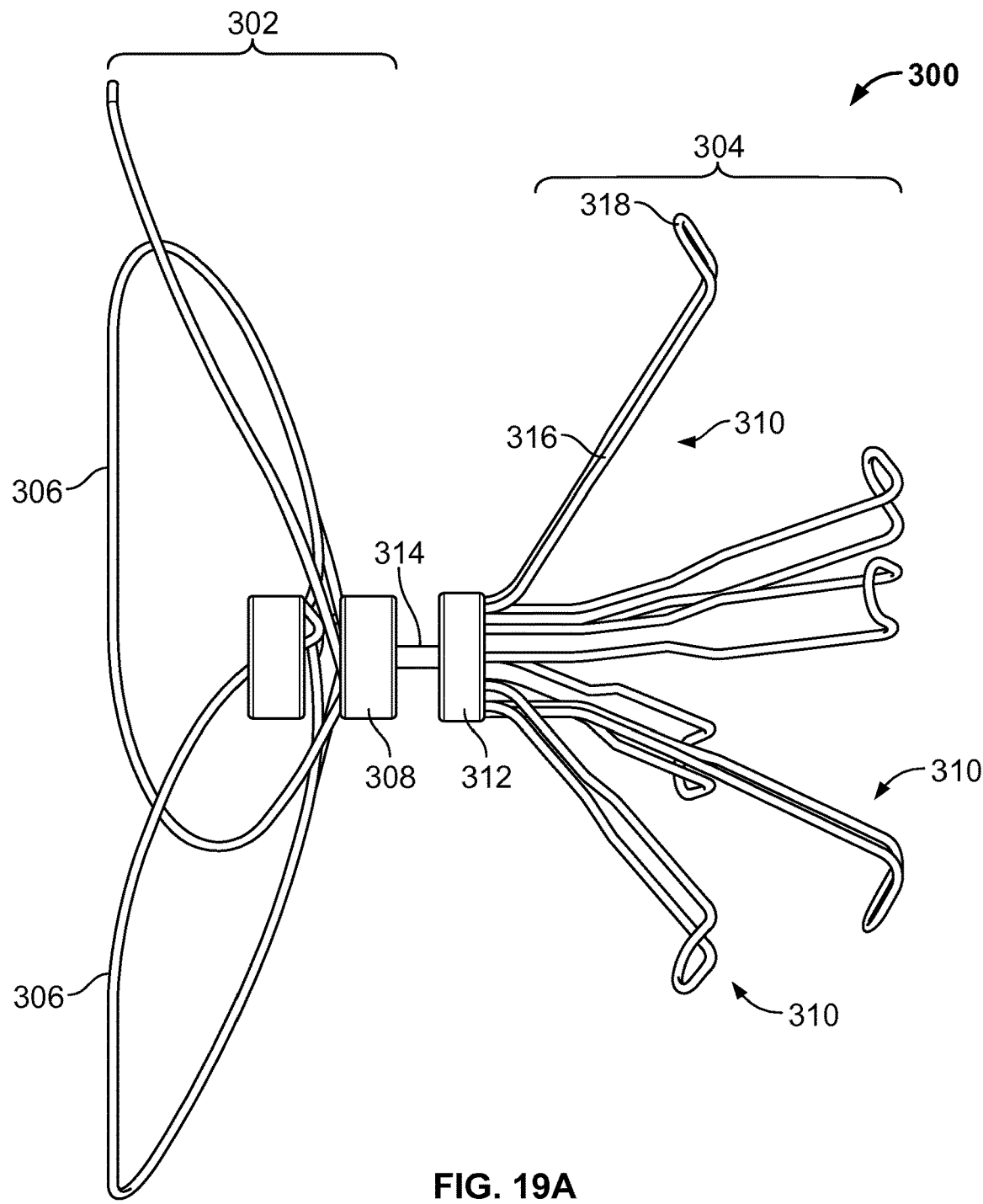
FIG. 19A is a perspective view of an example occlusive device frame.

FIG. 19A is a perspective view of an example occlusion device frame 300 that includes a wire-based occlusion frame 302 and a wire-based anchor frame 304. Elongate frame members 306 of occlusion frame 302 extend from a first hub component 308, and anchor members 310 of anchor frame 304 extend from a second hub component 312. The occlusion frame 302 is coupled to the anchor frame 304 by a flexible connector 314 that couples the first hub component 308 to the second hub component 312. The first hub component 308 and the second hub component 312 may be laser-cut rings in this example, and the wire-based elongate frame members 306 and wire-based anchor members 310 may be crimped, swaged, welded or mechanically engaged to the respective first or second hub component 308 or 312. Lengths of the anchor members 310 are staggered, in this example.

Similar to occlusion frame 102, described above, any appropriate number of elongate frame members 306 can be used. Anchor frame 304 includes six anchor members 310, but any appropriate number of anchor members can be used in other examples. The anchor members 310 include first and second arms of the anchor member that join in a loop at a distal end of the anchor member 310. First portions 316 of the anchor members 310 extend generally distally and radially from the second hub component 310 at an angle that is about 40 degrees distal from a directly radial direction. Second portions 318 of the anchor members 310 extend from the first portions 316 in a generally proximal and radial direction, at an angle that is about 45 degrees distal from a directly radial direction.

Figure 19B:
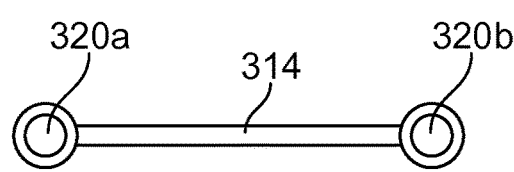
FIG. 19B is an enlarged view of an example flexible connector.

FIG. 19B is an enlarged view of the flexible connector 314, which includes generally spherical members 320 at first and second ends of the flexible connector 314. I some embodiments, connector 314 may be relatively inflexible, semi-rigid, rigid, or a combination thereof. In various implementations the spherical member 320a at the first end of the flexible connector 314 can be received by first hub component 308, and the spherical member 320b at the second end of the flexible connector 314 can be received by second hub component 312. In some examples, flexible connector 314 is a nitinol wire with ball ends 320 formed thereon. In some examples, flexible connector 314 is a solid wire or a stranded wire. In some examples, flexible connector 314 is a polymeric fiber.

Figure 20:
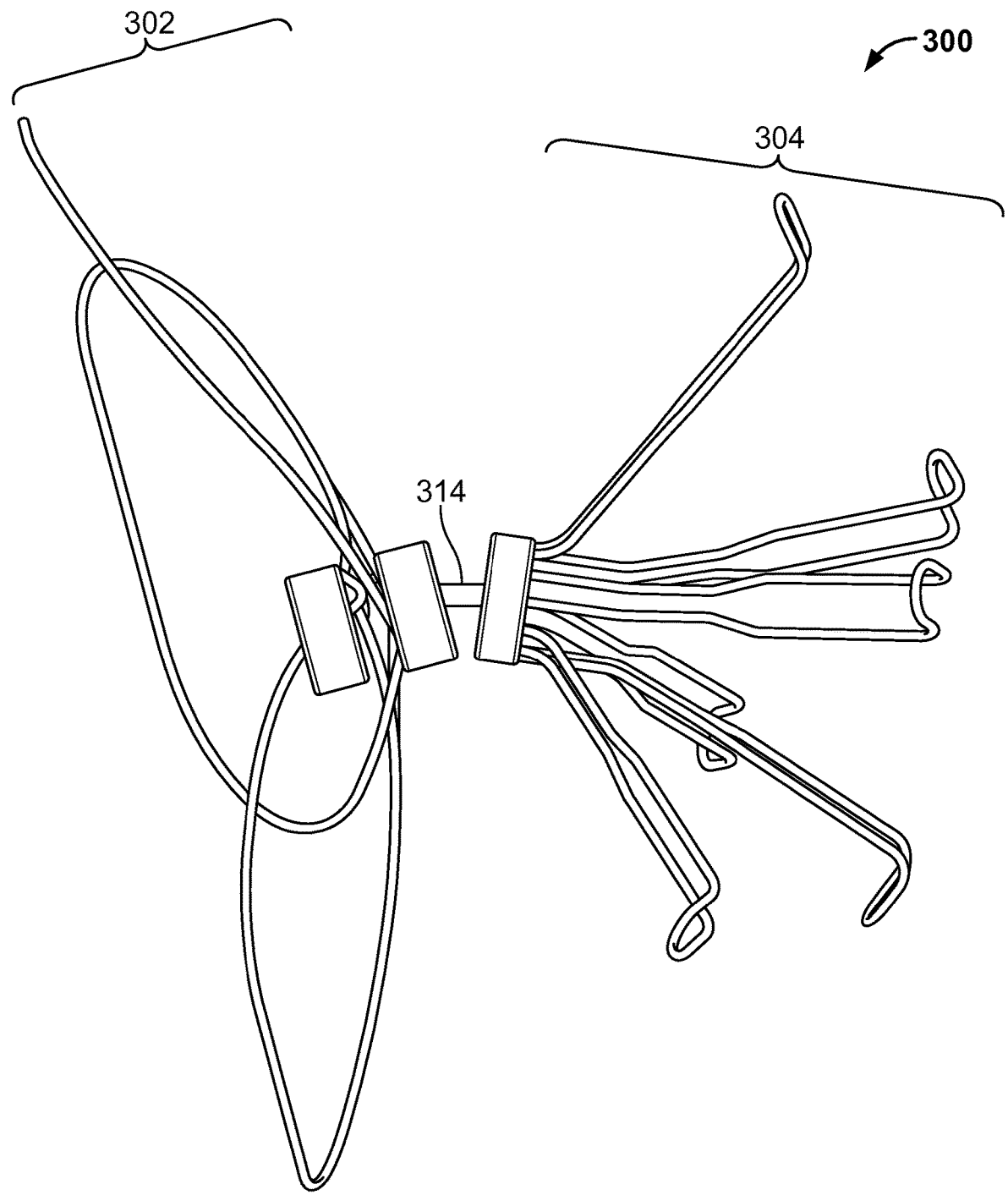
FIG. 20 is a perspective view of an example device frame.

FIG. 20 is a perspective view of device frame 300 showing how flexible connector 314 permits articulation between the occlusion frame 302 and the anchor frame 304. For example, flexible connector 314 can serve as an articulation joint between the occlusion frame 302 and the anchor frame 304. As such, the anchor frame 304 may rotate substantially independently of occlusion frame 302, according to some embodiments. By the same token, the occlusion frame 302 may rotate substantially independently of anchor frame 304, according to some embodiments. This can be advantageous, for example, during deployment of the device, as the anchor frame 304 can be deployed and can engage tissue, and then subsequently the occlusion frame 302 can be deployed and, because of the articulation permitted by the flexible connector 314, can find its natural or preferred orientation, including by rotating if appropriate, without consequently causing the anchor frame to similarly rotate and perhaps tear or rip tissue at the deployment site.

Figure 21A:
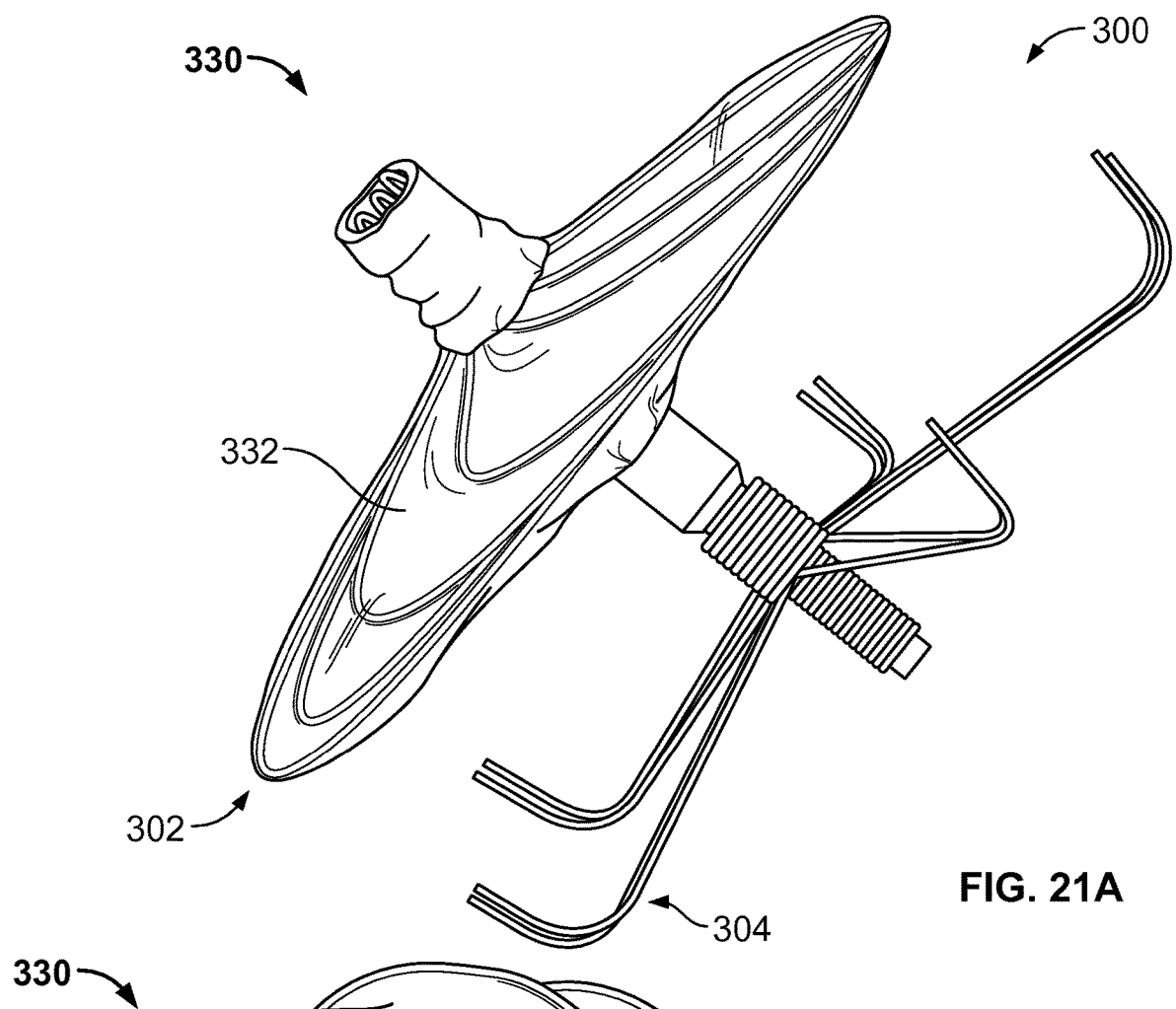
FIGS. 21A and 21B are perspective and back views, respectively, of an example occlusive device.
Figure 21B:
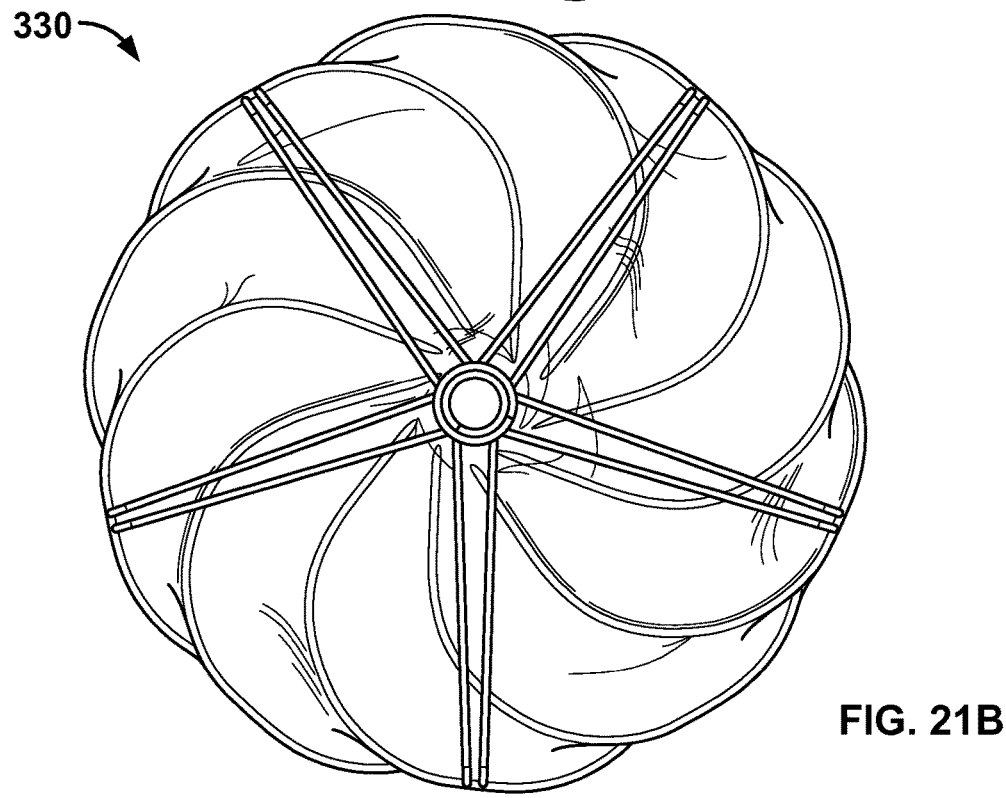

FIGS. 21A and 21B are perspective and back views, respectively, of an example occlusive device 330 that includes the device frame 300 of FIGS. 19A and 19B and a covering component 332 that covers the occlusion frame 302 of the device frame 300.

Figure 22A:
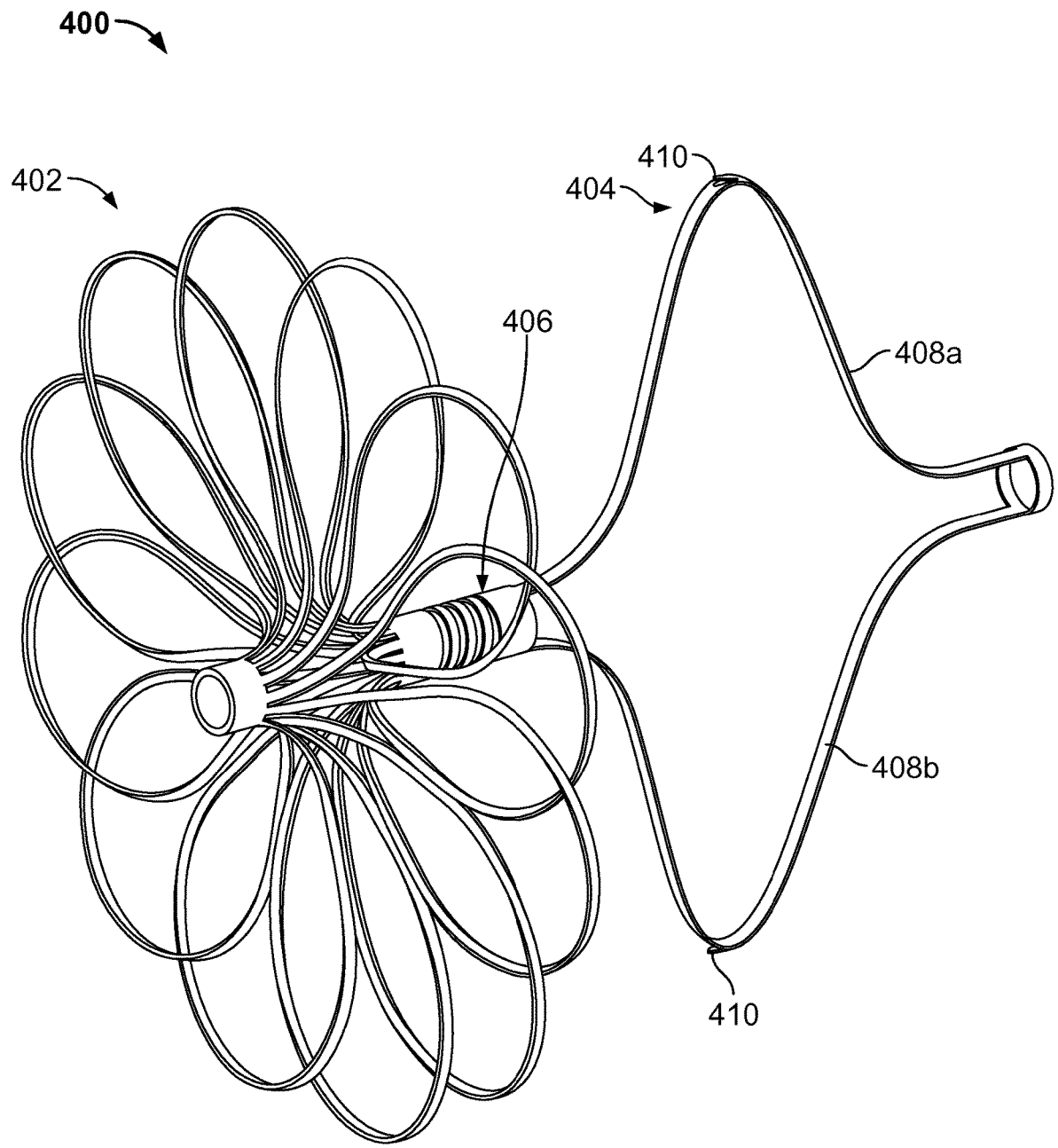
FIGS. 22A and 22B are perspective and side views, respectively, of another example device frame.
Figure 22B:
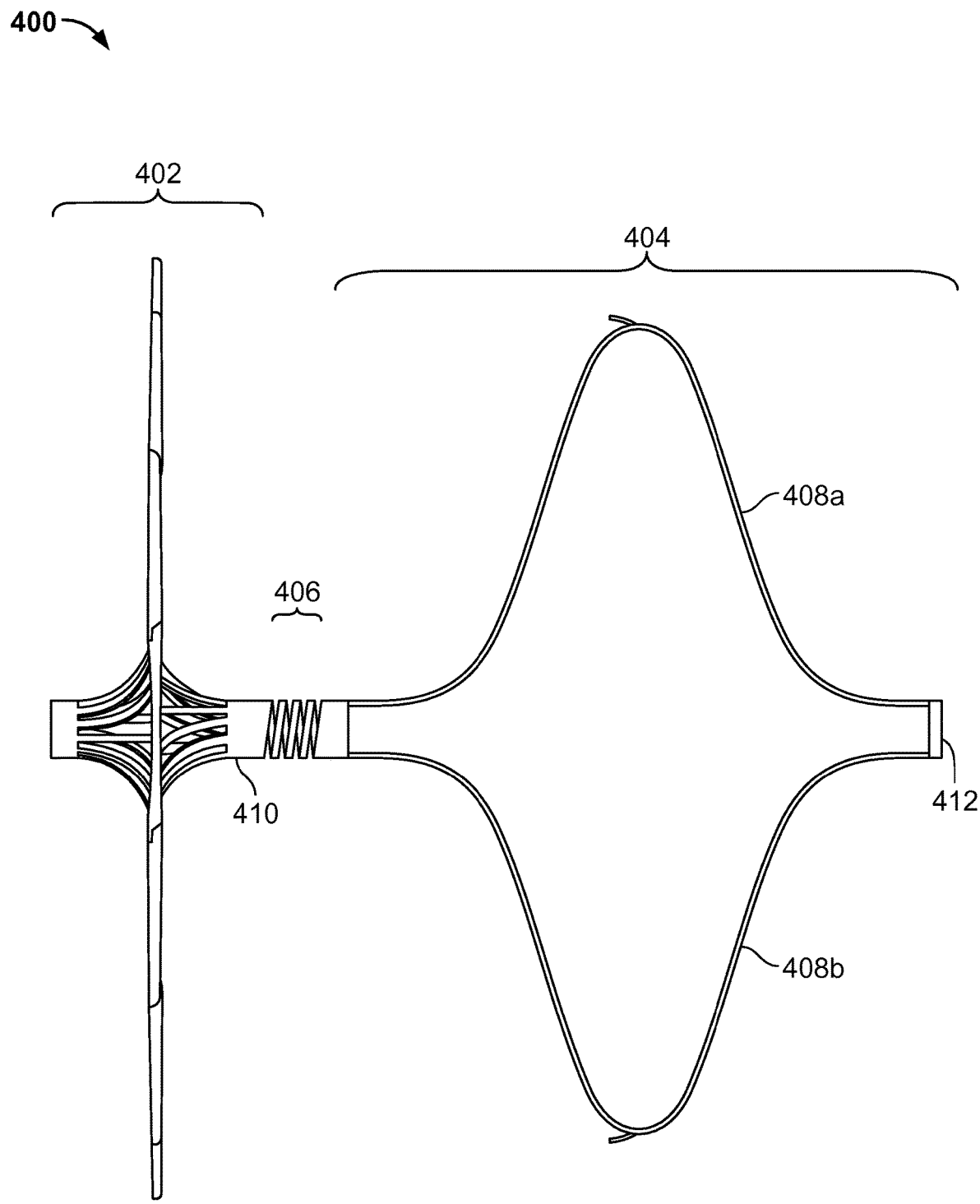

FIGS. 22A and 22B are perspective and side views, respectively, of another device frame 400. Device frame 400 is cut from a single tube of material, and includes an occlusion frame 402, a two-member anchor frame 404, and a flexible linkage 406 that couples the occlusion frame 402 to the anchor frame 404. Occlusion frame 402 is similar to the occlusion frame 102, described above with reference to FIGS. 1-3. Anchor frame 404 is substantially a two-dimensional anchor frame, and has first anchor member 408a and second anchor member 408b. Anchor members 408a and 408b are configured to stretch an occluded space, such as the left atrial appendage, to flatten and minimize a profile of the occluded space. For example, anchor members 408a and 408b can flatten and minimize the left atrial appendage so that it substantially lays flat on the heart, according to some implementations. Each of the anchor members 408a and 408b includes a tine, hook or barb 410 at a crest of the anchor members 408a, 408b for engaging tissue at the deployment site. Penetration depth may be limited by the anchor member 408a, 408b. In some embodiments, anchor members 408a and 408b may have a curved shape. In some examples, the anchor members 408a and 408b may have a curved shape similar to a "potato chip," for example. In some examples, a curved shape may improve conformance, for example. In some examples, curved anchor members 408a and 408b may better conform to a wall of a space to be occluded.

In some embodiments, flexible linkage 406 may permit rotation between the occlusion frame 402 and the anchor frame 410. For example, flexible linkage 406 may be configured to cause anchor frame 404 to rotate a predetermined amount (e.g., about 180 degrees) when anchor frame 404 is deployed from a sheath, for example. The anchor members 408 and/or tine/hook/barb 410 may initially engage tissue upon deployment of the anchor frame 404, and then as the flexible linkage 406 and the occlusion frame 402 are deployed, a torque feature configured with the flexible linkage 406 may cause the anchor frame members 408 to rotate the predetermined amount with respect to the occlusion frame 204. For example, as viewed in FIG. 22B where the anchor members 408a and 408b are oriented substantially vertical prior to the rotation, following the rotation the anchor member 408a may be orientated 408a substantially out of the page, and anchor member 408b may be oriented substantially into the page (or vice versa). Such rotation of the anchor members 408 may cause the appendage (or other occluded space) to flip or twist on itself, and thereby substantially close off the appendage. The occlusion frame 402, covered by a covering component (not shown), further occludes the appendage. In some embodiments, flexible linkage 406 may not permit rotation between the occlusion frame 402 and the anchor frame 410.

Figure 23:
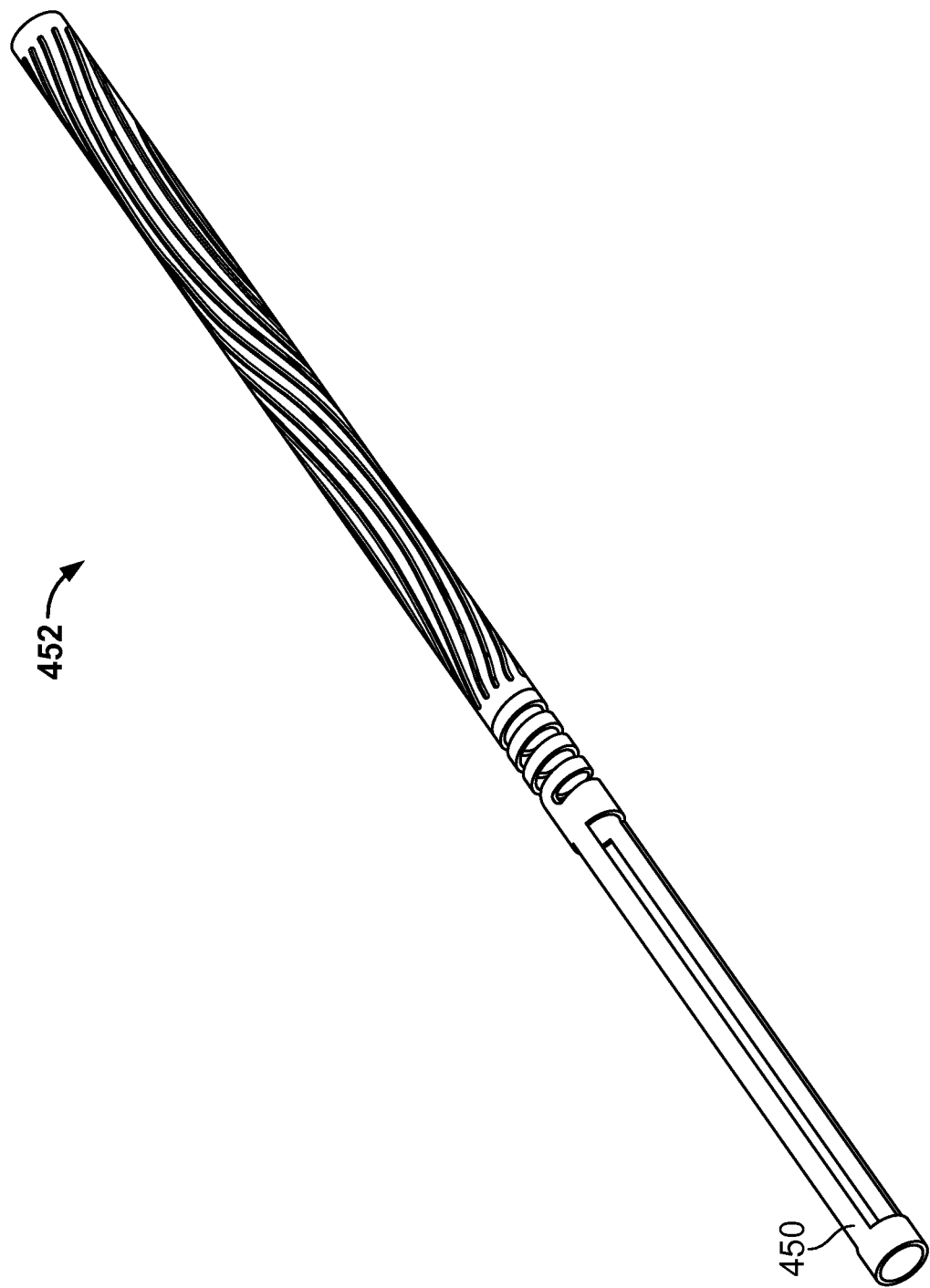
FIG. 23 shows an example tube and an example cut pattern that can be used to cut the tube to create the frame of FIGS. 14A and 14B.

Optionally, a spring or elastic component (not shown), can be included between the first hub component 410 and the cylinder portion 412 at the distal end of the anchor frame 404. This optional feature can increase radial force by pulling and locking over-center, for example. FIG. 23 shows a tube 450 and a cut pattern 452 that can be used to cut the tube 450 to create the frame 400 of FIGS. 22A and 22B.

Figure 24:
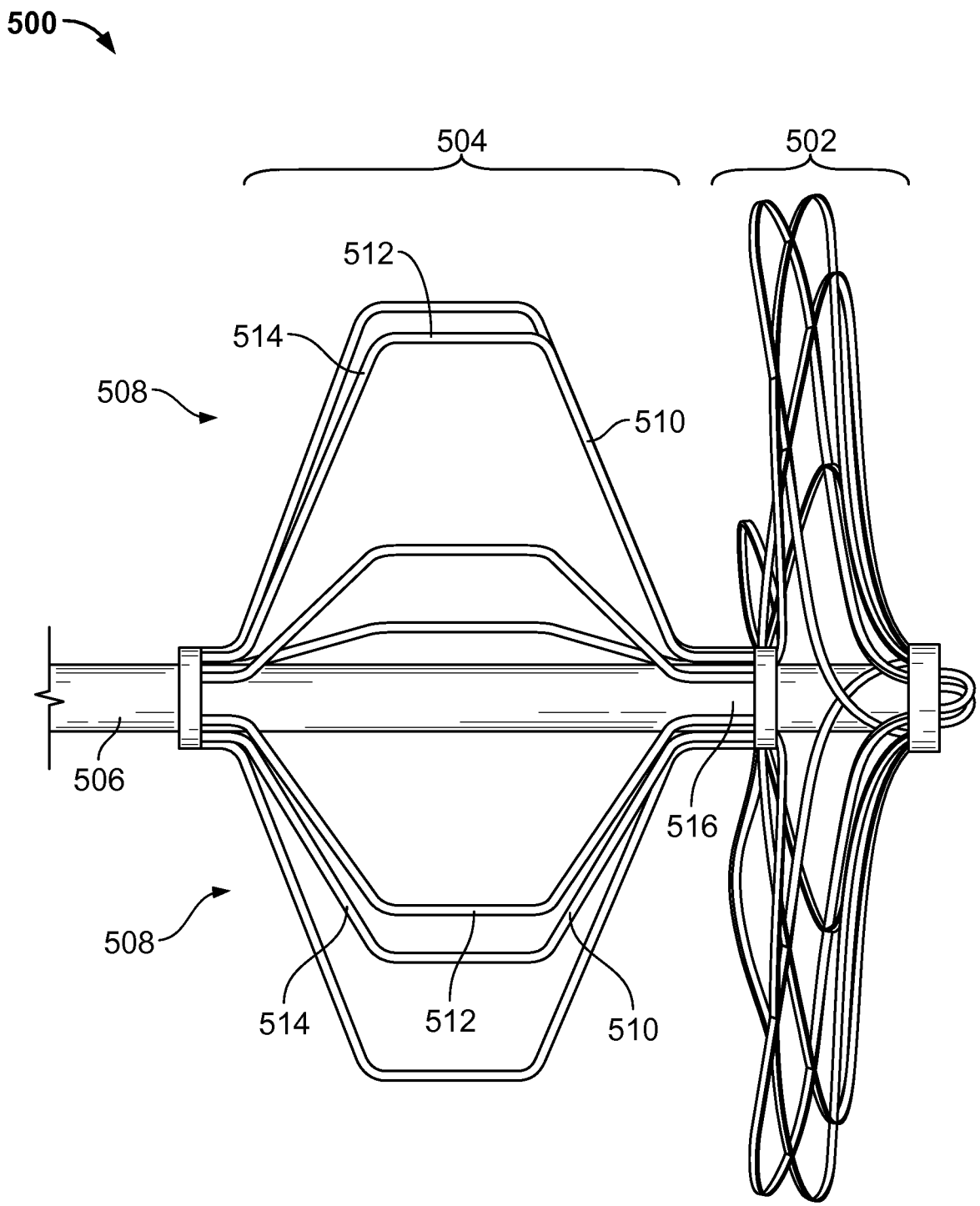
FIG. 24 is a perspective view of another device frame.

FIG. 24 is a perspective view of yet another device frame 500. The device includes an occlusion frame 502 and an anchor frame 504. In the depicted example, the device is mounted on an example mandrel 506. The anchor frame includes anchor members 508. First portions 510 of the anchor members 508 extend generally distally and radially from a second hub component 516, at an angle that is about 15 degrees distal from a directly radial direction. Second portions 512 of the anchor members 508 extend from the first portions 510 in a substantially distal direction. Third portions 514 of the anchor members 508 extend from the second portions 512 in a generally distal and inwardly radial direction, at an angle that is about 15 degrees from a directly inwardly radial direction. Second portions 512 of the anchor members 508 provide a relatively flat surface for opposition to a wall of a space to be occluded, such as the wall of the left atrial appendage. This may minimize opportunity for penetration of the wall, for example, and may minimize pericardial effusion.

Figure 25:
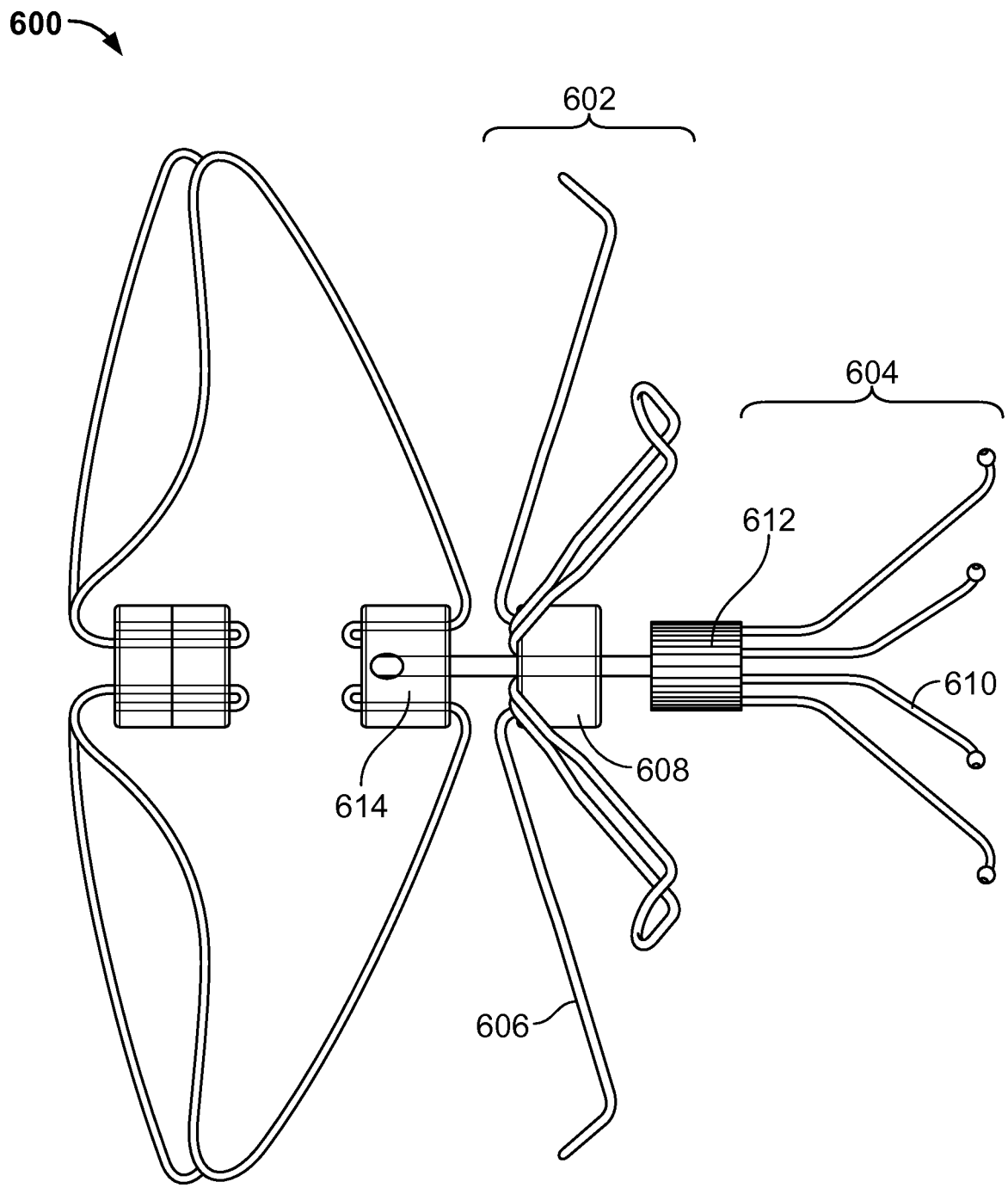
FIG. 25 is a conceptual drawing of an example occlusive device that includes two anchor frames.

FIG. 25 is a conceptual drawing of an example occlusive device 600 that includes two anchor frames. A first anchor frame 602 may substantially correspond to any of the anchor frames discussed herein, except that the anchor members 606 of the first anchor frame may extend from a proximal end of a second hub component 608, in some implementations. In other implementations, the anchor members 606 may extend from a distal end of the second hub component 608, for example. A second anchor frame 604 may be "daisy-chained" distal of the first anchor frame 602, and may provide for two-stage anchor deployments where the second anchor frame 604 is initially deployed, the first anchor frame is thereafter deployed, and the occlusion frame is then deployed.

In various embodiments, the second anchor frame 604 may include anchor members 610 that extend from a distal end of the second hub component 608 (not shown), or from a third hub component 612, which can be coupled to the second hub component 608, to the first hub component 614 (or to both the second hub component 608 and the first hub component 614).

In general, any of the anchor frame designs discussed herein can be modified so that the anchor members extend from the proximal end of the second hub component, as shown in FIG. 25. In some cases, modifying in this manner may shorten device length, and may increase a radial opposition force applied by the anchor members, for example.

In general, any of the occlusion device frames discussed herein can optionally include a spring or elastic component that couples a hub component at the proximal end of the occlusion device frame (e.g., component 124 in FIG. 1) with for example the second hub component, to provide a light tension. In some cases, such light tension can be used to help maintain the shape of the generally disc-shaped member and prevent the generally disc-shaped member from assuming a bulbous shape, for example. In some embodiments, the optional spring can be wound in a direction opposite of the helical wind direction of the occlusion frame elongate members, and this opposite wind direction (e.g., reverse torsion) can help to balance deployment of the device and minimize undesired rotation of the device during deployment, for example.

Figure 26:
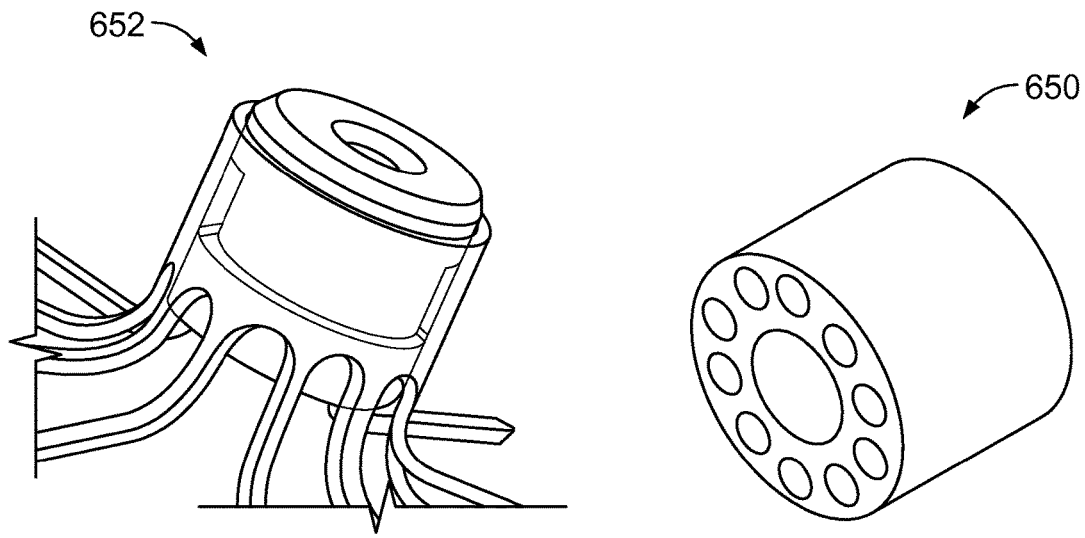
FIG. 26 is a perspective view of an example ring hub component and an example collar lock component.

FIG. 26 is a perspective view of a ring hub 650 that can be used as a hub component in any of the devices discussed herein, for example, and of a collar lock 652. The collar lock 652 is an optional engagement feature that can include an inset groove within the collar lock 652, tab features of the cut-tube frame that can lock into the groove of the collar lock 652.

Figure 27:
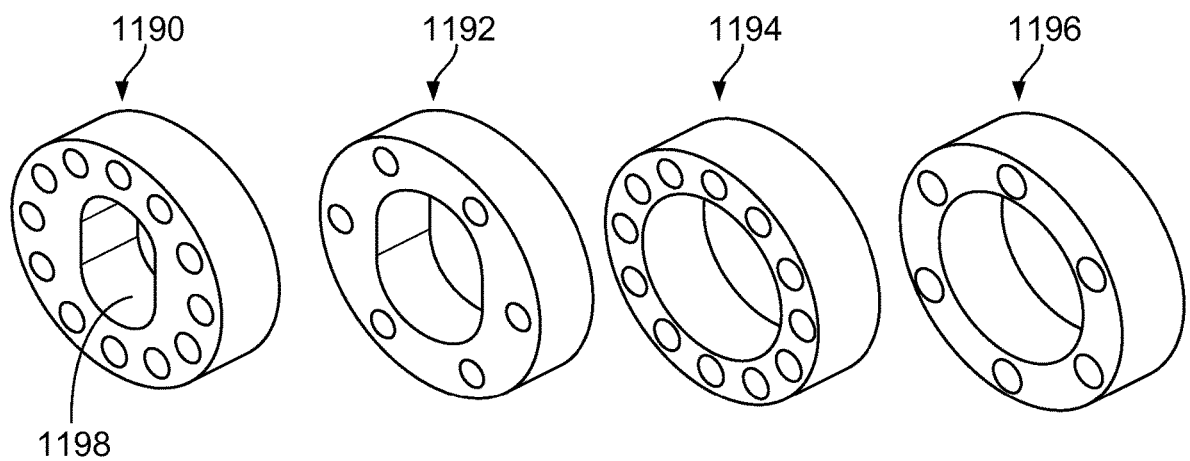
FIG. 27 is a view of various example hub components.

FIG. 27 is a view of various example hub components (e.g., ring hub components) 1190, 1192, 1194, and 1196. Each of the hub components 1190-1196 has a generally ring-shaped body and defines apertures longitudinally though a wall of the ring-shaped body. Components 1190 and 1192 include a center lumen having a non-circular shape, and components 1194 and 1196 include a center aperture having a circular shape. Components 1190 and 1192 may be considered "keyed" components because of the non-circular shape of the center lumen, for example. The central lumen can be used for device deployment, device maneuverability, and maintaining device alignment during deployment, for example, as by coupling with a component of a delivery system.

In various examples, the components 1190-1196 can have different heights or longitudinal lengths, and in some cases two or more components may be stacked, one on top of the other. In some examples, wires having a ball end may couple with a component of FIG. 27 (or of FIG. 28), where the wire passes through an aperture of the component and the ball end prevents the end of the wire from passing through the aperture.

Figure 28:
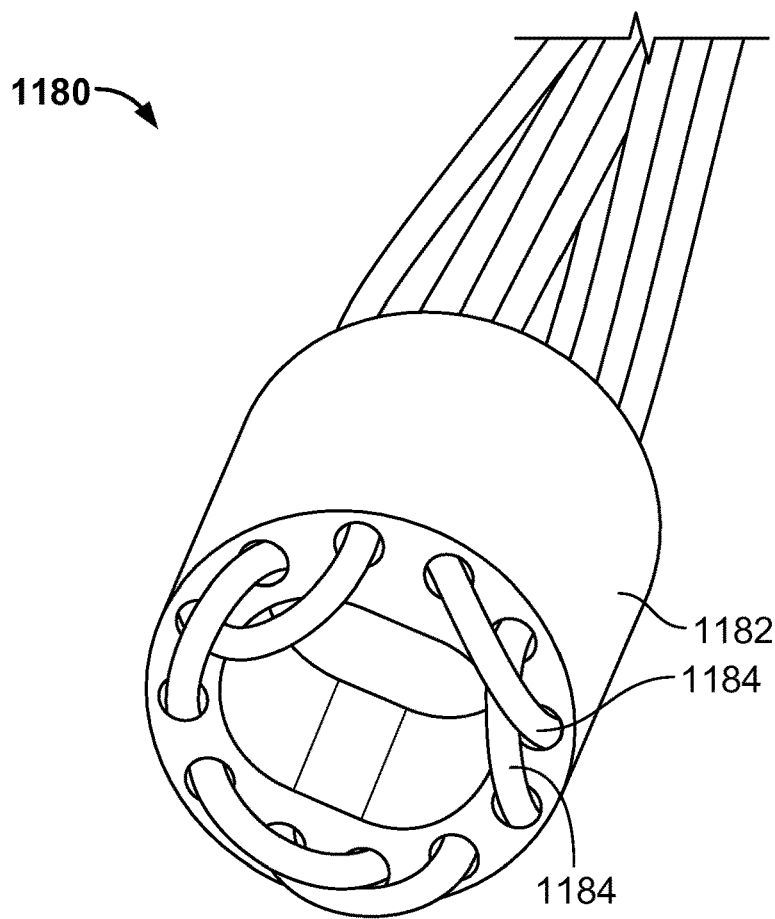
FIG. 28 is a perspective view of another example hub component.

FIG. 28 is a perspective view of another example hub component 1180. In the depicted example, hub component 1180 includes a generally ring-shaped body portion 1182, which includes twelve apertures 1184 that are disposed longitudinally through a wall of the ring-shaped body portion 1182. In some examples, hub component 1180 can be used with two-filar devices that include six wires, and in some examples the hub component 1180 can be used with single-filar devices that include twelve wires.

The apertures 1184 may be laser-cut through the wall of the body portion 1182, in some examples. In some examples, some of the apertures 1184 may have a first diameter, and some of the apertures 1184 may have a second, different, diameter. In some examples, the apertures 1184 all have the same diameter. In general, the apertures 1184 may be equidistantly spaced around the circumference of the body member 1182.

FIG. 28 shows that six wires are used with hub component 1180, where each of the six wires respectively passes through a first aperture 1184 of the hub component 1180 in a first longitudinal direction, and then passes back through the hub component 1180 in the opposite longitudinal direction via a second aperture 1184, where the second aperture 1184 is not adjacent to the first aperture 1184, but rather is offset by one aperture from the first aperture. For example, if the twelve apertures are consecutively numbered 1-12 in a clockwise direction around the body portion 1182, a first wire passes (in different directions) through apertures 1 and 3; a second wire passes (in different directions) through apertures 2 and 4; a third wire passes (in different directions) through apertures 5 and 7; a fourth wire passes (in different directions) through apertures 6 and 8; a fifth wire passes (in different directions) through apertures 9 and 11; and a sixth wire passes (in different directions) through apertures 10 and 12. In some examples some of the wires may have different sizes. For example, the first, third, and fifth wires may have a first diameter (e.g., 0.009"), and the second, fourth, and sixth wires may have a second diameter (e.g., 0.007"). This may allow, for examples certain features (e.g., the device frame or sub-frame) of the device to be formed by wires of the first diameter and other features (e.g., anchor features or assemblies) of the device to be formed by wires of the second diameter. In some examples, the structural features of a device may be created with the larger wire and, for example, anchor features of the device may be created with the smaller wire.

Figure 29:
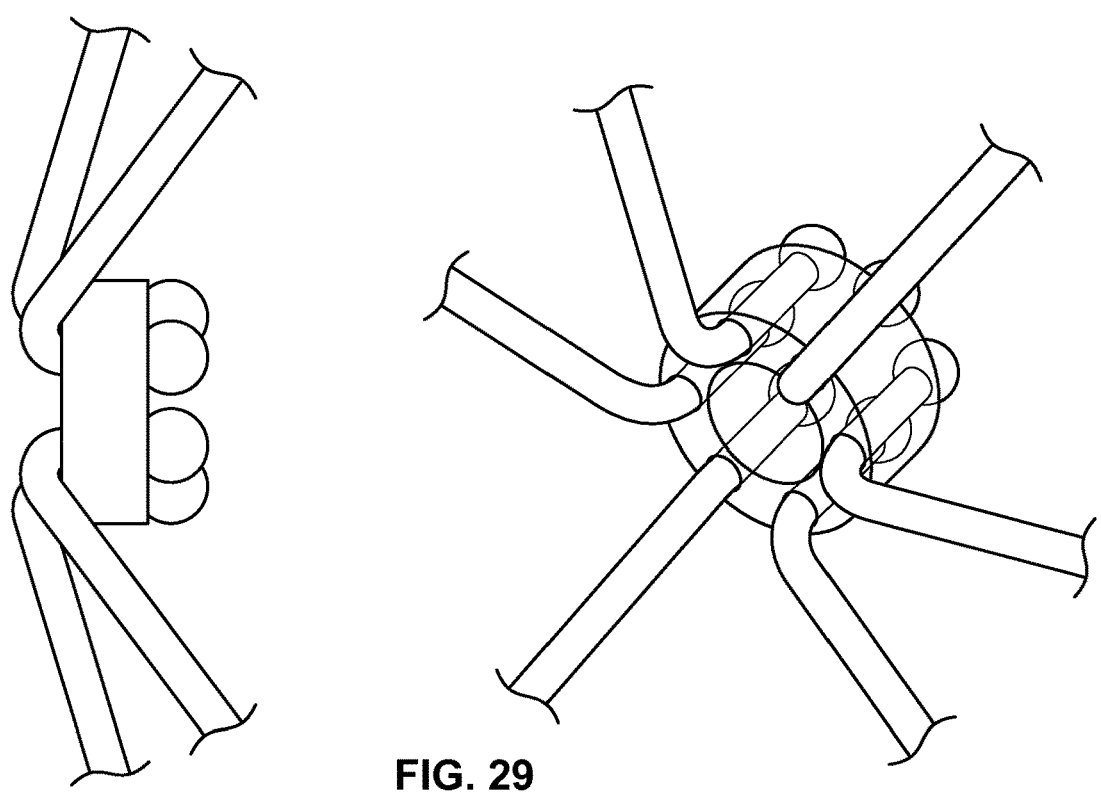
FIG. 29 shows views of various applications of the hub components of FIG. 27 (or FIG. 28).

FIG. 29 shows views of various applications of the hub components 1190-1196 of FIG. 27 (or FIG. 28), and shows examples of how wires with ball ends can be terminated by the hub components. The balls can be formed by melting the wire ends or by other means of manipulating the wire ends.

Figure 30B:
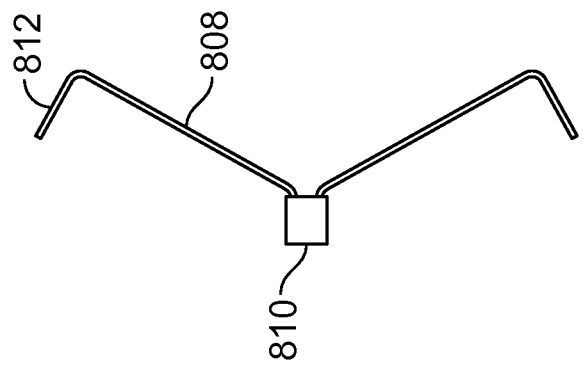
Figure 30A:
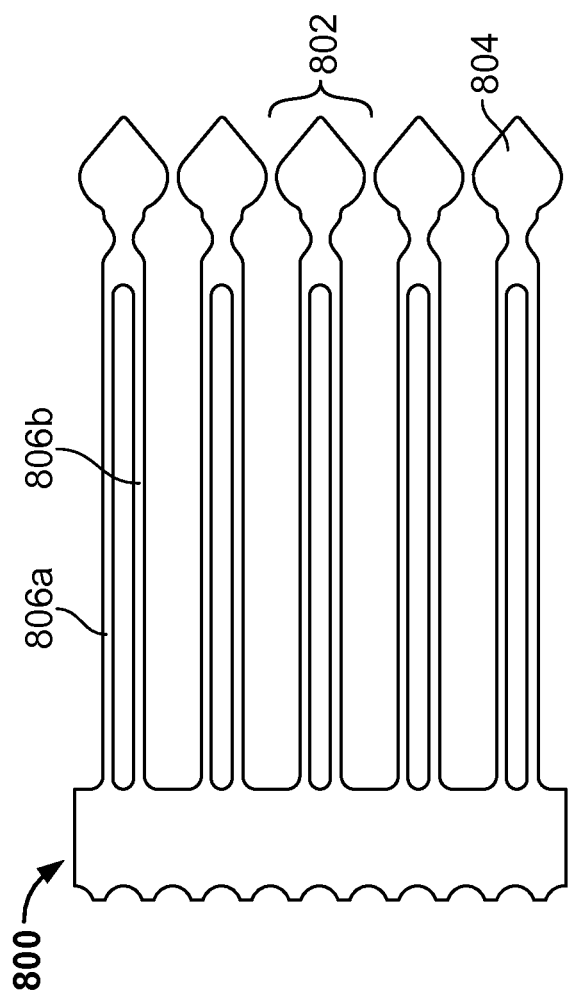

FIG. 30A is a view of an example cutting pattern 800 that can be used to cut a tube (or a portion of a tube) to create an anchor frame that includes anchor members 802 with a "spade" shaped anchor feature 804. Each of the anchor members 802 includes first and second anchor arms 806a and 806b. As shown in FIG. 30B, first portions 808 of the anchor members 802 can extend generally distally and radially from the second hub component 810, at an angle that is about 30 degrees distal from a directly radial direction. Second portions 812 of the anchor members 802 can extend from the first portions 808 in a generally proximal and radial direction, at about a 90 degree angle from the first portions 808. A sharp tip portion of the space feature 804 may be designed to penetrate tissue, and the flared shape of the spade feature 804 may limit tissue penetration depth.

Figure 31B:
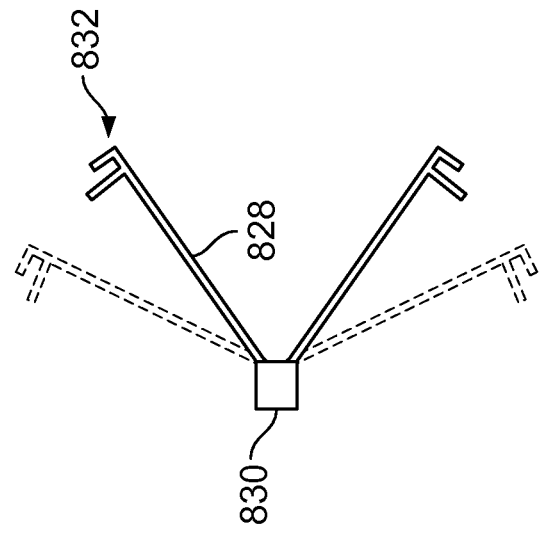
Figure 31A:
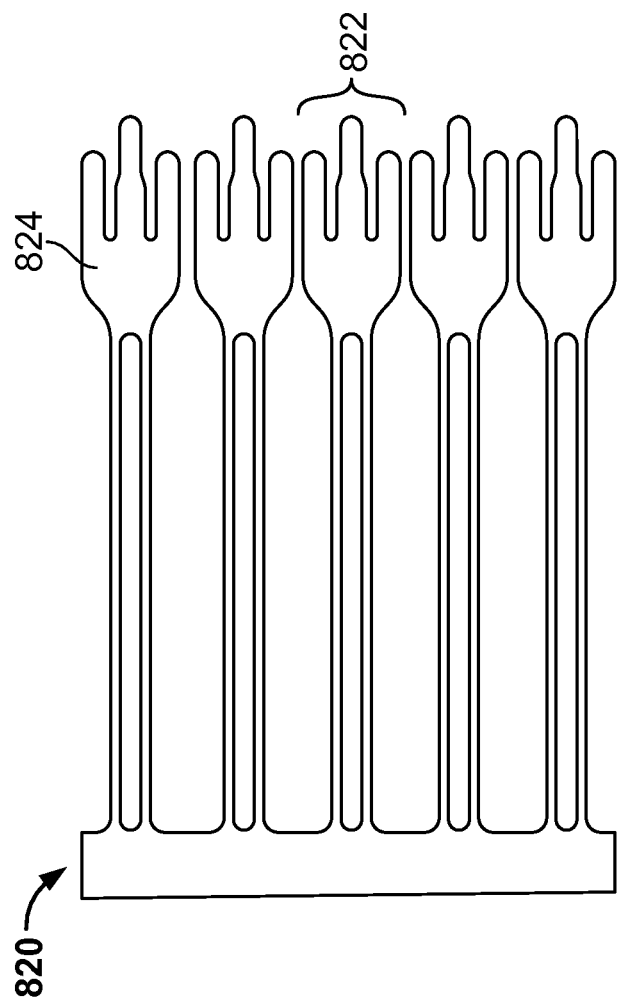

FIG. 31A is a view of an example cutting pattern 820 that can be used to cut a tube (or a portion of a tube) to create an anchor frame that includes anchor members 822 with a feature 824 that includes three prongs: an outer and inner prong and a longer center prong between the outer prong and inner prong. The center prong is slightly longer that the outside prongs, for example, so that when deploying into a cylindrically shaped space, each of the prongs may contact tissue at approximately the same time. Each of the anchor members 822 includes first and second anchor arms. As shown in FIG. 31B, first portions 828 of the anchor members 822 can extend generally distally and radially from the second hub component 830, at an angle that is about 60 degrees distal from a directly radial direction. Second portions 832 of the anchor members 822 can extend from the first portions 828 in a generally proximal and radial direction, at about a 90 degree angle from the first portions 828.

FIG. 32A is a view of an example cutting pattern 850 that can be used to cut a tube (or a portion of a tube) to create an anchor frame that includes anchor members 852 with a feature 854 that includes two prongs that extend at an angle from each other. Each of the anchor members 852 includes first and second anchor arms. As shown in FIG. 32B, first portions 858 of the anchor members 852 can extend generally distally and radially from the second hub component 830, at an angle that is about 45 degrees distal from a directly radial direction. Second portions 862 of the anchor members 852 can extend from the first portions 852 in a generally proximal and radial direction, at about a 90 degree angle from the first portions 852.

Figure 33B:
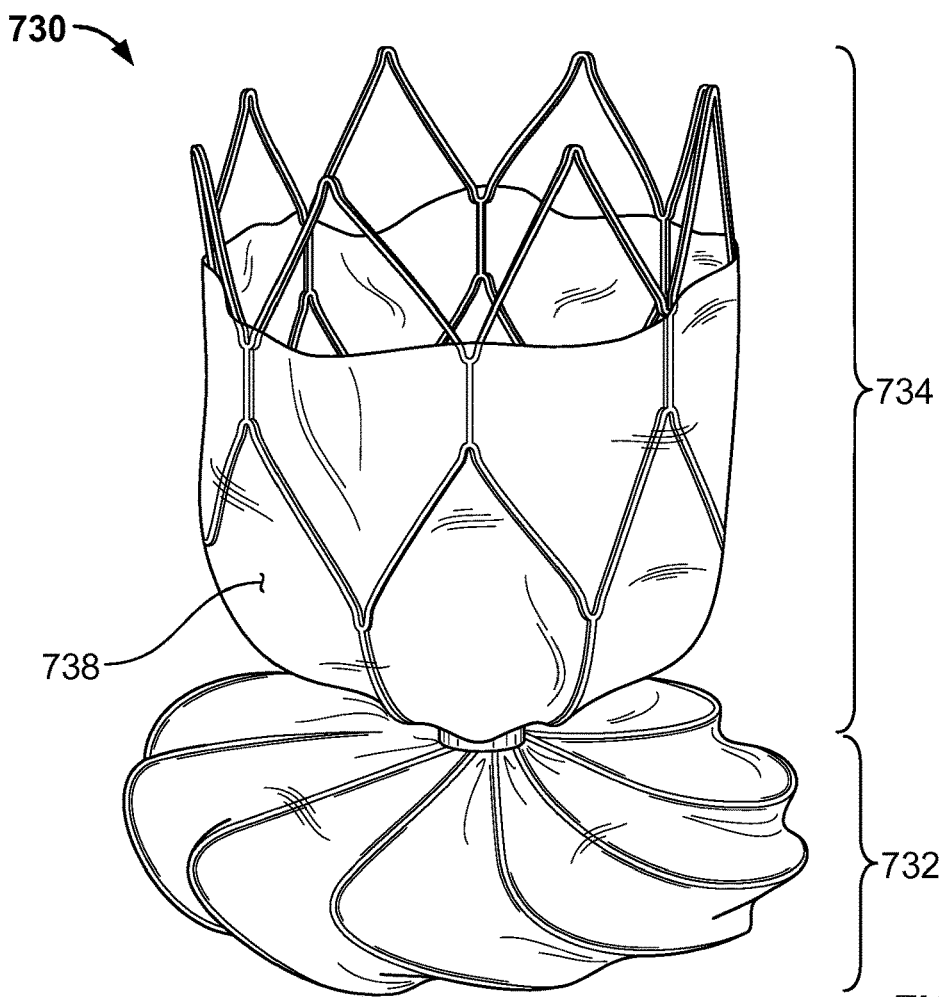
FIG. 33B is a perspective side view of the example occlusive device of FIG. 33A.
Figure 33C:
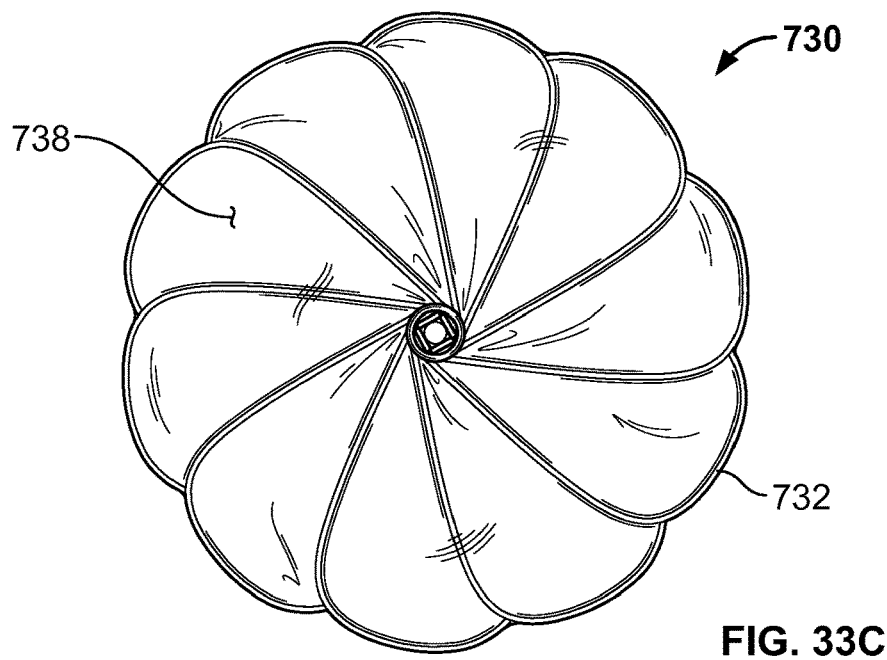
FIG. 33C is a bottom view of the example occlusive device of FIG. 33A.

FIGS. 33A through 33C are a top, perspective side, and bottom view, respectively, of another example occlusive device 730 that can be used to occlude a hole, defect, aperture, or appendage within a body of a patient. The occlusive device 730 includes two sub-frames: an occlusion frame 732 (or disc-shaped member) and an anchor frame 734. In some embodiments, the occlusion frame 732 and the anchor frame 734 are formed from the same piece of precursor material. For example, in some embodiments the occlusion frame 732 and the anchor frame 734 can be formed from a single tube or sheet of material that is cut and expanded to form the frame configurations of the occlusion frame 732 and the anchor frame 734. In such embodiments, the occlusion frame 732 and the anchor frame 734 are a unitary member. In some such embodiments, the occlusion frame 732 and the anchor frame 734 are a seamless member. In some embodiments, the unitary construct of the occlusive device can include anchor features.

In some embodiments, at least a portion of the occlusion frame 732 is covered by a covering component 738 that is configured to modulate or inhibit the passage of blood and/or thrombus through the covering component 738, i.e., to substantially occlude the flow of blood and/or thrombus through the covering component 738. In some embodiments, the anchor frame 734 is not covered by the covering component 738. In some embodiments, a portion of the anchor frame 734 is covered by the covering component 738 (as shown), and in some embodiments the anchor frame 734 is substantially covered by the covering component 738 (or by a second covering component). More than one covering component 738 can be used on the occlusive device 730 in some embodiments. That is, some portions of the occlusive device 730 can be covered by a first covering component and other portions of the occlusive device 730 can be covered by a second covering component. In some embodiments, more than two separate covering components can be included on an occlusive device. The separate covering components may be made of the same material or of different materials, and may have the same material treatments or different material treatments. The covering component 738 can be made from any of the types of coverings, and can include any of the treatments, described elsewhere herein.

In some embodiments, the occlusion frame 732 and the anchor frame 724 are constructed from material that is cut and then expanded. For example, in some embodiments the occlusion frame 732 and the anchor frame 724 are made from a tube or sheet of material that is laser-cut and then expanded (and heat-set in some embodiments) to the configuration substantially as shown. In some embodiments, NiTi is used as the material, but other materials such as stainless steel, L605 steel, and polymers may also be used. In some embodiments, the constructions of the occlusion frame 732 anchor frame 724 can include hubs and wire elongate members as described elsewhere herein. In some embodiments, the occlusive devices provided herein include a combination of types of frame constructs. For example, a portion of the frame of an occlusive device can be formed by cutting and expanding a material, and another portion of the frame can be made from one or more wires that may or may not be attached to a hub or hubs (wherein hubs include, but are not limited to, eyelets, rings, crimp collars, and the like).

The occlusion frame 732 can have any of the configurations of disc-shaped members, and any of the variations thereof, that are described elsewhere herein. In the embodiment depicted, the occlusion frame 732 is a construct of overlapping petals. In this embodiment, ten overlapping petals are included, but in other embodiments, two, three, four, five, six, seven, eight, nine, eleven, twelve, or more than twelve overlapping petals are included. In some embodiments, the petals do not overlap each other. In some embodiments, frame members are configured into orientations that are not petals (e.g., FIGS. 35A-36B). The occlusion frame 732 is a conformable member. That is, the occlusion frame 732 can readily conform in shape to the topography of the anatomy surrounding the anchor frame 732 at the implant site.

In some embodiments, the anchor frame 734 can have one or more rows of cells. In some embodiments, the cells have shapes such as, but not limited to, hexagonal, diamond-shaped, parallelogram, and the like. In the depicted embodiment, two rows of hexagonal cells are included. In some embodiments, one, two, three, four, five, six, or more than six rows of cells are included. The anchor frame 734 is a conformable member. That is, the shape of the anchor frame 734 can readily conform and assimilate to the topography of the anatomy surrounding the anchor frame 734 at the implant site. In some embodiments, the anchor frame 734 is generally cylindrical.

In some embodiments, the occlusion frame 732 and the anchor frame 724 are a unitary construct. For example, the occlusion frame 732 and the anchor frame 724 can be made from a single material component such as a tube or sheet. In such cases, the connection between the occlusion frame 732 and the anchor frame 724 is confluent with the occlusion frame 732 and the anchor frame 724. In some embodiments, the occlusion frame 732 and the anchor frame 724 are interconnected using a connecting member such as those described elsewhere herein (e.g., FIGS. 23, 19A, and 19B). In some embodiments, portions of the occlusive device 730 can include anchoring features.

Figure 34A:
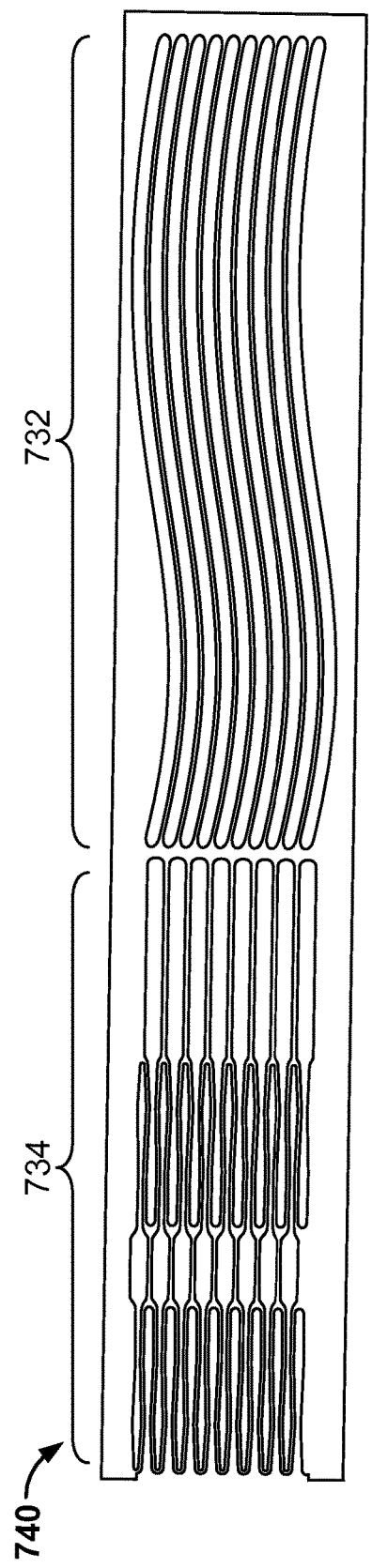
FIG. 34A is a cutting pattern that can be used to cut a tube (or a portion of a tube) to create the frame of the occlusive device of FIGS. 33A-33C.

FIG. 34A illustrates a material cutting pattern 740 that can be used to form the occlusive device 730. The portions of the cutting pattern 740 that will form the occlusion frame 732 and the anchor frame 724 are identified. Using pattern 740, the occlusion frame 732 and the anchor frame 724 can be formed as a unitary member, or as separate members that are connected as components of an assembled occlusive device 730. In some cases, the material cutting pattern 740 can be utilized for laser-cutting a tube of material. In some such cases, the occlusion frame 732 and the anchor frame 724 can be a unitary and seamless construct. Or, in some cases a planar sheet of material can be cut as shown and the sheet can thereafter be formed into a tube. Any of the materials described herein can be used.

Figure 34B:
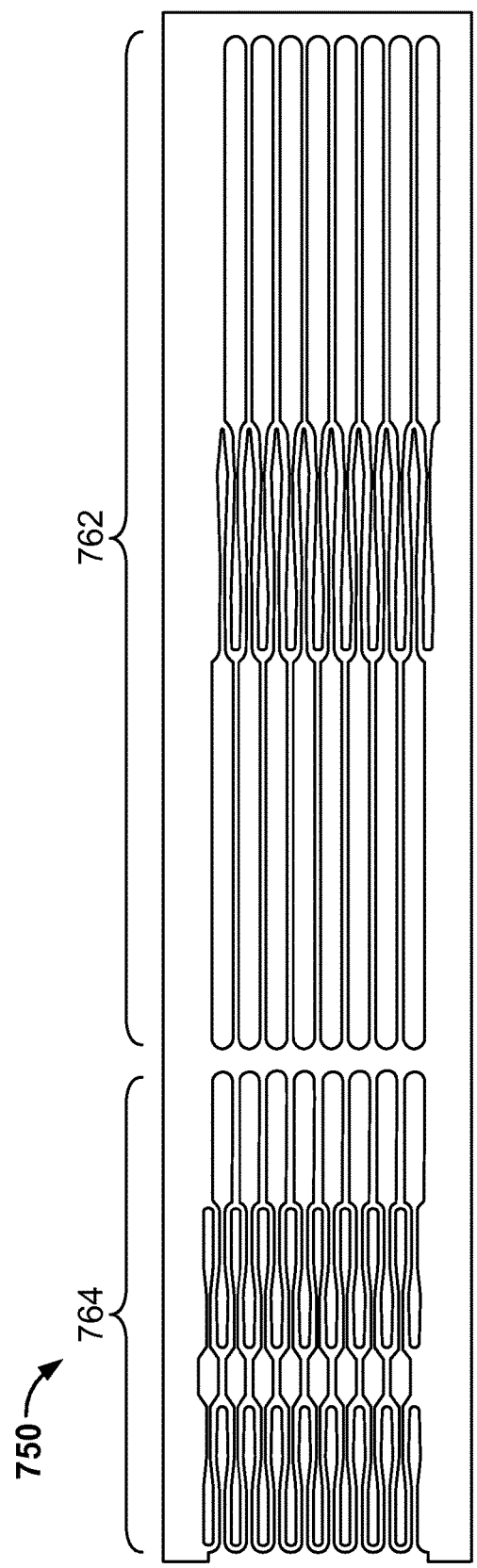
FIG. 34B is a cutting pattern that can be used to cut a tube (or a portion of a tube) to create the frame of the occlusive device of FIGS. 35A, 35B, 36A, and 36B.

FIG. 34B illustrates a material cutting pattern 750 that can be used to form another example occlusive device (refer to occlusive device 760 of FIGS. 35A, 35B, 36A, and 36B). The portions of the cutting pattern 750 that will form the occlusion frame 762 and the anchor frame 764 are identified. Using pattern 750, the occlusion frame 762 and the anchor frame 764 can be formed as a unitary member, or as separate members that are connected as components of an assembled occlusive device 750. In some cases, the material cutting pattern 750 can be utilized for laser-cutting a tube of material. In some such cases, the occlusion frame 762 and the anchor frame 764 can be a unitary and seamless construct. Or, in some cases a planar sheet of material can be cut as shown and the sheet can thereafter be formed into a tube. Any of the materials described herein can be used. The occlusion frame 762 is an example of a construct that does not have petals. The occlusion frame 762 is one such example, and other non-petal constructs are also envisioned within the scope of this disclosure.

Figure 35A:
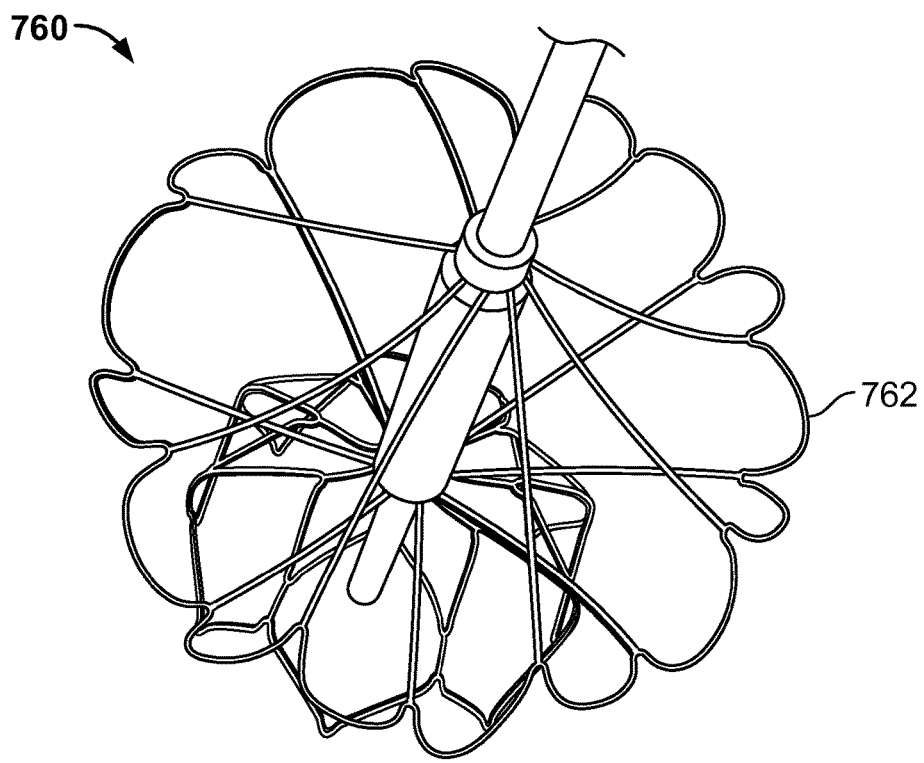
FIG. 35A is a perspective view of the frame of another example occlusive device in accordance with embodiments provided herein.
Figure 35B:
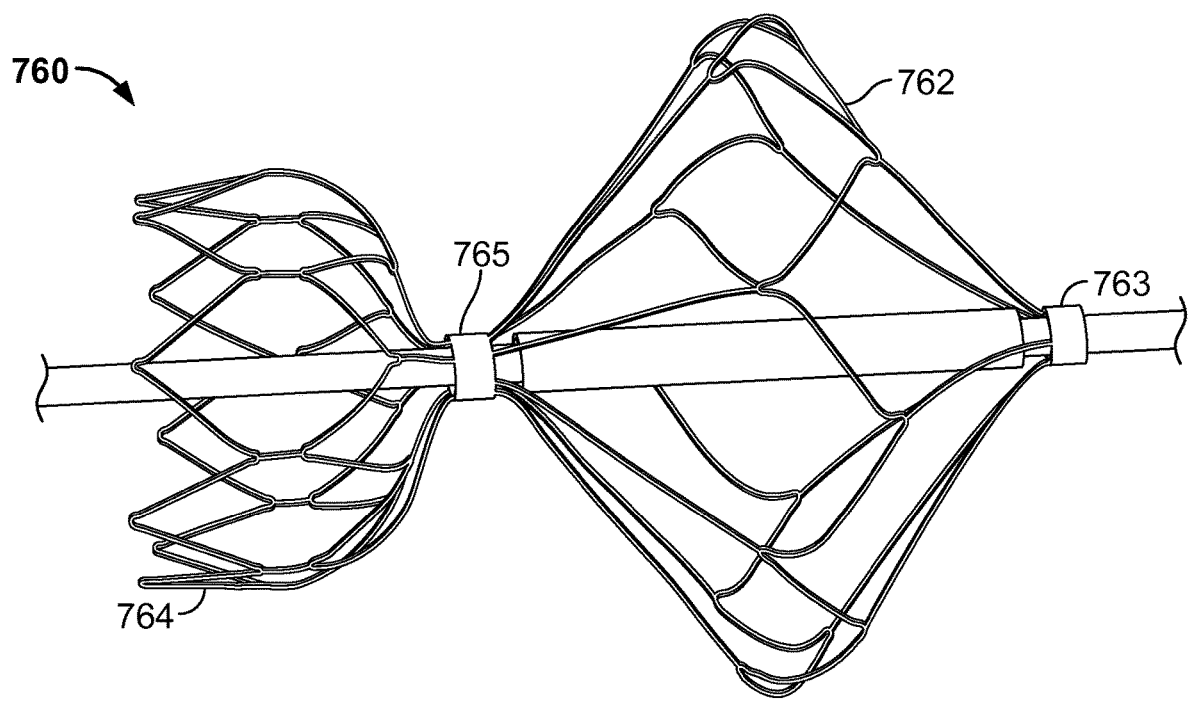
FIG. 35B is a side view of the frame of the occlusive device of FIG. 35A.
Figure 36A:
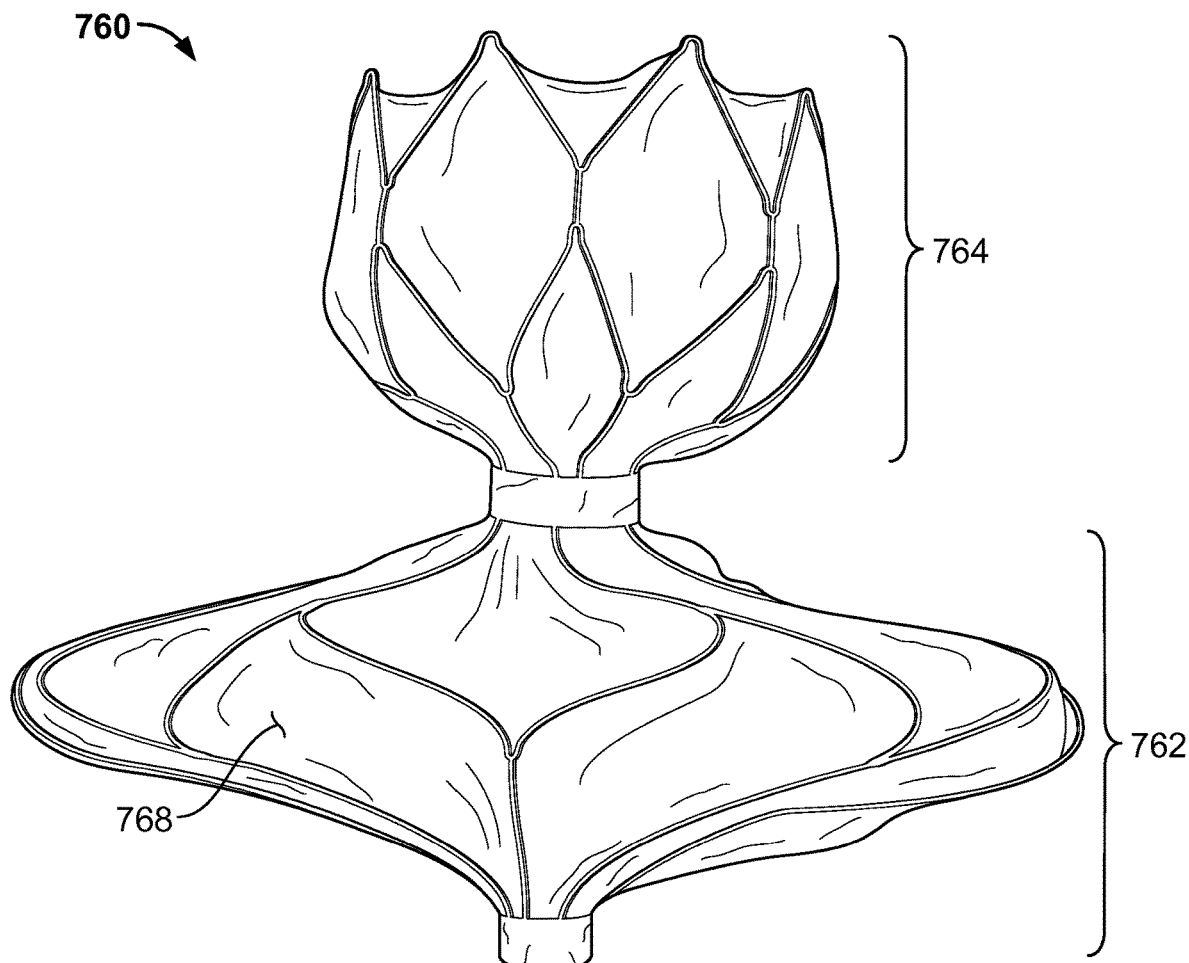
FIG. 36A is a side view of the occlusive device of FIGS. 35A and 35B with a covering on the frame of the occlusive device.
Figure 36B:
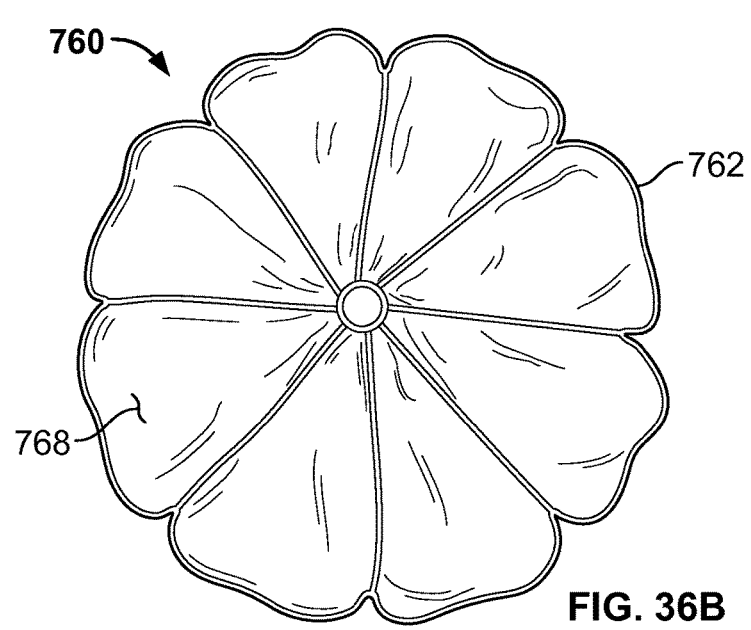
FIG. 36B is an end view of the occlusive device of FIG. 36A.

FIGS. 35A, 35B, 36A, and 36B are illustrations of another example occlusive device 760 that can be used to occlude a hole, defect, aperture, or appendage within a body of a patient. FIGS. 35A and 35B show just the two sub-frames: an occlusion frame 762 (or disc-shaped member) and an anchor frame 764. FIGS. 36A and 36B show the occlusive device 760 with a covering component 768. In some embodiments, the occlusion frame 762 and the anchor frame 764 are formed from the same piece of precursor material. For example, in some embodiments the occlusion frame 762 and the anchor frame 764 can be formed from a single tube or sheet of material that is cut and expanded to form the frame configurations of the occlusion frame 762 and the anchor frame 764. In such embodiments, the occlusion frame 762 and the anchor frame 764 are a unitary member. In some such embodiments, the occlusion frame 762 and the anchor frame 764 are a seamless member. In some embodiments, the unitary construct of the occlusive device can include anchor features. Such frame construction techniques can also be used for the formation of the other occlusive devices provided herein.

While the device frames discussed herein are generally described with reference to occlusion applications, for filtering applications where substantial occlusion is not desired, the occlusion frame may be referred to as a filter frame. That is, any of the described occlusion frames may also be filter frames, for example.

In some embodiments, the occlusion frame 762 and the anchor frame 764 are both substantially covered by a covering component 768 that is configured to modulate or inhibit the passage of blood and/or thrombus through the covering component 768. In some embodiments, some but not all portions of the occlusion frame 762 are covered by a covering component 768. In some embodiments, some or all portions of the anchor frame 764 are not covered by the covering component 768. In some embodiments, a portion of the anchor frame 764 is covered by the covering component 768, and in some embodiments (as shown) the anchor frame 764 is substantially covered by the covering component 768 (or by a second covering component). More than one covering component 768 can be used on the occlusive device 760 in some embodiments. That is, some portions of the occlusive device 760 can be covered by a first covering component and other portions of the occlusive device 760 can be covered by a second covering component. In some embodiments, more than two separate covering components can be included on an occlusive device. The separate covering components may be made of the same material or of different materials, and may have the same material treatments or different material treatments.

In some embodiments, the occlusion frame 762 and the anchor frame 764 are constructed from material that is cut and expanded (refer to FIG. 34B). For example, in some embodiments the occlusion frame 762 and the anchor frame 764 are made from a tube or sheet of material that is laser-cut and then expanded (and heat-set in some embodiments) to the configuration substantially as shown. In some embodiments, NiTi is used as the material, but other materials such as stainless steel and polymers may also be used. In some embodiments, the constructions of the occlusion frame 762 anchor frame 764 can include hubs and wire elongate members as described elsewhere herein. In some embodiments, the occlusive devices provided herein include a combination of types of frame constructs. For example, a portion of the frame of an occlusive device can be formed by cutting and expanding a material, and another portion of the frame can be made from one or more wires that may or may not be attached to a hub or hubs (wherein hubs include, but are not limited to, eyelets, rings, crimp collars, and the like).

The construction of example occlusion frame 762 is as follows (as shown in FIG. 34B). Elongate members extend from the proximal hub 763 of the occlusion frame 762. The elongate members extending from the proximal hub 763 bifurcate to create two bifurcated branches. Each bifurcated branch then joins with another bifurcated branch that originated from an adjacent elongate member that extends from the proximal hub 763. Then the joined bifurcated branches (which comprise a single elongate member) extend to the connecting hub 765. The elongate occlusion frame members are thereby arranged to form an interconnected occlusion structure. In some embodiments the interconnected occlusion structure comprises a generally disc-shaped member. This construction of the occlusion frame 762 provides a highly stable structure that is resistant to malformations of the occlusion frame 762 during deployment and in situ. The example occlusion frame 762 does not include independently moving petals. Other types of occlusion frame constructs that do not include petals are also envisioned within the scope of this disclosure, and occlusion frame 762 is one example of such. The occlusion frame 762 is a conformable member. That is, the occlusion frame 762 can readily conform in shape to the topography of the anatomy surrounding the anchor frame 762 at the implant site. In addition, the anchor frame 764 is a conformable member. That is, the shape of the anchor frame 764 can readily conform and assimilate to the topography of the anatomy surrounding the anchor frame 764 at the implant site.

In some embodiments, the anchor frame 764 can have one or more rows of cells. In some embodiments, the cells have shapes such as, but not limited to, hexagonal, diamond-shaped, parallelogram, and the like. In the depicted embodiment, two rows of hexagonal cells are included. In some embodiments, one, two, three, four, five, six, or more than six rows of cells are included. The cells are defined by elongate members of the anchor frame 764 that are arranged to form an interconnected anchor structure. In some embodiments the interconnected anchor structure comprises a generally cylindrical member. The anchor frame 764 is a conformable member. That is, the shape of the anchor frame 764 can readily conform and assimilate to the topography of the anatomy surrounding the anchor frame 764 at the implant site. In some embodiments, the anchor frame 764 is generally cylindrical.

Figure 37A:
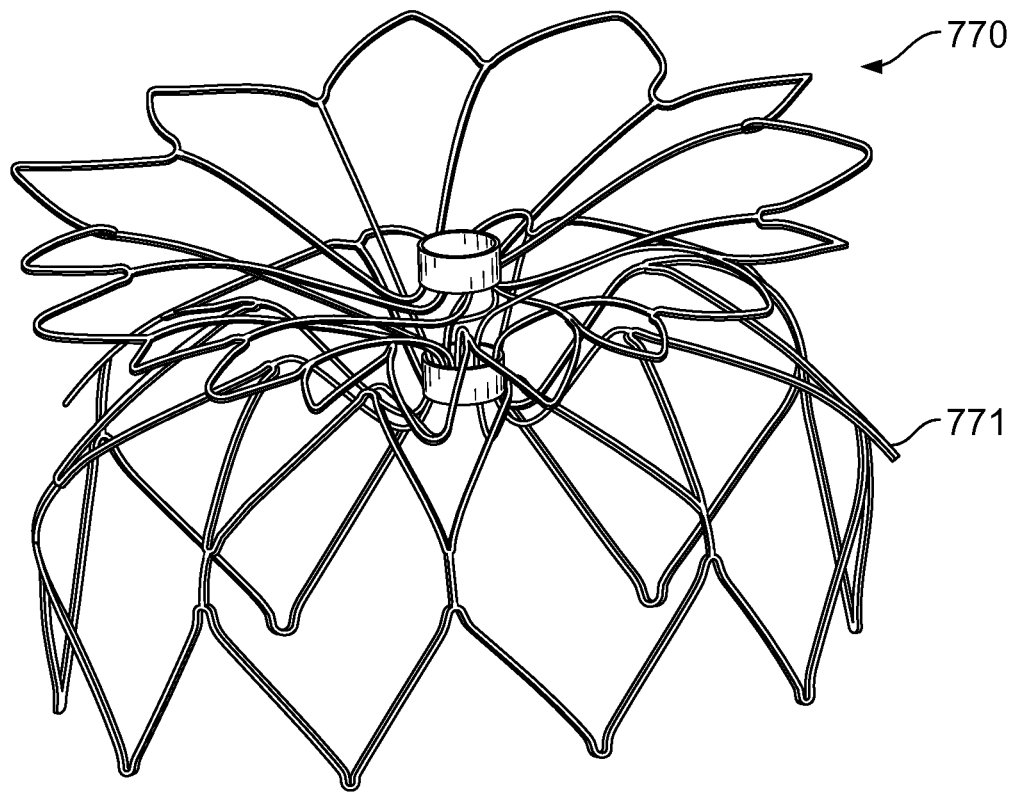
FIG. 37A is a perspective view of a frame of another example occlusive device in accordance with embodiments provided herein.

FIG. 37A is another example occlusive device 770. The example occlusive device 770 may include a covering component (not shown) as with other embodiments of occlusive devices described herein. The occlusive device 770 is an example of an anchor frame that includes one row of hexagonal cells. Additionally, the occlusive device 770 includes mid-point anchors 771 that are free ends located on the periphery and near the axial-midpoint of the anchor frame. In some embodiments, the occlusive device 770 is a unitary frame construct (including the mid-point anchors 771). In some embodiments, the occlusive device 770 is made from a combination of frame component parts that were formed distinctly from each other.

Figure 37B:
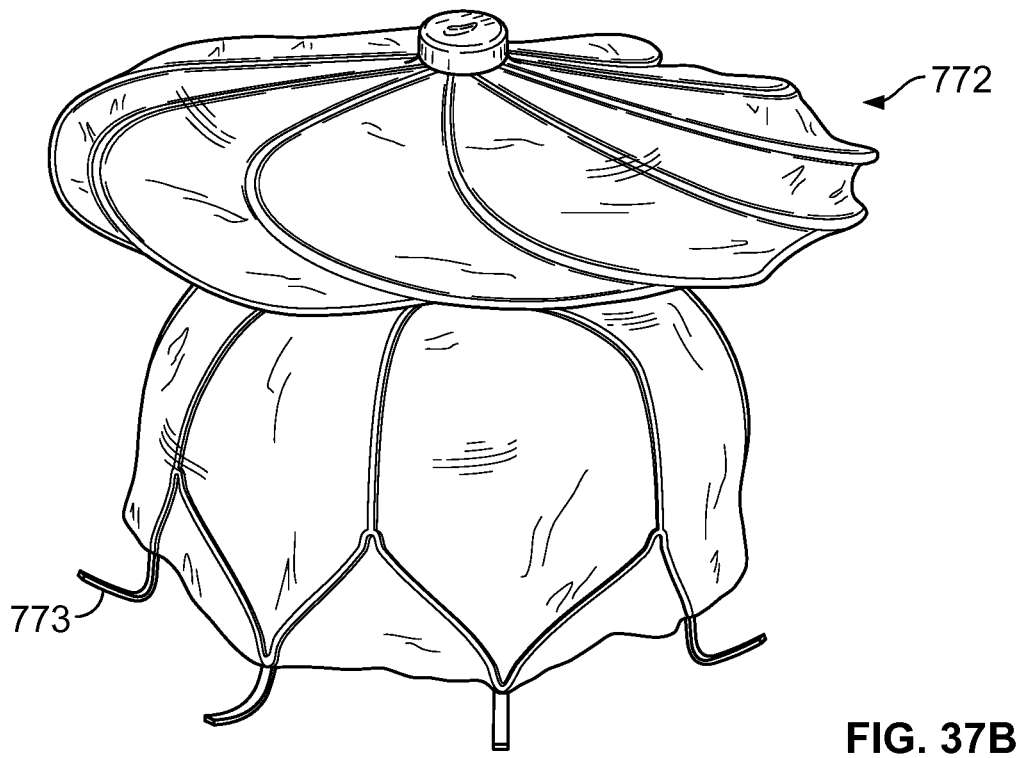
FIG. 37B is a perspective view of another example occlusive device in accordance with embodiments provided herein.

FIG. 37B is another example occlusive device 772. The occlusive device 772 includes free ends 773 that extend from the cells of the anchor frame. In some embodiments, the free ends 773 are angled generally radially and include ball-ends. It should be understood that any of the other types of free ends described herein (e.g., refer to FIGS. 16A-16D) may be substituted for the free ends 773. In addition, in some embodiments a combination or sub-combination of types of anchors and/or types free ends can be included on a single occlusive device. For example, the mid-point anchors of occlusive device 770 can be combined with the distally located ball-end anchors of occlusive device 772.

Figure 37C:
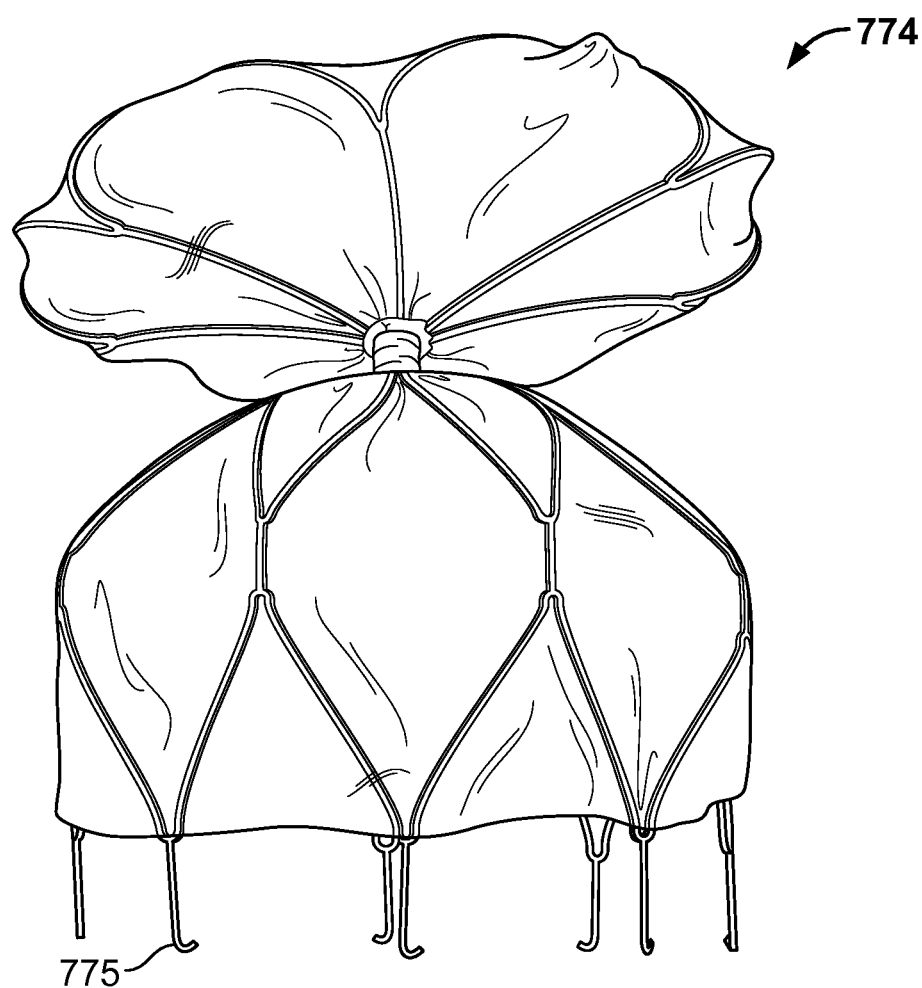
FIG. 37C is a perspective view of another example occlusive device in accordance with embodiments provided herein.

FIG. 37C is another example occlusive device 774. The occlusive device 774 includes free ends 775 that extend from the cells of the anchor frame. In some embodiments, the free ends 775 are curled to provide atraumatic free ends 775. It should be understood that any of the other types of free ends described herein (e.g., refer to FIGS. 16A-16D) may be substituted for the free ends 775.

Figure 38:
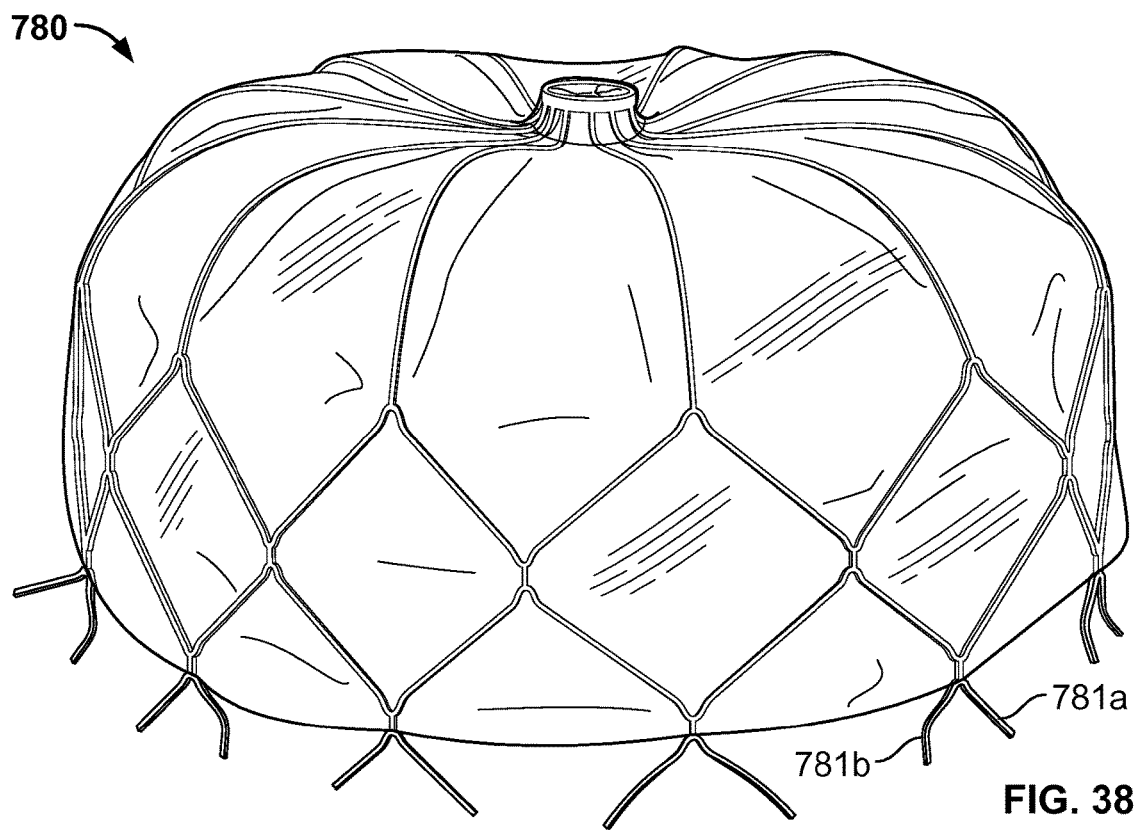
FIG. 38 is a perspective view of another example anchor frame that can be used with embodiments of the occlusive devices provided herein.

FIG. 38 is another example of an anchor frame 780. The anchor frame 780 is generally cylindrical. This anchor frame 780 can be used in conjunction with any of the disc-shaped occlusion frame portions described herein. Anchor frame 780 includes double free ends 781a and 781b extending from the distal end of each cell of the distal-most row of cells. It should be understood that any of the other types of free ends described herein (e.g., refer to FIGS. 16A-16D) may be substituted for the free ends 773.

Figure 39A:
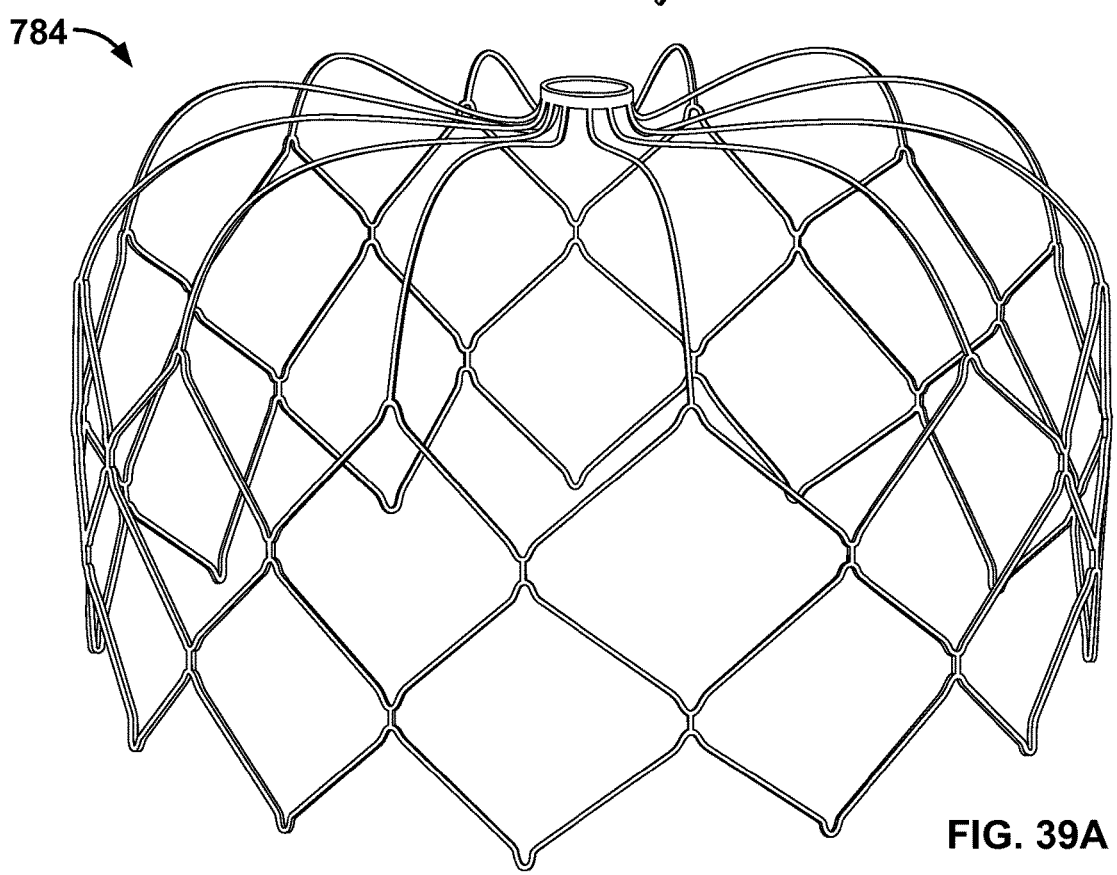
FIG. 39A is a perspective view of the frame of another example anchor frame that can be used with embodiments of the occlusive devices provided herein.
Figure 39B:
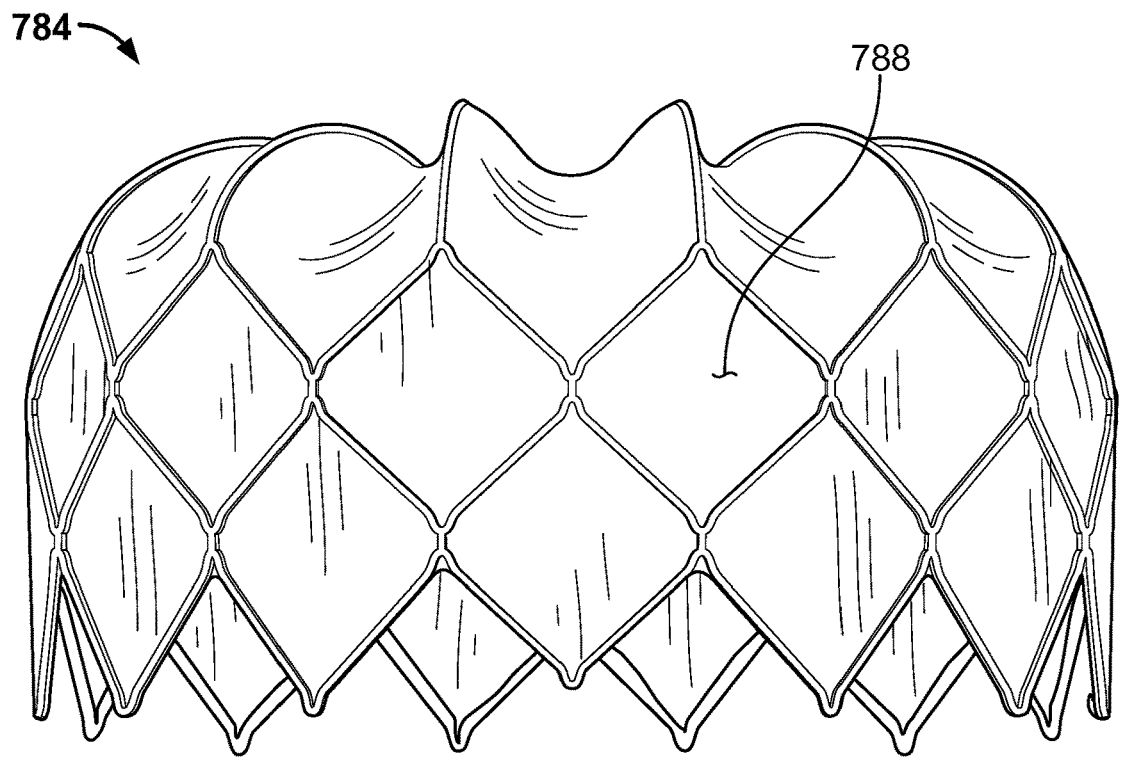
FIG. 39B is a perspective view of the frame of FIG. 39A with the addition of a covering component.
Figure 40:
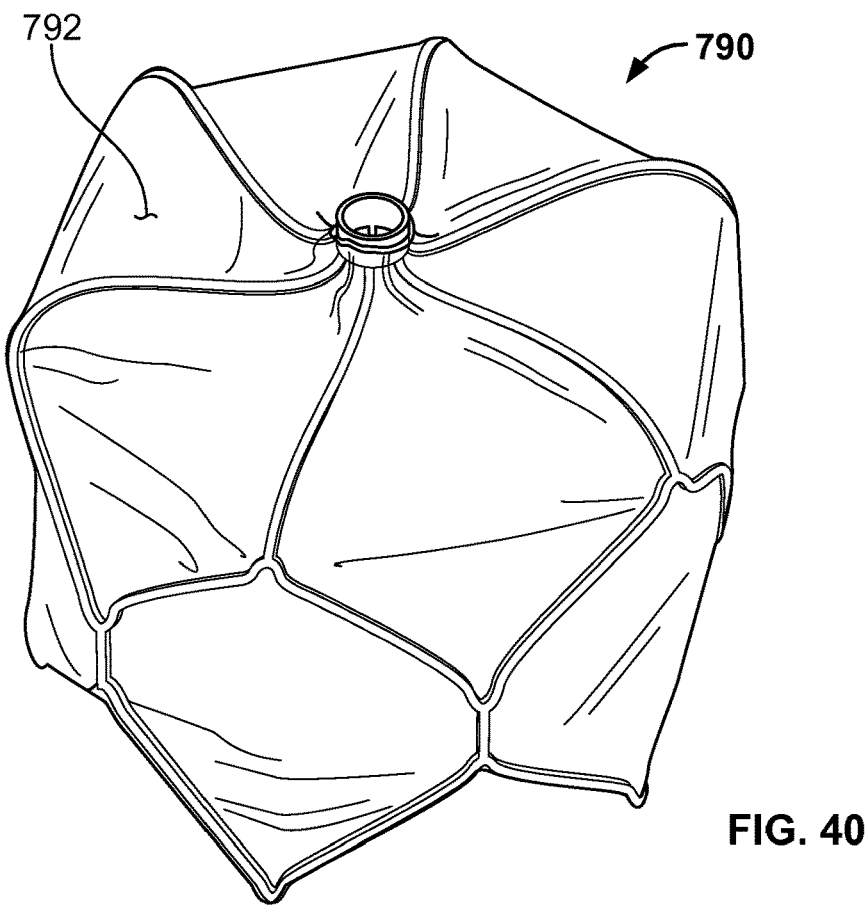
FIG. 40 is a perspective view of another example anchor frame that can be used with embodiments of the occlusive devices provided herein.
Figure 41A:
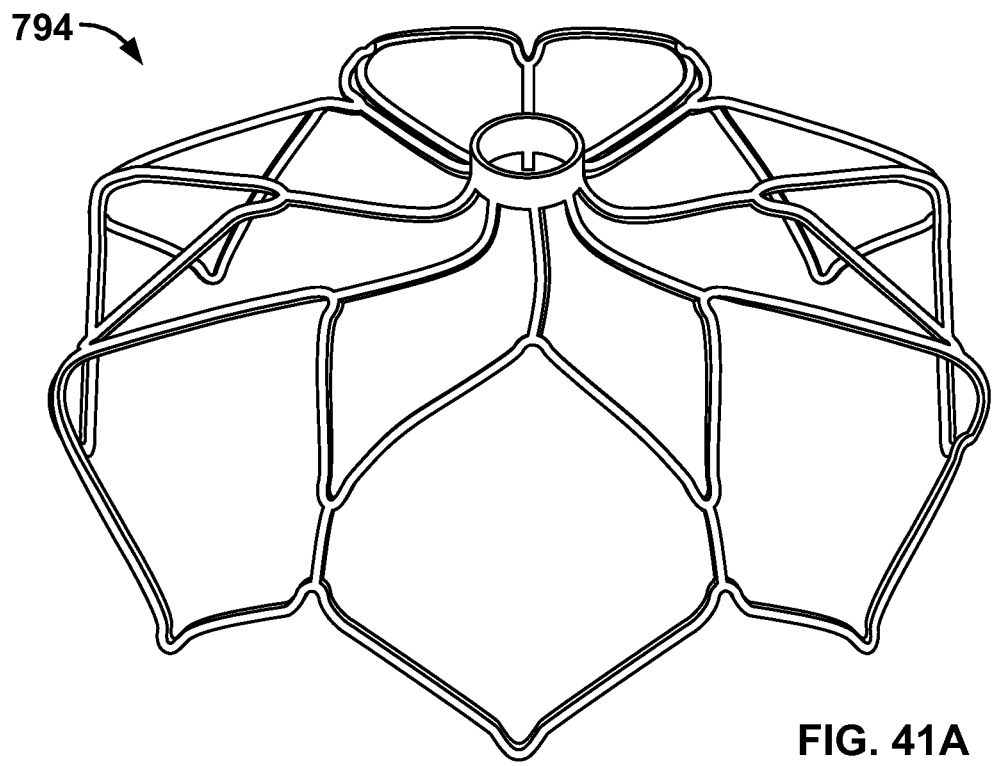
FIG. 41A is a perspective view of the frame of another example anchor frame embodiment that can be used with some embodiments of the occlusive devices provided herein.
Figure 41B:
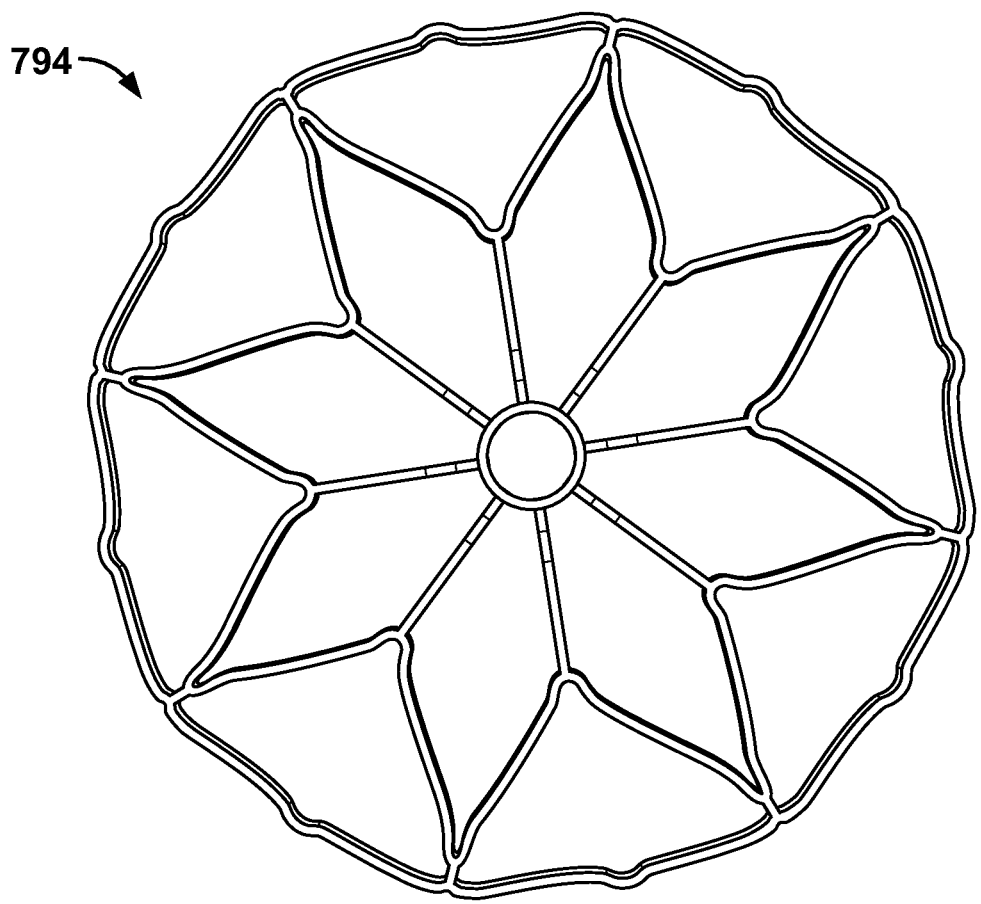
FIG. 41B is an end view of the frame of FIG. 41A.

FIGS. 39A and 39B are another example of an anchor frame 784, shown as an uncovered frame and a covered frame, respectively. The anchor frame 784 includes a covering component 788 in FIG. 39B. This provides an example of how, in some embodiments, the covering component 788 can be tailored to terminate with the diagonal pattern of the ends of the distal-most cells. In FIG. 39A, a cupping or concavity at the proximal end (the top as viewed in FIG. 39A) of the anchoring frame 784 is shown. In some embodiments, when implanted in a patient such cupping can advantageously create an axial bias towards the occlusive disc member, and to reduce the spacing between the anchor frame and the occlusive disc-shaped member. This configuration can help to seal the occlusive device to the surrounding tissue by keeping the occlusive device biased toward the ostium after the anchors are set. This cupping is also seen in FIGS. 40, 41A, and 41B, and can be incorporated with any of the occlusive devices provided herein. FIG. 40 is another example of an anchor frame 790 with a covering component 792 that is tailored to terminate with the diagonal pattern of the ends of the distal-most cells.

FIGS. 41A and 41B are a perspective view and an end view of another example anchor frame 794. This embodiment of anchor frame 794 has a structure that can provide a substantial radial force to surrounding tissue to thereby resist device migration.

Referring now to FIGS. 42 through 49, as described previously, the occlusive devices provided herein can be used to occlude spaces, holes, defects, apertures, appendages, vessels or conduits within a body of a patient. As will be explained further, FIGS. 42 through 49 provide example occlusive device embodiments that are especially well-suited to occluding holes, apertures, and other such tissue defects so as to inhibit the passage of body materials. For example, the occlusion and sealing of an opening (e.g., a hole, perforation, tear, fistula, etc.) of a body conduit such as the colon, blood vessels, intestines, and other body conduits can be treated using such devices and techniques. In such cases, the occlusive device can inhibit the passage of body materials (e.g., fecal matter, bile, digestive fluids, blood, thrombus, and the like).

The example occlusive devices of FIGS. 42-49 are well-suited for use in the gastrointestinal (GI) tract, and other areas. For example, the devices can be used to occlude and seal a lumen wall opening resulting from an endoscopic full thickness resection (EFTR). In addition, in some embodiments the devices can be used to treat a gastrointestinal fistula or diverticulum. The use of occlusive devices in the environment of the GI tract calls for occlusive devices that provide substantially continuous lumen wall contact with apposition force for effective occlusion performance during peristaltic motion. Peristaltic motion can result in the application of large dynamic, asymmetric, and non-planar displacements to the occlusive devices in some circumstances, as well as normal and shear stresses from material transport. In some embodiments, the occlusive devices provided herein provide substantially continuous lumen wall contact with conformability and apposition force for effective occlusion and sealing performance during such conditions caused by peristaltic motion. In addition, the intra-lumenal and extra-lumenal pressures in the GI tract are often unbalanced, so the occlusive devices provided herein are resistant to such a pressure gradient. In some embodiments, the occlusive devices provided herein substantially do not interfere with the healing response of the body, to allow the defect area in the GI tract to close (heal). In some embodiments, the occlusive devices provided herein are removable after the defect area has healed. Therefore, in some such embodiments the occlusive devices are configured to not allow tissue ingrowth and are designed for atraumatic withdrawal. For example, in some embodiments the occlusion device's provision of apposition force without the use of barbs or prongs allows the device to resist migration, seal, and be safely removed. Further, in some embodiments the occlusive devices provided herein also have low profiles to reduce risk of puncture, adhesion, or stricture of the GI tract lumen or surrounding organs.

Figure 42:
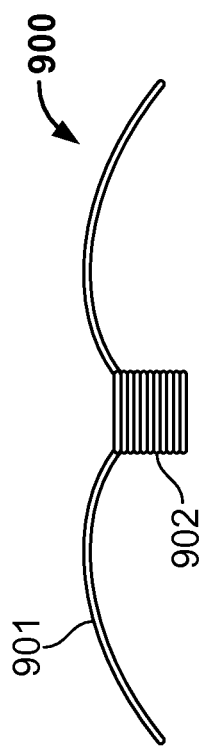
FIG. 42 is a side view illustration of a portion of another example occlusive device in accordance with embodiments provided herein.

FIG. 42 is a side view of one portion 900 of a two-part occlusive device that is well-suited for use in the GI tract and other areas. In some embodiments, the other portion of the two-part device (not shown) may be configured the same as portion 900, except the hubs may include dissimilar structures by which the portions of the two-part device can couple together. However, in some embodiments the portions of a two-part device are configured differently, and may include differences such as, but not limited to, diameters of the elongate members, patterns of the elongate members, coverings on the portions, and the like. In some embodiments, the portion 900 may be symmetrical, and in some embodiments the portion 900 may be asymmetrical.

In some embodiments, the portion 900 of the two-part occlusive device includes a frame 901 formed of elongate members, and an eyelet 902 that is formed of the same elongate members of the frame 901. In some embodiments, the eyelet 902 is a different type of hub, such as a ring, crimp collar, tube, and the like. In some embodiments, the portion 900 may be formed from a single elongate member. In some embodiments, more than one elongate member is used to form the frame 901. The elongate members terminate at the eyelet 902. The elongate members may be formed from any of the frame materials described elsewhere herein. In some embodiments, a ring hub may be used instead of the spiral-wound eyelet 902. In some embodiments, the portion 900 may be made from a cut tube or planar material.

The frame 901 includes a dish-shaped profile. As will be described later, the dish-shaped profile helps to establish and maintain a resilient and compliant seal of the defect being treated, and to resist device migration.

Figure 43C:
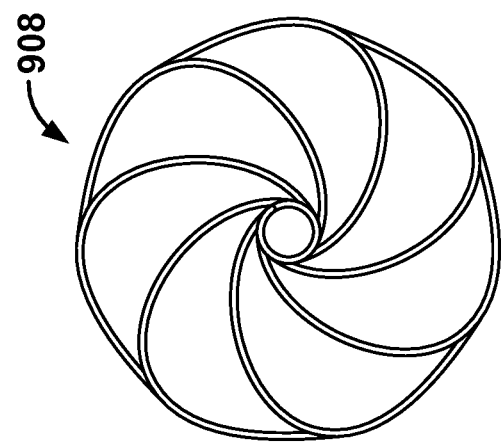
FIG. 43C is an end view illustration of another example design of the occlusive device portion of FIG. 42.
Figure 43B:
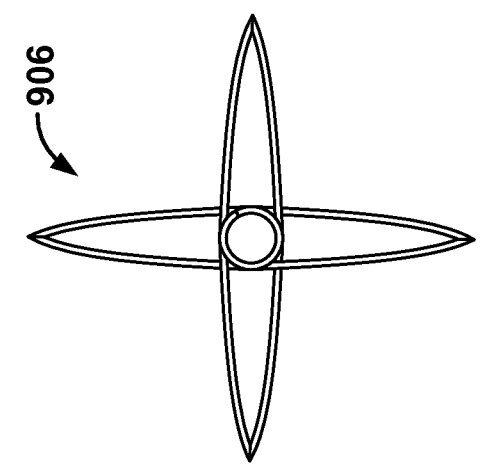
FIG. 43B is an end view illustration of another example design of the occlusive device portion of FIG. 42.
Figure 43A:
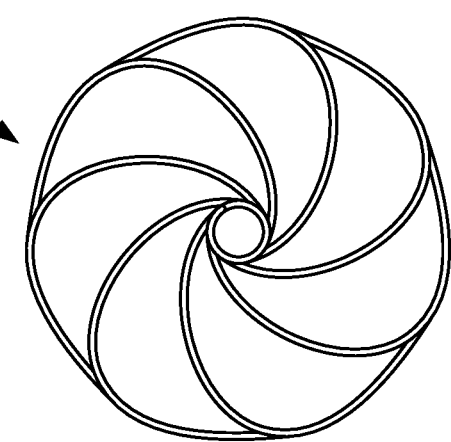
FIG. 43A is an end view illustration of an example design of the occlusive device portion of FIG. 42.

FIGS. 43A through 43C show alternative frame patterns 904, 906, and 908. The frame patterns of any of the disc-shaped members described elsewhere herein may be used for the frame 900. For example, pattern 904 includes petal-shaped spokes and a circumferential member; pattern 906 includes petals that do not overlap; and pattern 908 includes overlapping petals. It should be understood that these frame patterns are non-limiting examples, and various other types of frame patterns (including, ovular, oblong, non-circular, irregular, non-uniform and asymmetrical shapes) are within the scope of this disclosure.

In some embodiments, the frame patterns include two or more elongate members that can have different cross-sectional diameters. The use of such elongate members with dissimilar diameters can be used advantageously to provide suitable bending stiffness properties in particular portions of the frame. For example, elongate members with dissimilar diameters can be used to construct a disc frame with overlapping petals where one or more petals are made with larger diameter wire than others such that the disc frame has a lower bending force in one plane versus another. The same result can be accomplished with an elongate member of variable diameter along its length so that areas of larger or smaller diametrical cross-section can be strategically placed to provide differing bending strength in different planes. Therefore, in some embodiments the elongate members making up the frame can have a variable diameter. That is, a first portion of an elongate member may have a small diameter than another portion of the same elongate member.

In some embodiments, at least one of the portions of the two-part occlusive device includes a covering component. For example, the portion of the two-part occlusive device that is on the inside of a conduit (e.g., the colon) may have a covering component. In some embodiments, both portions of the two-part occlusive device include a covering component, while in other embodiments just one portion of the two-part device includes a covering component (e.g., refer to FIG. 46).

FIGS. 44A through 44D illustrate an example deployment process of a two-part occlusive device 910 to occlude a tissue opening 909. The first and second portions 912 and 914 can be collapsed to low-profile configurations and loaded into a delivery sheath 911. The distal end portion of the delivery sheath 911 can be positioned within the opening 909.

Each of the first and second portions 912 and 914 can be attached to a control catheter 913 and 915 respectively. In some embodiments, the control catheters 913 and 915 are configured co-axially. The control catheters 913 and 915 allow independent axial and rotational control of the position of the first and second portions 912 and 914. In some embodiments, the control catheters 913 and 915 can also be used to transport fluid, adhesives, energy, and the like.

Figure 44A:
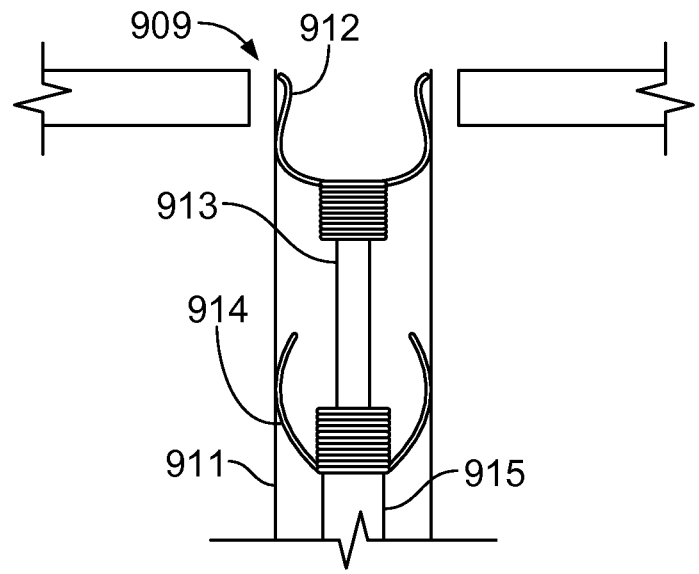
FIGS. 44A-44D are a series of illustrations depicting the deployment of an example occlusive device in accordance with embodiments provided herein.
Figure 44B:
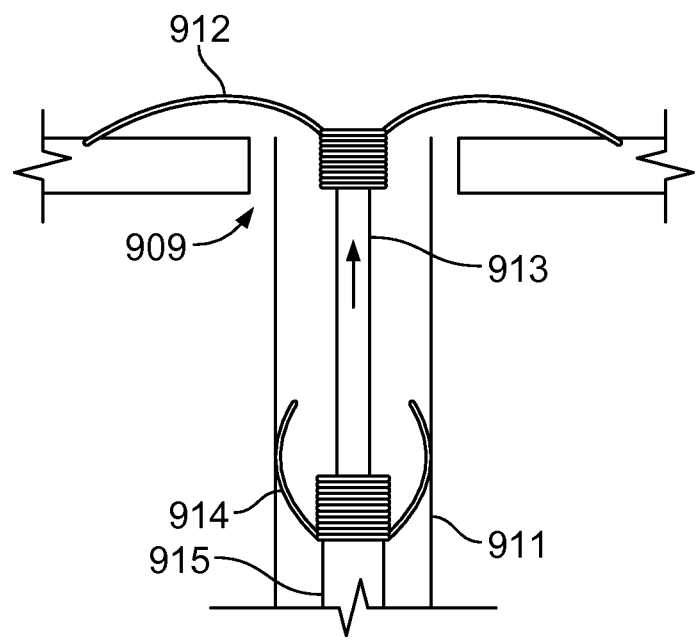
Figure 44C:
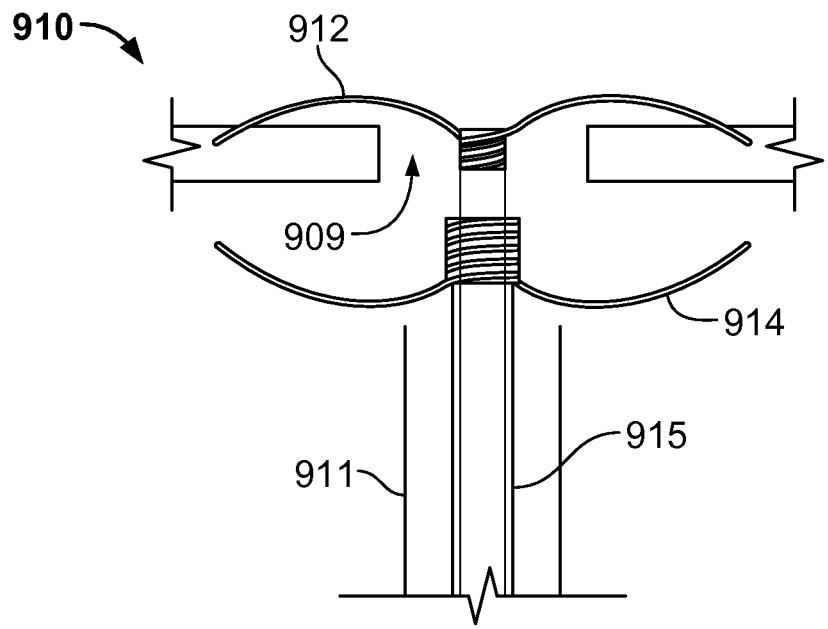
Figure 44D:
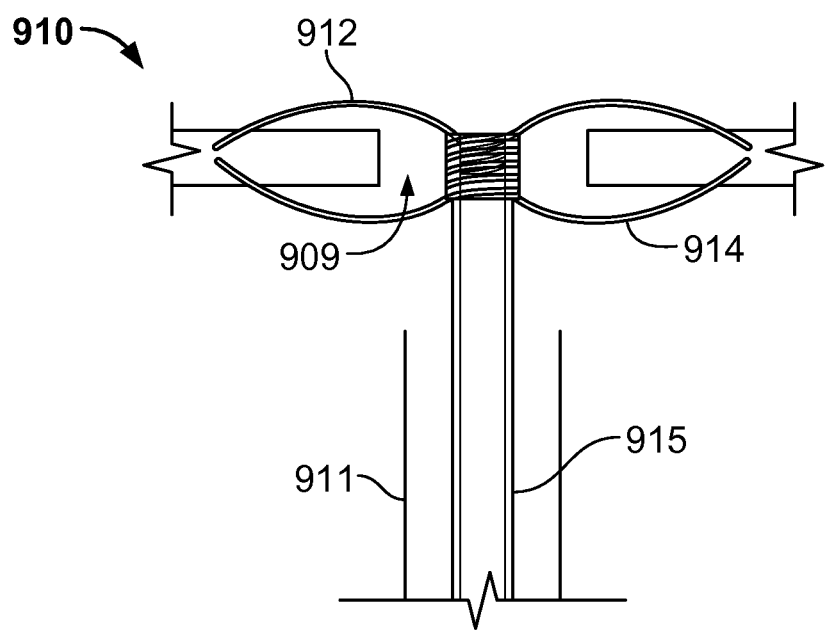

The first portion 912 can be deployed by pushing the control catheter 913 distally as shown in FIG. 44B. The second portion 914 can be deployed by pushing the control catheter 915 distally and retracting the delivery sheath 911 as shown in FIG. 44C. In FIG. 44D, the eyelets of the first and second portions 912 and 914 are engaged together such that the first and second portions 912 and 914 are interlocked. In that configuration, the first and second portions 912 and 914 are clamping the tissue and sealing the opening 909. Then the control catheters 913 and 915 can be disengaged from the first and second portions 912 and 914, and the control catheters 913 and 915 and delivery sheath 911 can be withdrawn from the patient.

Figure 45A:
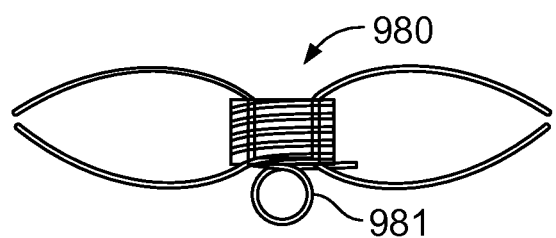
FIGS. 45A-45C are examples of design configurations whereby the hubs of some occlusive device embodiments provided herein can be coupled together.
Figure 45B:
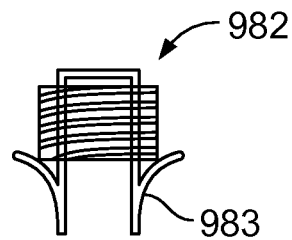
Figure 45C:
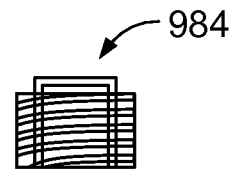

FIGS. 45A through 45C provide examples techniques for coupling the eyelets (or other types of hubs such as rings, tubes, crimp collars, and the like, in some embodiments) of the first and second portions of a two-part occlusive device together. In FIG. 45A, the first and second eyelets can be coupled to form an assembly 980 using a lock loop 981. In some embodiments, the lock loop can be made of a superelastic material such as NiTi. In FIG. 45B, the eyelets are locked together to form an assembly 982 using barbs 983 that are disposed on one or both of the eyelets. In FIG. 45C, the eyelets are coupled together to form an assembly 984 using a frictional or interference fit. In other embodiments, threaded engagement, magnetic engagement, and adhesives can be used. In some embodiments, heat by way of electrical resistance, or RF, can be delivered down the control catheter to weld the eyelets together.

Figure 46:
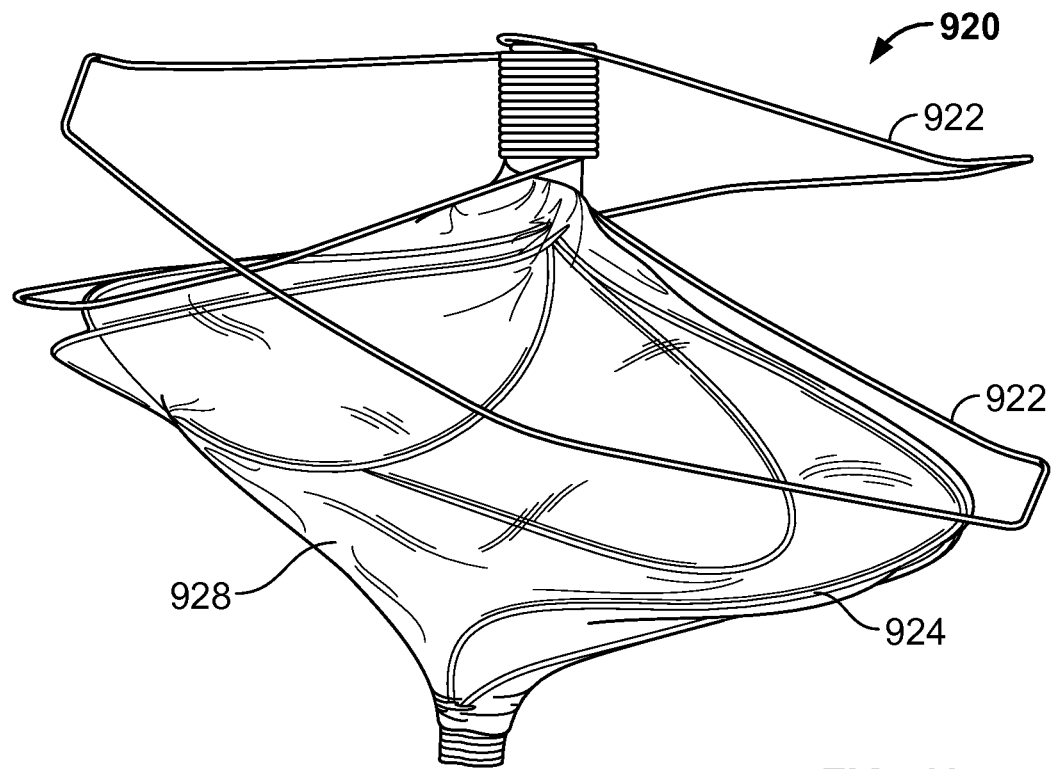
FIG. 46 is a perspective view of another example occlusive device in accordance with embodiments provided herein.

FIG. 46 provides an example two-part occlusive device 920. The two-part occlusive device 920 includes a first portion 922 and a second portion 924. In this example, the first portion 922 does not include a covering component and the second portion 924 does include a covering component 928. The eyelets of the first and second portions 922 and 924 are concentrically interlocked.

Figure 47A:
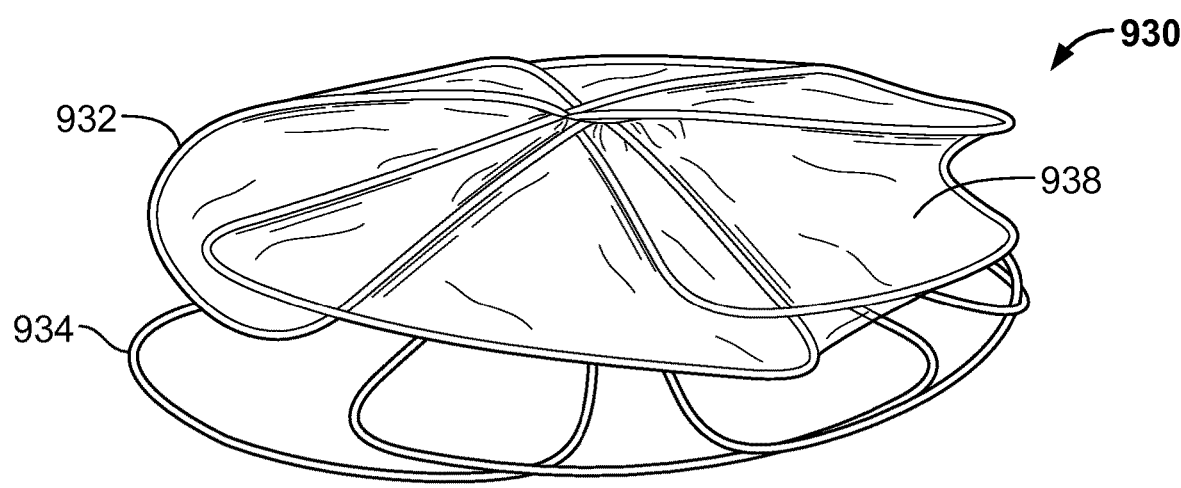
FIG. 47A is a perspective view of another example occlusive device in accordance with embodiments provided herein.
Figure 47B:
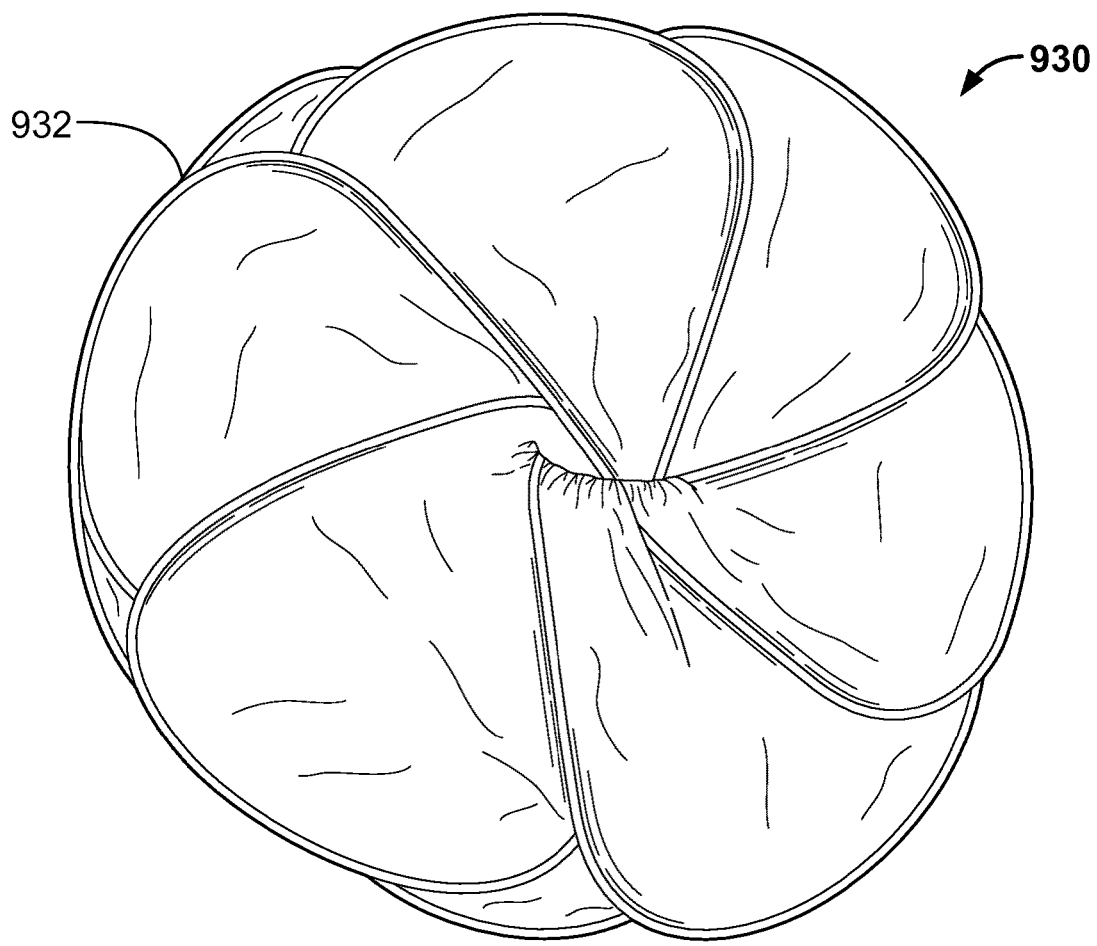
FIG. 47B is an end view of the occlusive device of FIG. 47A.

FIGS. 47A and 47B provide another example of a two-part occlusive device 930 in perspective views and end views respectively. A first portion 932 includes a covering component 938 disposed on the frame of the first portion 932. The frame of the first portion 932 is comprised of overlapping petals. The hub of the first portion 932 is interlocked with the hub of the second portion 934. The second portion 934, in this example embodiment 930, does not include a covering component. The frame of the second portion 934 is also comprised of overlapping petals.

Figure 48:
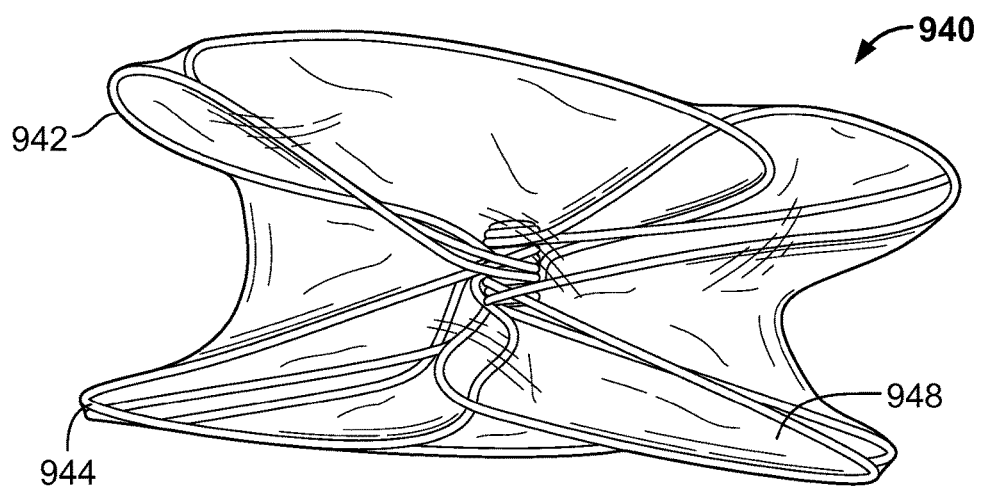
FIG. 48 is a side view of another example occlusive device in accordance with embodiments provided herein.

FIG. 48 is another example two-part occlusive device 940 in accordance with some embodiments provided herein. Both portions 942 and 944 of the two-part occlusive device 940 include a covering component 948, and have frames comprised of overlapping petals.

Figure 49:
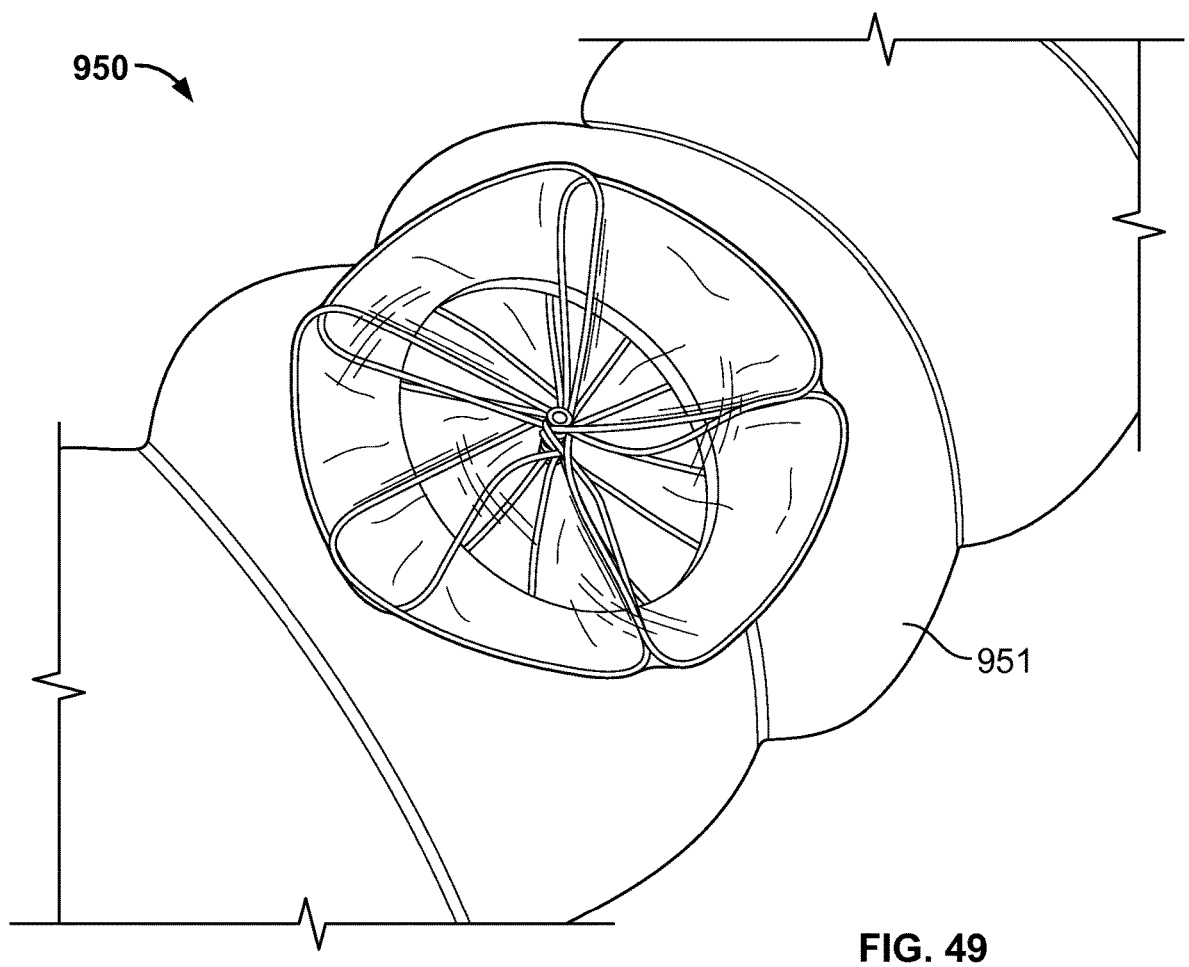
FIG. 49 is a depiction of an occlusive device deployed in a body conduit to seal an opening in the conduit.

FIG. 49 shows an example two-part occlusive device 950 that has been implanted to seal an opening in the wall of a body conduit 951. As shown, the outer diameter of the portion of the two-part sealing device 950 that includes a covering component is larger than the size of the opening. The second portion of the two-part sealing device 950 is inside of the body conduit 951 and therefore not visible in this view. The second portion may also include a covering.

Figure 50A:
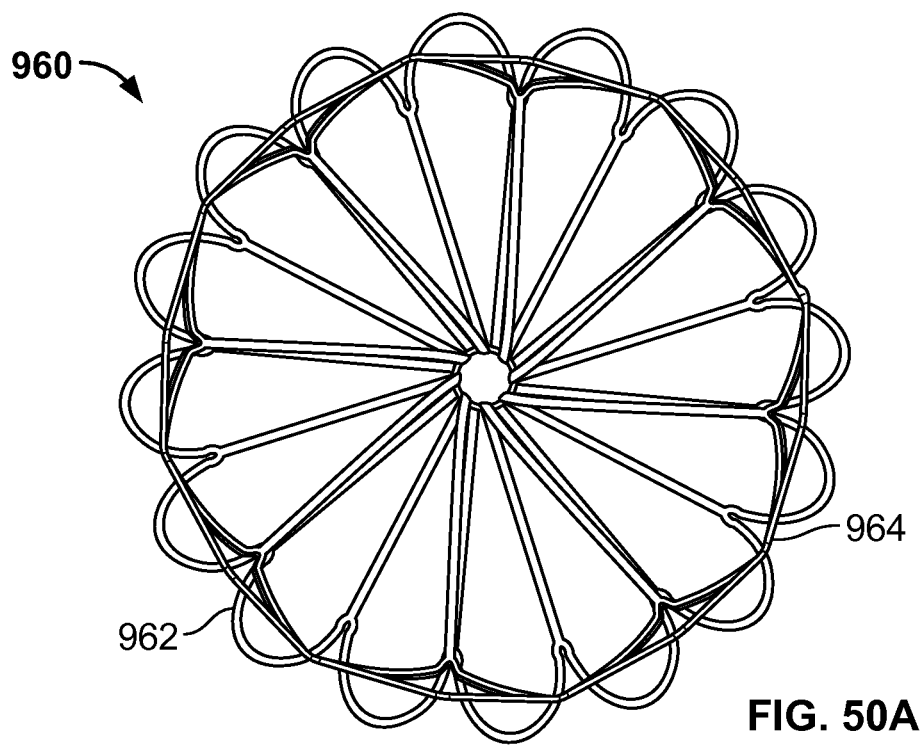
FIG. 50A is a top view of a frame of another example occlusive device embodiment.
Figure 50B:
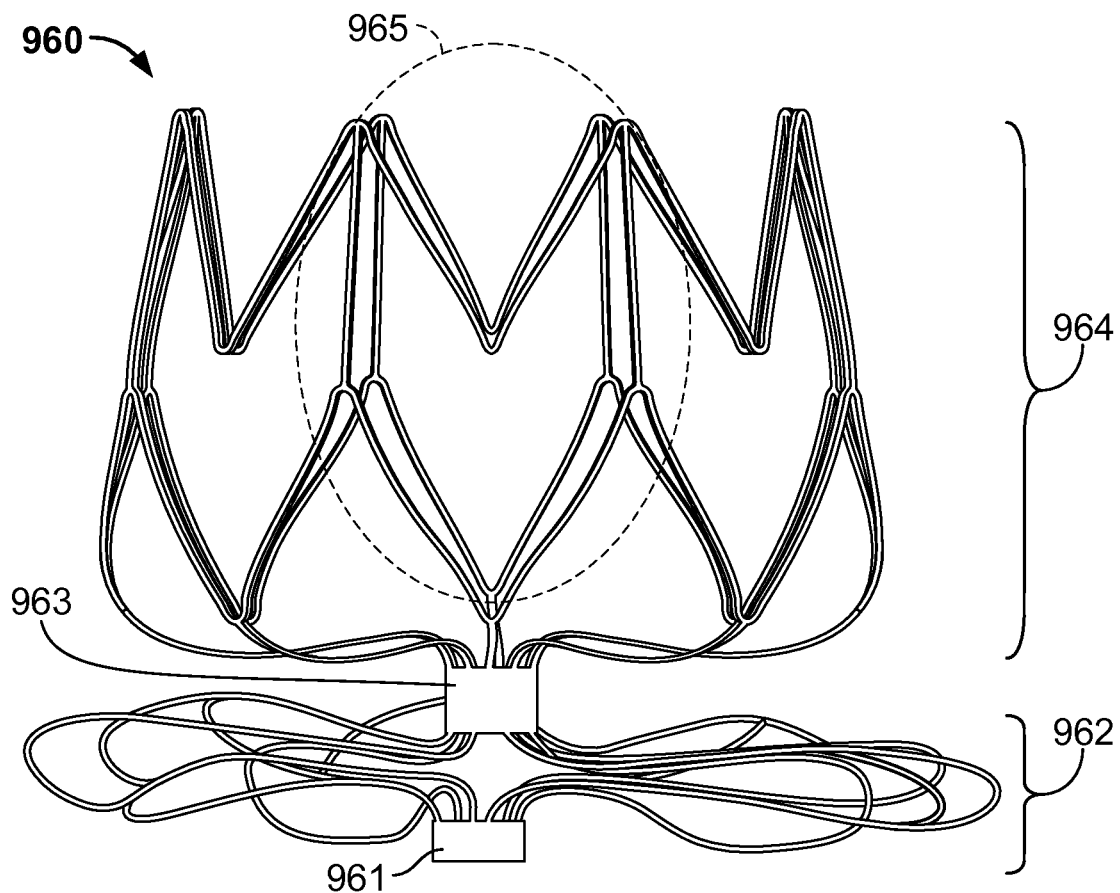
FIG. 50B is a side view of the frame of the occlusive device of FIG. 50A.
Figure 50C:
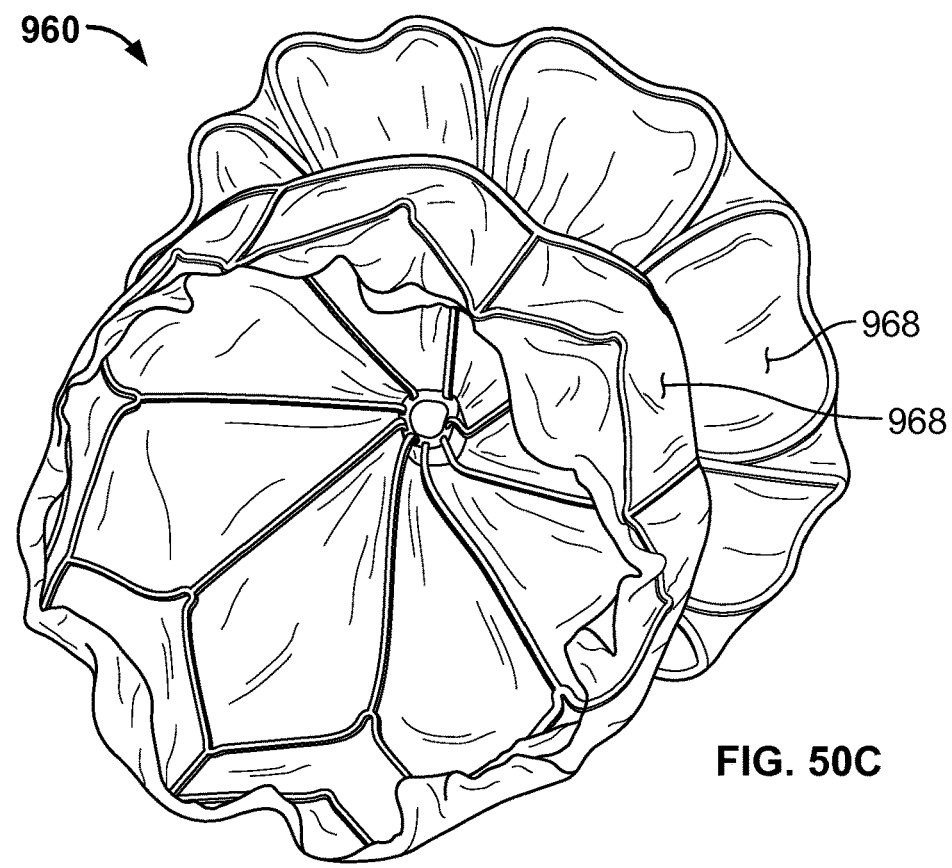
FIG. 50C is a top perspective view of the occlusive device of FIG. 50A with a covering component on the frame.
Figure 50D:
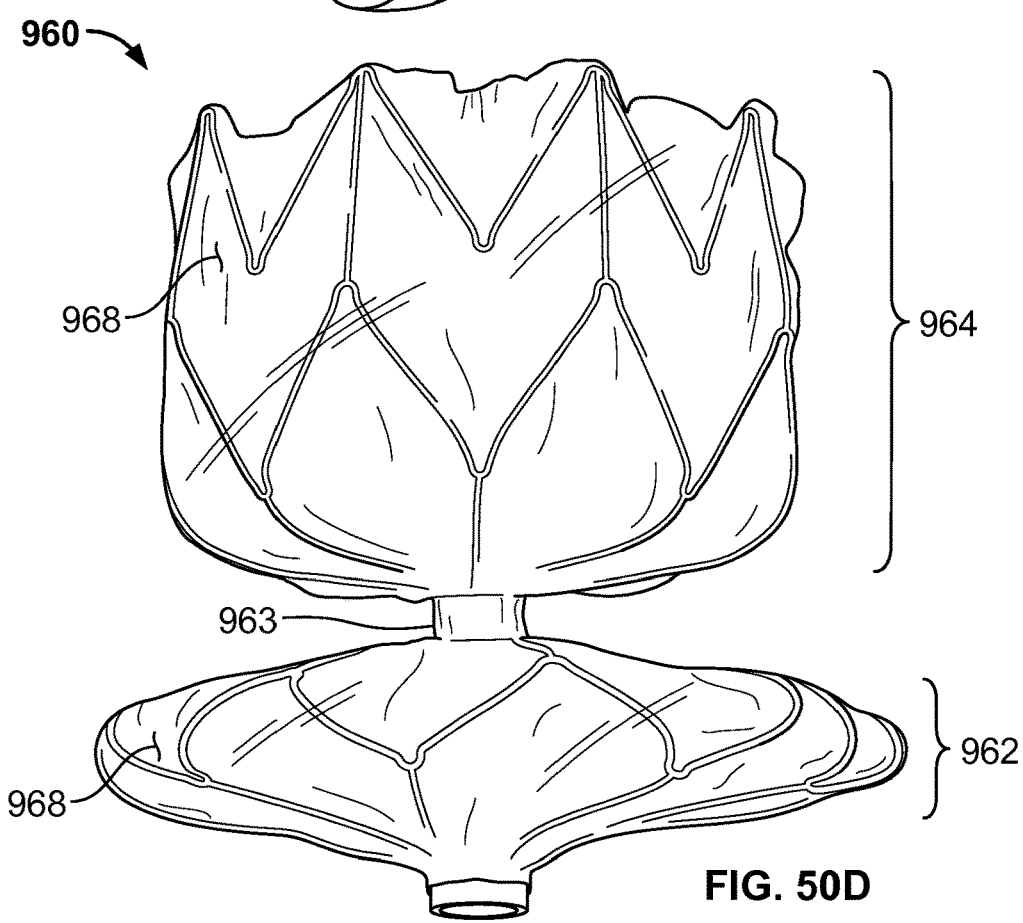
FIG. 50D is a side view of the occlusive device of FIG. 50A with a covering component on the frame.

FIGS. 50A through 50D are illustrations of another example occlusive device 960 that can be used to occlude a hole, defect, aperture, or appendage within a body of a patient. FIGS. 50A (top view) and 50B (side view) show the two sub-frames: an occlusion frame 962 (or disc-shaped member) and an anchor frame 964. FIGS. 50C (top perspective view) and 50D (side view) show the frames 962 and 964 of the occlusive device 960 with a covering component 968.

In some embodiments, the occlusion frame 962 and the anchor frame 964 are formed from the same piece of precursor material. For example, in some embodiments the occlusion frame 962 and the anchor frame 964 can be formed from a single tube or sheet of material that is cut and expanded to form the frame configurations of the occlusion frame 962 and the anchor frame 964. In some such embodiments, the occlusion frame 962 and the anchor frame 964 are a unitary member. In some such embodiments, the occlusion frame 962 and the anchor frame 964 are a seamless member. In some embodiments, the unitary construct of the occlusive device 970 can include anchor features. Such frame construction techniques can also be used for the formation of the other occlusive devices provided herein. In some embodiments, frames 962 and 964 can be formed from wound elongate member such as wires. Hubs, such as rings, crimp collars, eyelets and the like, can be incorporated into the frame construct. Such frame construction techniques can also be used for the formation of the other occlusive devices provided herein. In some embodiments, the occlusive devices provided herein include a combination of types of frame constructs in a single occlusive device. For example, a portion of the frame of an occlusive device can be formed by cutting and expanding a material, and another portion of the frame can be made from one or more wires that may or may not be attached to a hub or hubs (wherein hubs include, but are not limited to, eyelets, rings, crimp collars, and the like).

While the device frames discussed herein are generally described with reference to occlusion applications, for filtering applications where substantial occlusion is not desired, the occlusion frame may be referred to as a filter frame. That is, any of the described occlusion frames may also be filter frames, for example.

The occlusion frame 962 is another example of a non-petal shaped disc-shaped occlusive frame. The construction of example occlusion frame 962 is as follows. Elongate members extend from the proximal hub 961 of the occlusion frame 962. The elongate members bifurcate at about the axial midpoint between the proximal hub 961 and the connecting hub 963. Each of the bifurcated branch elongate members then joins with another elongate member that extends to the connecting hub 963. This construction of the occlusion frame 962 provides a highly stable structure that is conformable to the topography of surrounding tissue and is resistant to malformations of the occlusion frame 962 during deployment and in situ. The example occlusion frame 962 does not include petals. Other types of occlusion frame constructs that also do not include petals are also envisioned within the scope of this disclosure, and occlusion frame 962 is one example of such.

The occlusion frame 962 is a conformable member. That is, the occlusion frame 962 can readily conform in shape to the topography of the anatomy surrounding the anchor frame 962 at the implant site. In addition, the anchor frame 964 is a conformable member. That is, the shape of the anchor frame 964 can readily conform and assimilate to the topography of the anatomy surrounding the anchor frame 964 at the implant site.

In some embodiments, the example anchor frame 964 includes a chevron-shaped cell structure 965, as shown in FIG. 50B. This structure provides a conformable and stable anchor frame 962. The chevron-shaped cell structure 965 can also facilitate collapsing the anchor frame 962 to a low-profile for placement within a delivery sheath. In some embodiments, the anchor frame 964 can have one or more rows of chevron-shaped cells. In the depicted embodiment, one row of chevron-shaped cells is included. In some embodiments, two, three, four, five, six, or more than six rows of chevron-shaped cells are included. The anchor frame 964 is a conformable member. That is, the shape of the anchor frame 964 can readily conform and assimilate to the topography of the anatomy surrounding the anchor frame 964 at the implant site. In some embodiments, the anchor frame 964 is generally cylindrical. In some embodiments, the anchor frame 964 can include a combination of shapes of cell structures. For example, a single occlusive device can include two or more shapes of cell structures (e.g., diamond-shaped, chevron-shaped, hexagonal, and the like).

In some embodiments, the occlusive device 960 includes a covering component 968 that covers some or all of the occlusion frame 962. In this example, the covering component 968 covers the occlusion frame 962 and is attached to portions of the elongate frame members of the occlusion frame 962. In some embodiments, the covering component 968 is at least partially attached to portions of the elongate frame members using an adhesive, such as but not limited to FEP. In some embodiments, portions of the covering component 968 can be attached to the elongate members by banding the covering component 968 thereto, such as at hubs 961 and 963. The banding can be a variety of materials, including but not limited to biocompatible film materials, suture materials, metallic materials, and the like, and combinations thereof. Such attachment materials and techniques can also be used for other embodiments of the occlusive devices provided herein.

In some embodiments, the covering component 968 is attached to selected regions of the occlusion frame 962 (and other portions such as the anchor frame 964) and not attached to other regions of the occlusion frame 962. This technique can facilitate enhanced conformability of the occlusive device 960 to the topography of a patient's anatomy at the implant site. Such techniques can also be used with other embodiments of the occlusive devices provided herein.

The covering component 968 is configured to modulate, and in some examples, filter, or substantially inhibit the passage of blood and/or thrombus through the covering component 968. Some embodiments include a covering component 968 that is configured to induce rapid tissue ingrowth and to occlude the passage of blood and/or thrombus through the covering component. The covering component 968 may be a porous, elastic member that can stretch and collapse to accommodate extension and collapse, respectively, of the elongate frame members. Pores of the covering component 968 may be sized to substantially, or in some examples completely, prevent passage of blood, other bodily fluids, thrombi, and emboli. The covering component 968 can have a microporous structure that provides a tissue ingrowth scaffold for durable occlusion and supplemental anchoring strength of the occlusion device 960. Some embodiments of the covering component 968 comprise a fluoropolymer, such as an expanded polytetrafluoroethylene (ePTFE) polymer. In some embodiments, the covering component 968 can be a membranous covering. In some embodiments the covering component 968 can be a film. In some embodiments, the covering component 968 can be a filtering medium.

In some embodiments, the covering component 968 is configured such that the modulation of fluid passage through the covering component 968 is immediate and does not rely on a thrombotic process. In some embodiments, the covering component 968 can be modified by one or more chemical or physical processes that enhance certain physical properties of the covering component 968. For example, a hydrophilic coating may be applied to the covering component 968 to improve the wettability and echo translucency of the covering component 968. In some embodiments, the covering component 968 may be modified with chemical moieties that promote one or more of endothelial cell attachment, endothelial cell migration, endothelial cell proliferation, and resistance to thrombosis. In some embodiments, the covering component 968 may be modified with covalently attached heparin or impregnated with one or more drug substances that are released in situ to promote wound healing or reduce tissue inflammation. In some embodiments, the drug may be a corticosteroid, a human growth factor, an anti-mitotic agent, an antithrombotic agent, or dexamethasone sodium phosphate.

In some embodiments, covering component 968 is pre-perforated to modulate fluid flow through the covering component, to create filtering properties, and/or to affect the propensity for tissue ingrowth to the covering component 968. In some embodiments, the covering component 968 is treated to make the covering component 968 stiffer or to add surface texture. For example, in some embodiments the covering component 968 is treated with FEP powder to provide a stiffened covering component 968 or roughened surface on the covering component 968. In some embodiments, selected portions of the covering component 968 are so treated, while other portions of the covering component 968 are not so treated. Other covering component 968 material treatment techniques can also be employed to provide beneficial mechanical properties and tissue response interactions. Such materials and techniques can be used for any of the occlusive devices provided herein.

In some embodiments, the covering component 968 may be formed of a fluoropolymer (e.g., expanded PTFE (ePTFE) or PTFE). In some embodiments, the covering component 968 may be formed of a polyester, a silicone, a urethane, or another biocompatible polymer, or combinations thereof. In some embodiments, bioresorbable or bioabsorbable materials may be used, for example a bioresorbable or bioabsorbable polymer. In some embodiments, the covering component 968 can comprise Dacron. In some embodiments, the covering component 968 can comprise knits or fibers. The covering component 968 may be woven or non-woven in various embodiments. In some embodiments, the covering component 968 may be formed of a copolymer. In some examples, a first portion of the covering component 968 may be formed of a first material and a second portion of the covering component 968 may be formed of a second material. For example, the portion of the covering component 968 that covers the occlusion frame 962 of the device may be comprised of a first material, and a portion of the covering component 968 that covers the anchor frame 964 of the device may be comprised of a second material.

FIGS. 51-53, 55-58, and 60 illustrate additional example occluder devices 970, 980, 990, 1010, 1020, 1030, 1040, and 1060 respectively. In some embodiments, the occluder devices 970, 980, 990, 1010, 1020, 1030, 1040, and 1060 can serve as anchor frames in a manner like that of anchor frames 780, 784, 790, and 794 of FIGS. 38, 39B, 40, and 41A. In some such embodiments, the occluder devices 970, 980, 990, 1010, 1020, 1030, 1040, and 1060 can coupled to any of the occlusion frames described herein to provide occluder devices that include an occlusion frame and an anchor frame (e.g., refer to FIGS. 33B, 36A, 37B, 37C, and 50D). Any of the mechanisms described herein for coupling an occlusion frame with an anchor frame can be used to couple the occluder devices 970, 980, 990, 1010, 1020, 1030, 1040, and 1060 to any of the occlusion frames provided herein. For example, such coupling mechanisms include, but are not limited to, a unitary connecting hub (e.g., connecting hub 765 of FIG. 35B), a flexible connector (e.g., flexible connector 314 of FIG. 20), a flexible linkage (e.g., flexible linkage 406 of FIG. 22A), a nested hub/ring arrangement (e.g., FIG. 26), and so on, and combinations of such mechanisms.

In some embodiments, the occluder devices 970, 980, 990, 1010, 1020, 1030, and 1060 as shown can serve as occluder devices in and of themselves. As such, the occluder devices 970, 980, 990, 1010, 1020, 1030, 1040, and 1060 can be described as "plug-type" occluder devices. The depicted occluder devices 970, 980, 990, 1010, 1020, 1030, 1040, and 1060 are generally cylindrical when in an unrestrained expanded or deployed configuration (as shown). In some embodiments, the occluder devices 970, 980, 990, 1010, 1020, 1030, and 1060 have shapes other than generally cylindrical such as, but not limited to, conical, frusto conical, spherical, pyramidal, truncated pyramidal, and the like.

In some embodiments, the occluder devices 970, 980, 990, 1010, 1020, 1030, 1040, and 1060 are constructed from material that is cut and then expanded. For example, in some embodiments the occluder devices 970, 980, 990, 1010, 1020, 1030, 1040, and 1060 are made from a tube or sheet of material that is laser-cut and then expanded (and heat-set in some embodiments) to the configuration substantially as shown. In some embodiments, NiTi is used as the material, but other materials such as stainless steel, L605 steel, polymers, and bioabsorbable polymers may also be used. In some embodiments, the constructions of the occluder devices 970, 980, 990, 1010, 1020, 1030, 1040, and 1060 can include hubs and wire elongate members as described elsewhere herein. In some embodiments, the occluder devices 970, 980, 990, 1010, 1020, 1030, 1040, and 1060 include a combination of types of frame constructs. For example, a portion of the frame of the occluder devices 970, 980, 990, 1010, 1020, 1030, 1040, and 1060 can be formed by cutting and expanding a material, and another portion of the frame can be made from one or more wires that may or may not be attached to a hub or hubs (wherein hubs include, but are not limited to, eyelets, rings, crimp collars, and the like). In some embodiments, frames of the occluder devices 970, 980, 990, 1010, 1020, 1030, 1040, and 1060 comprise one or more rows of cell structures. In some such embodiments, the cell structures can be of various shapes including, but not limited to, diamond-shaped, chevron-shaped, hexagonal, polygonal, and the like. In some embodiments, a single occlusive device can include a combination of shapes of cell structures (e.g., sizes and shapes). For example, a single occlusive device can include two or more shapes of cell structures (e.g., diamond-shaped, chevron-shaped, hexagonal, and the like).

In some embodiments, at least portions of the occluder devices 970, 980, 990, 1010, 1020, 1030, 1040, and 1060 include a covering that is configured to modulate, reduce, or inhibit the passage of blood and/or thrombus through the covering, i.e., to substantially occlude the flow of blood and/or thrombus through the covering. The covering(s) used with the occluder devices 970, 980, 990, 1010, 1020, 1030, 1040, and 1060 can include one or more of any feature, material, treatment, method of attachment to frame members, coverage of frame members, etc. as described elsewhere herein in regard to coverings such as, but not limited to, covering component 156, covering component 768, covering component 968, and all others. In some embodiments, the covering component is attached to the frame members so that the covering component is disposed on the inside of the occluder devices 970, 980, 990, 1010, 1020, 1030, 1040, and 1060. In some embodiments, the covering component is attached to the frame members so that the covering component is disposed on the outside of the occluder devices 970, 980, 990, 1010, 1020, 1030, 1040, and 1060. In some embodiments, the covering component is attached to the frame members so that the covering component is disposed on the inside and on the outside of the occluder devices 970, 980, 990, 1010, 1020, 1030, 1040, and 1060.

As described above, in some embodiments the covering component is configured to induce rapid tissue ingrowth. For example, pores of the covering component may be sized to provide a tissue ingrowth scaffold, while preventing formation of thrombi. The covering component can thereby provide supplemental occlusion device migration resistance and enhanced sealing. In some implementations, the covering component prevents or substantially prevents passage of blood, other bodily fluids, thrombi, emboli, or other bodily materials through the covering component. Some embodiments of the covering component comprises a fluoropolymer, such as an expanded polytetrafluoroethylene (ePTFE)

polymer. In some embodiments, the covering component can be a membranous covering. In some embodiments, the covering component can be a film. In some embodiments, the covering component can be a filtering medium. Any and all combinations and sub-combinations of such features (and other features) can be included in the occlusive devices provided herein, including in the occluder devices 970, 980, 990, 1010, 1020, 1030, 1040, and 1060.

Figure 51:
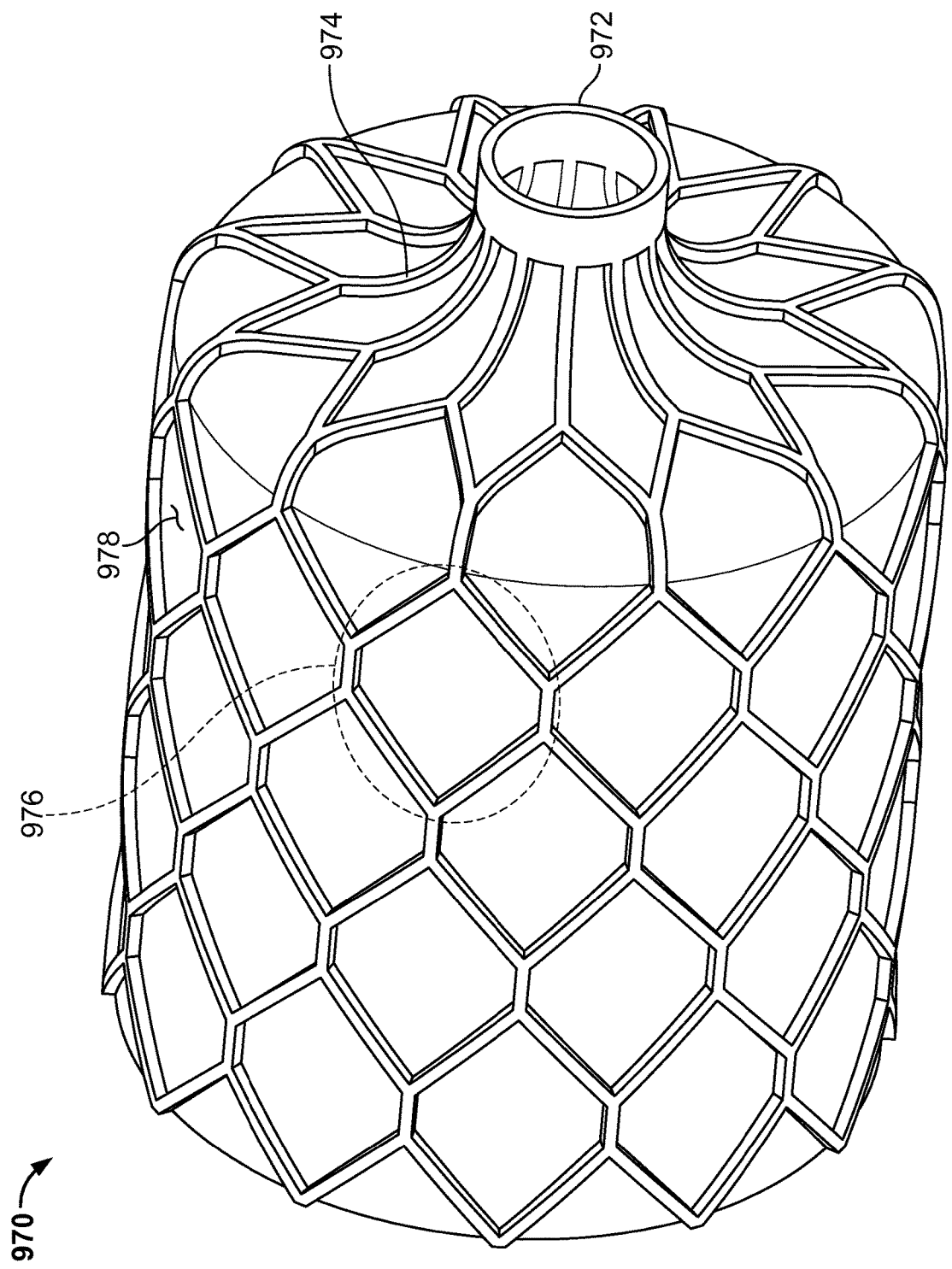
FIG. 51 is a perspective view of another example occlusive device in accordance with embodiments provided herein.

FIG. 51 illustrates a perspective view of an example occluder device 970. The depicted embodiment of occluder device 970 includes a hub 972, radial struts 974, a covering component 978, and cells 976. The radial struts 974 extend generally radially from the hub 972 to form an occlusive face of the occluder device 970. The radial struts 974 bifurcate to join with adjacent bifurcated radial struts 974 to form the cells 976. The depicted embodiment of occluder device 970 includes five rows of the cells 976 that are hexagonal cells. In some embodiments, fewer than five or more than five rows of cells 976 can be included in the occluder device 970; for example, the occluder device 970 may include one, two, three, four, five, six, seven, eight, or more than eight rows of cells 976. In the depicted embodiment, the occluder device 970 is radially symmetric. As such, the occluder device 970 is structurally balanced. Because of the structural balance of the occluder device 970, the occluder device 970 can have advantageous deployment reliability, durability, and conformability.

Figure 52:
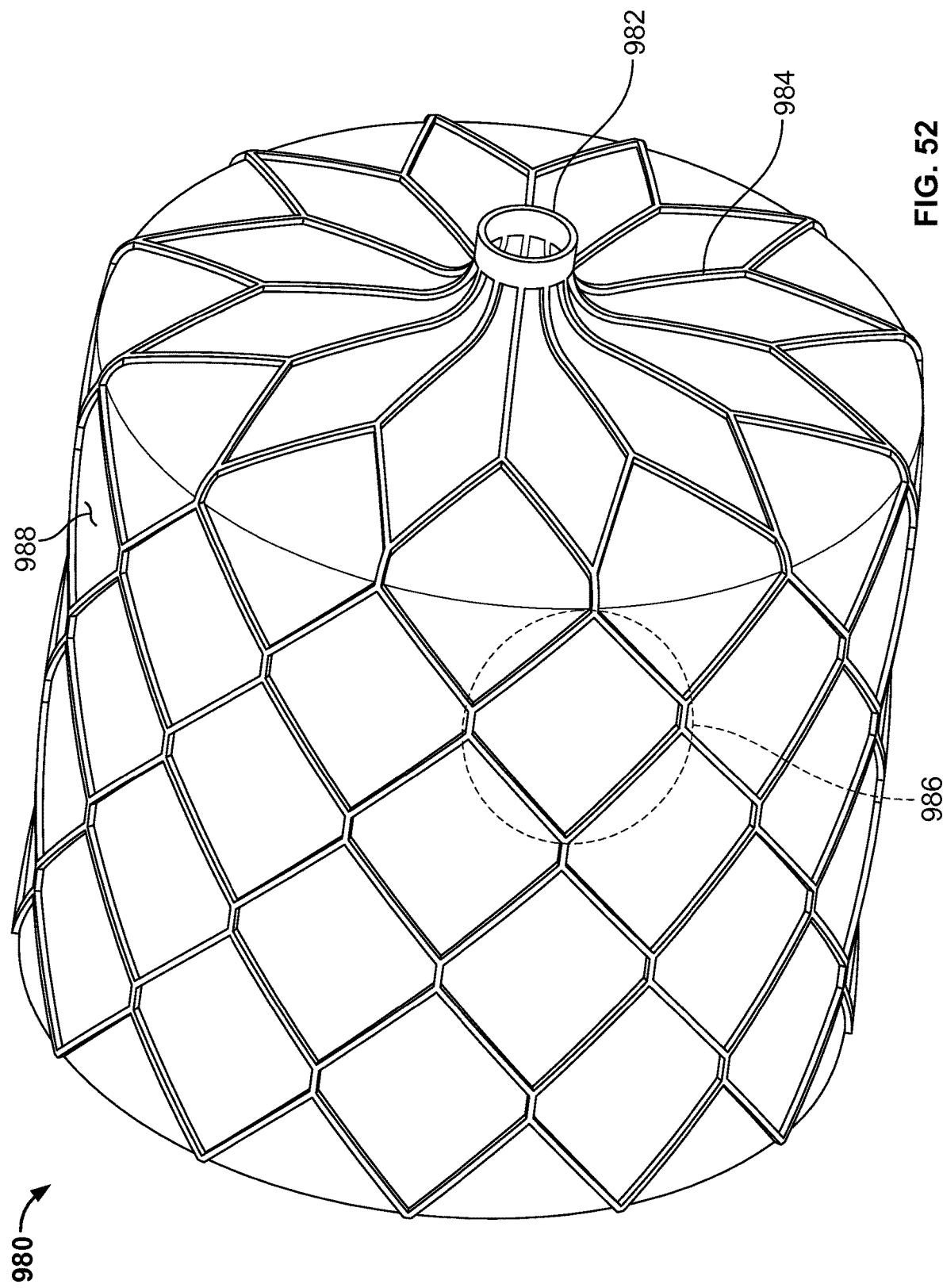
FIG. 52 is a perspective view of another example occlusive device in accordance with embodiments provided herein.

FIG. 52 illustrates a perspective view of an example occluder device 980. The depicted embodiment of occluder device 980 includes a hub 982, radial struts 984, a covering component 988, and cells 986. The radial struts 984 extend generally radially from the hub 982 to form an occlusive face of the occluder device 980. The radial struts 984 bifurcate to join with adjacent bifurcated radial struts 984 to form the cells 986. The depicted embodiment of occluder device 980 includes five rows of the cells 986 that are hexagonal cells. In some embodiments, fewer than five or more than five rows of cells 986 can be included in the occluder device 980; for example, the occluder device 980 may include one, two, three, four, five, six, seven, eight, or more than eight rows of cells 986.

While the constructions of occluder device 970 and occluder device 980 are similar, the depicted occluder device 970 is a smaller occluder device than the depicted occluder device 980. Therefore, it should be understood that the occlusive devices provided herein are scalable to a broad range of sizes so that the occlusive devices can be used in a variety of different anatomies, implant sites, and types of implementations.

Figure 53:
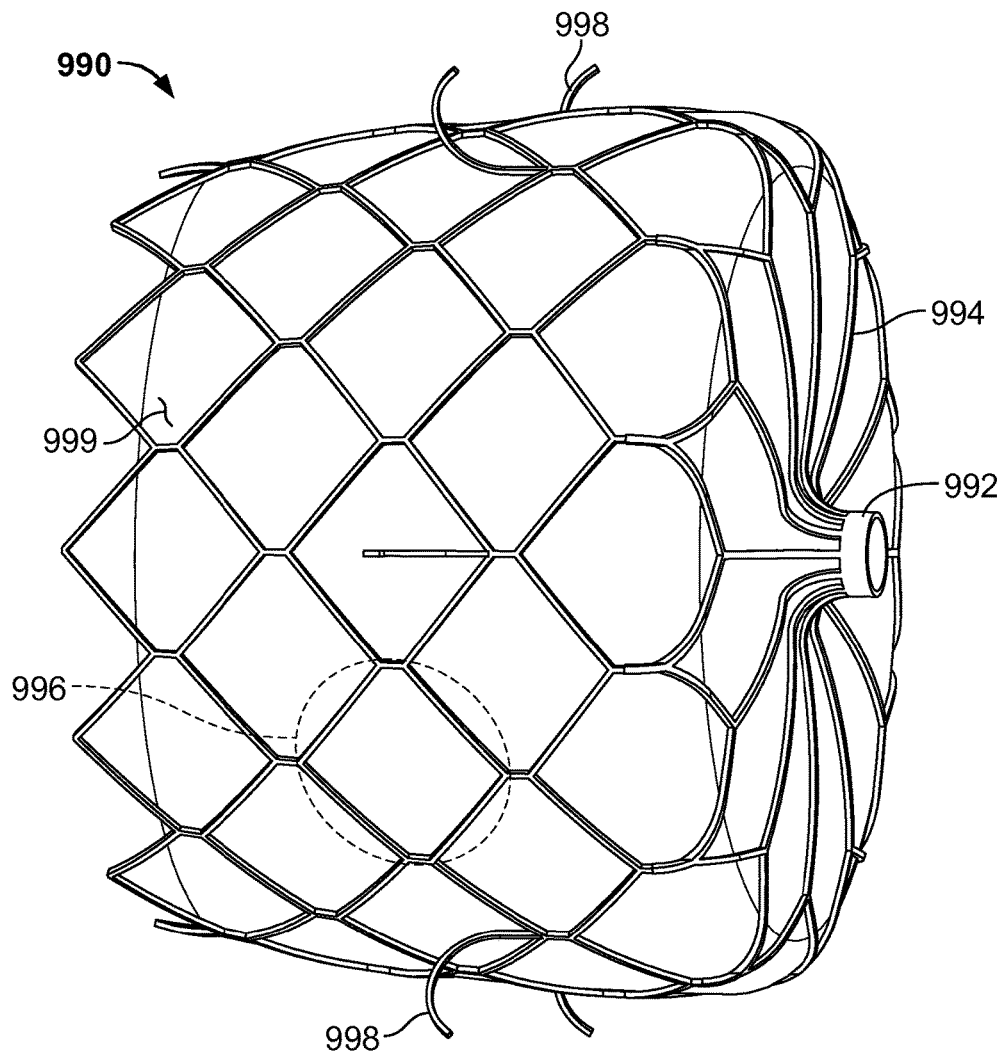
FIG. 53 is a perspective view of another example occlusive device in accordance with embodiments provided herein.

FIG. 53 illustrates a perspective view of an example occluder device 990. The depicted embodiment of occluder device 990 includes a hub 992, radial struts 994, cells 996, a covering component 999, and anchors 998. The radial struts 994 extend generally radially from the hub 992 to form an occlusive face of the occluder device 990. The radial struts 984 bifurcate to join with adjacent bifurcated radial struts 984 to form the cells 996. The depicted embodiment of occluder device 980 includes five rows of the cells 996 that are hexagonal cells. In some embodiments, fewer than five or more than five rows of cells 996 can be included in the occluder device 990; for example, the occluder device 990 may include one, two, three, four, five, six, seven, eight, or more than eight rows of cells 996.

In the depicted embodiment of occluder device 990, the anchors 998 extend within the interstitial spaces defined by particular cells 996 and extend radially outward from the cylindrical profile of the occluder device 990 to terminations at free ends of the anchors 998. As such, at least the tips of the anchors 998 can contact tissue and provide an anchoring function to resist migration of the occluder device 990 in relation to the tissue that the free ends of the anchors 998 is in contact with. While the depicted embodiment of occluder device 990 includes six anchors 998, in some embodiments one, two, three, four, five, seven, eight, nine, ten, eleven, twelve, or more than twelve anchors 998 are included. While the free ends of the anchors 998 of the depicted embodiment of occluder device 990 are terminations of elongate members that curve radially outward from the axis of the occlusive device 990, in some embodiments one or more of the anchors 998 include an atraumatic tip (e.g., refer to FIG. 16B). In some embodiments, one or more of the anchors 998 include a sharp tip (e.g., refer to FIG. 16C). In some embodiments, one or more of the anchors 998 include a bifurcated tip (e.g., refer to FIG. 16D). Such a bifurcated tip design may have individual tips that are sharpened, atraumatic ends (e.g., ball ends), or any of the other example anchor frame free ends described herein, or combinations thereof.

In some embodiments, the anchors 998 (and other anchors provided herein) are designed to be flexible and resilient such that the anchors 998 can be folded to a low-profile delivery configuration for containment within a delivery sheath, and can be translated within the delivery sheath without significant dragging resistance. When deployed from the delivery sheath, the anchors 998 revert to a curved configuration (e.g., as shown, or similar to as shown) that engages with the surrounding tissue at the deployment site. In some implementations, the anchors 998 pierce the surrounding tissue while the other parts of the frame 990 act as a pledget to limit the penetration depth of the anchors 998. In addition, in some embodiments the covering component can provide a seal around the penetration site. In such ways, the risk of pericardial effusion related to penetration of the anchors 998 can be mitigated. In some implementations, the anchors 998 engage the surrounding tissue without penetration.

Figure 55:
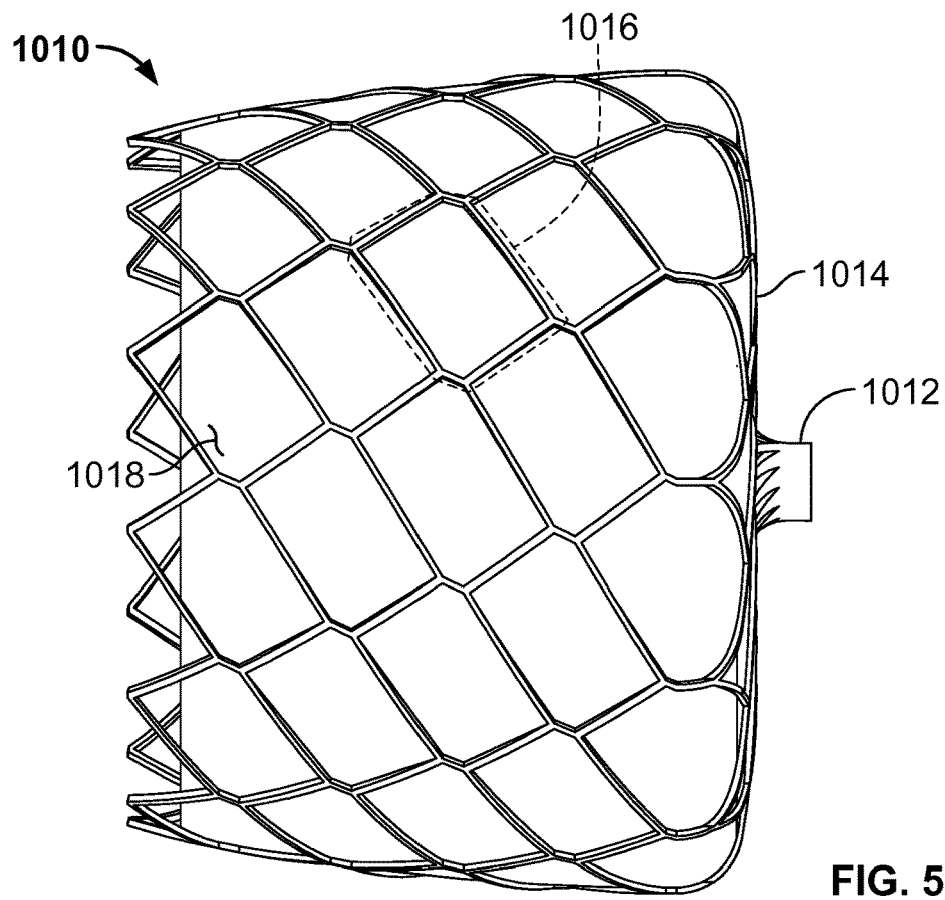
FIG. 55 is a side view of another example occlusive device in accordance with embodiments provided herein.
Figure 56:
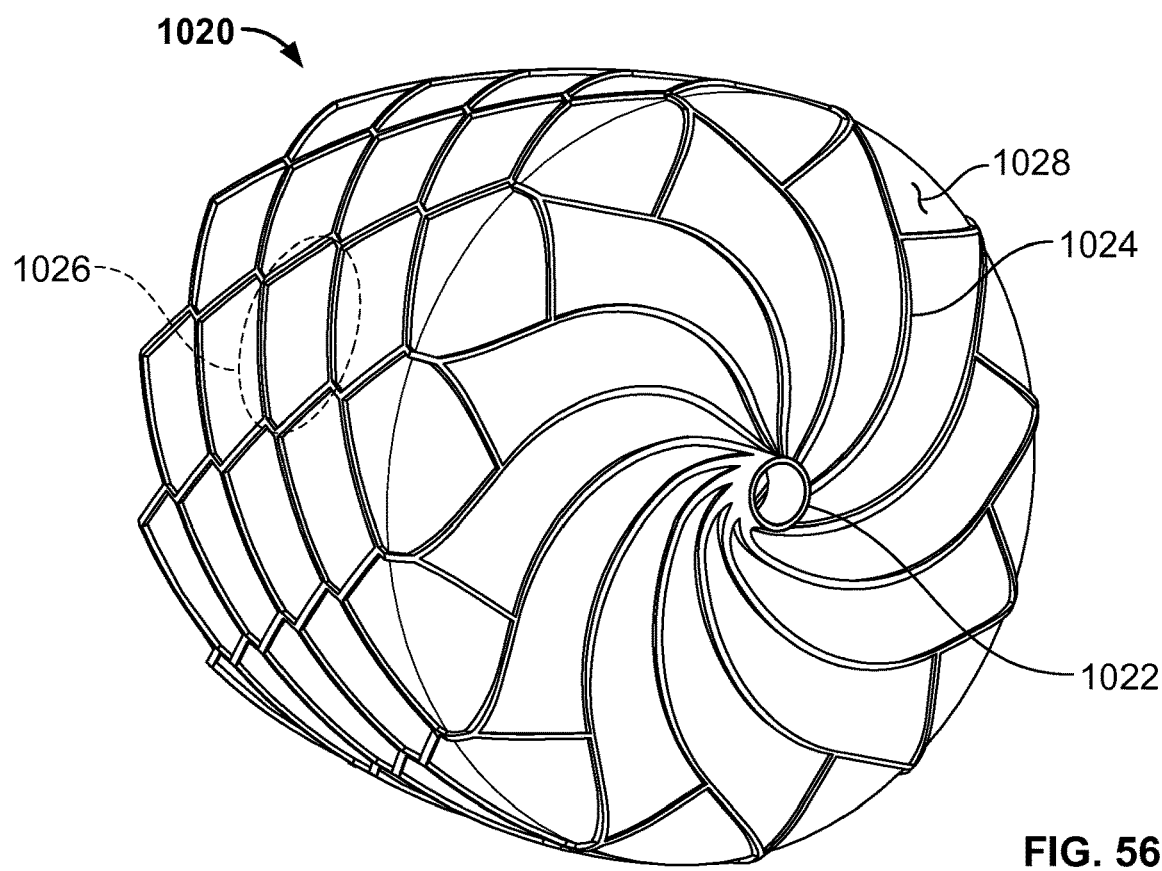
FIG. 56 is a perspective view of another example occlusive device in accordance with embodiments provided herein.

FIG. 55 illustrates a perspective view of an example occluder device 1010. The depicted embodiment of occluder device 1010 includes a hub 1012, radial struts 1014, a covering component 1018, and hexagonal cells with a helical bias 1016. The radial struts 1014 extend generally radially from the hub 1012 to form an occlusive face of the occluder device 1010. The radial struts 1014 bifurcate to join with adjacent bifurcated radial struts 1014 to form the hexagonal cells with a helical bias 1016. The depicted embodiment of occluder device 1010 includes five rows of the hexagonal cells with a helical bias 1016. In some embodiments, fewer than five or more than five rows of hexagonal cells with a helical bias 1016 can be included in the occluder device 1010; for example, the occluder device 1010 may include one, two, three, four, five, six, seven, eight, or more than eight rows of hexagonal cells with a helical bias 1016. FIG. 56 illustrates a perspective view of an example occluder device 1020. The depicted embodiment of occluder device 1020 includes a hub 1022, curved struts 1024, a covering component 1028, and hexagonal cells with a helical bias 1026. The curved struts 1024 extend along a curved path from the hub 1022 to form an occlusive face of the occluder device 1020. The curved struts 1024 bifurcate to join with adjacent bifurcated curved struts 1024 to form the hexagonal cells with a helical bias 1026. The depicted embodiment of occluder device 1020 includes five rows of the hexagonal cells with a helical bias 1026. In some embodiments, fewer than five or more than five rows of hexagonal cells with a helical bias 1026 can be included in the occluder device 1020; for example, the occluder device 1020 may include one, two, three, four, five, six, seven, eight, or more than eight rows of hexagonal cells with a helical bias 1026.

The occlusive devices 1010 and 1020 can have advantageous properties owing to the curved struts 1024 and cells with helical bias 1016 and 1026. Such advantageous properties can include, but are not limited to, enhanced conformability (at the occlusive face and along the sides of the devices 1010 and 1020), enhanced sealing capabilities, enhanced durability and fatigue resistance, and a low delivery profile.

Figure 54:
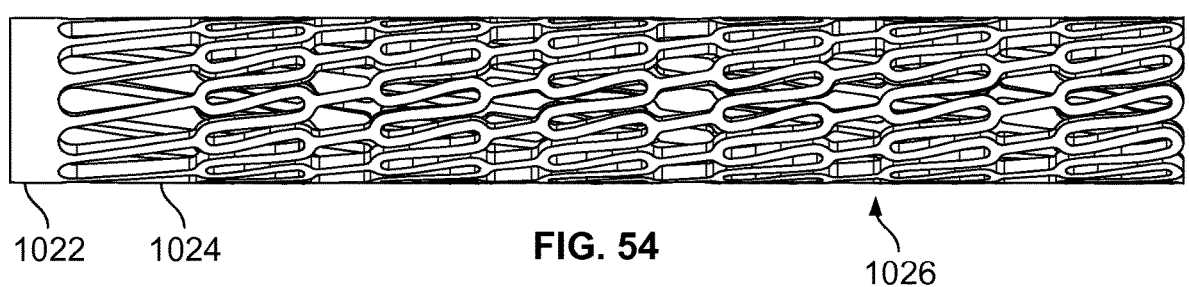
FIG. 54 is a cutting pattern that can be used to cut a tube (or a portion of a tube) to create the frame of the occlusive device of FIG. 56.

FIG. 54 illustrates a material cutting pattern 1028 that can be used to form the occlusion device 1020. The portions of the cutting pattern 1028 that will form the hub 1022, the curved struts 1024, and the hexagonal cells with a helical bias 1026 are identified. Using pattern 1028, the frame of the occluder device 1020 can be formed as a unitary member. In some cases, the material cutting pattern 1028 can be utilized for laser-cutting a tube of material. In some such cases, the frame of the occluder device 1020 is a unitary and seamless construct. Or, in some cases a planar sheet of material can be cut as shown and the sheet can thereafter be formed into a tube. In some embodiments, chemical etching, machining, water jet cutting, or other techniques can be used to create the frame of the occluder device 1020 in accordance with the material cutting pattern 1028.

Figure 57:
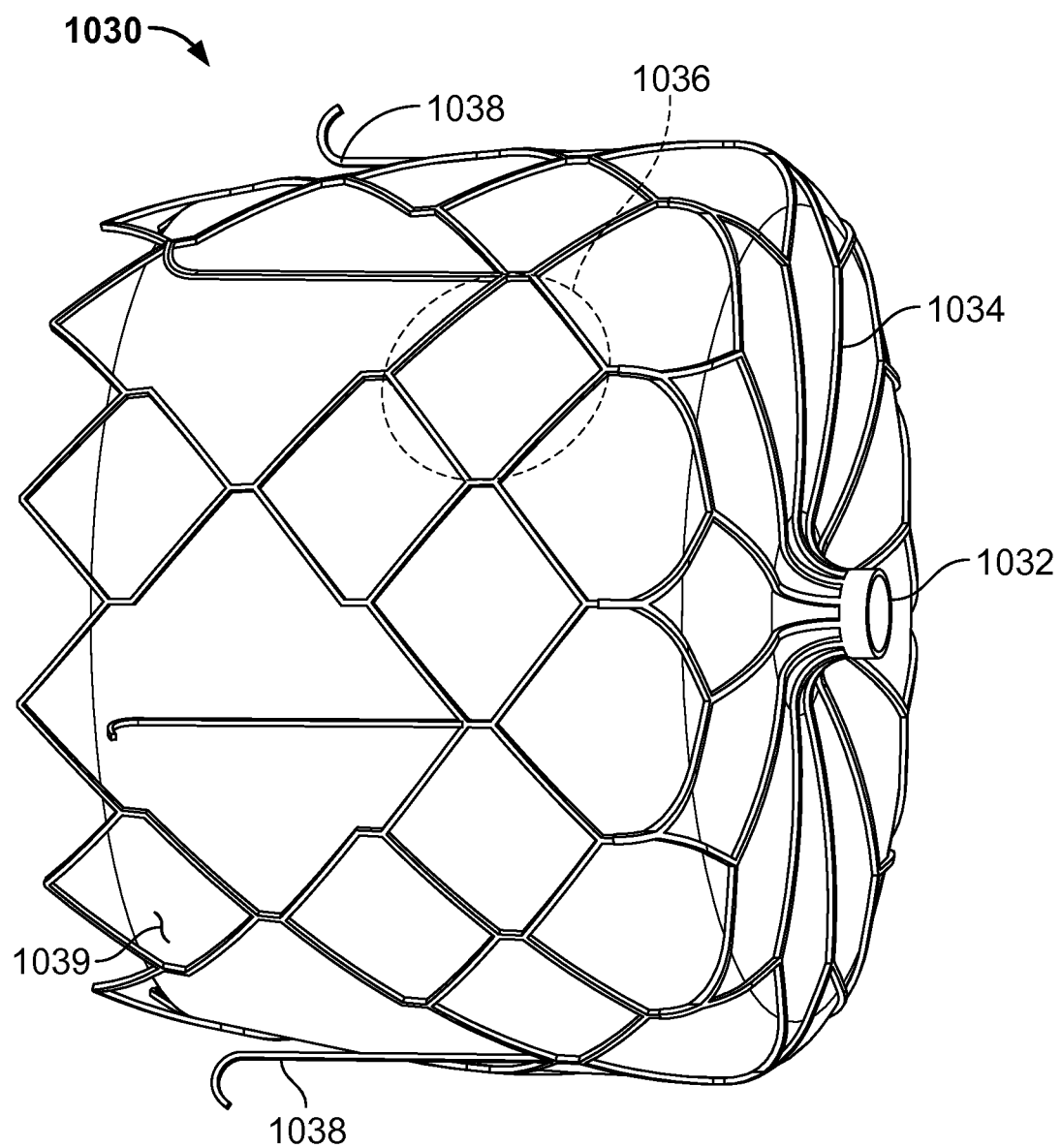
FIG. 57 is a perspective view of another example occlusive device in accordance with embodiments provided herein.

FIG. 57 illustrates a perspective view of an example occluder device 1030. The depicted embodiment of occluder device 1030 includes a hub 1032, radial struts 1034, cells 1036, a covering component 1039, and anchors 1038. The radial struts 1034 extend generally radially from the hub 1032 to form an occlusive face of the occluder device 1030. The radial struts 1034 bifurcate to join with adjacent bifurcated radial struts 1034 to form the cells 1036. The depicted embodiment of occluder device 1030 includes four rows of the cells 1036 that are hexagonal. In some embodiments, fewer than four or more than four rows of cells 1036 can be included in the occluder device 1030; for example, the occluder device 1030 may include one, two, three, four, five, six, seven, eight, or more than eight rows of cells 1036.

In the depicted embodiment of occluder device 1030, the anchors 1038 extend within the interstitial spaces defined between particular groups of cells 1036, and extend radially outward from the cylindrical profile of the occluder device 1030 to terminations at free ends of the anchors 1038. In comparison to the occluder device 990 that has anchors 998 (refer to FIG. 53), the anchors 1038 can be made longer than the anchors 998. That is the case because the length of the anchors 998 are limited to the size of open space of individual cells 996. In contrast, the occluder device 1030 is configured to include larger open spaces between the particular groups of cells 1036 in which the anchors 1038 are located. Therefore, in some embodiments the anchors 1038 can be made longer than the anchors 998.

At least the tips of the anchors 1038 can contact tissue and provide an anchoring function to resist migration of the occluder device 1030 in relation to the tissue that the free ends of the anchors 1038 is in contact with. While the depicted embodiment of occluder device 1030 includes six anchors 1038, in some embodiments one, two, three, four, five, seven, eight, nine, ten, eleven, twelve, or more than twelve anchors 1038 are included. While the free ends of the anchors 1038 of the depicted embodiment of occluder device 1030 are terminations of elongate members that curve radially outward from the axis of the occlusive device 1030, in some embodiments one or more of the anchors 1038 include an atraumatic tip (e.g., refer to FIG. 16B). In some embodiments, one or more of the anchors 1038 include a sharp tip (e.g., refer to FIG. 16C). In some embodiments, one or more of the anchors 1038 include a bifurcated tip (e.g., refer to FIG. 16D). Such a bifurcated tip design may have individual tips that are sharpened, atraumatic ends (e.g., ball ends), or any of the other example anchor frame free ends described herein, or combinations thereof.

In some embodiments, the anchors 1038 (and other anchors provided herein) are designed to be flexible and resilient such that the anchors 1038 can be folded to a low-profile delivery configuration for containment within a delivery sheath, and can be translated within the delivery sheath without significant dragging resistance. When deployed from the delivery sheath, the anchors 1038 revert to a curved configuration (e.g., as shown, or similar to as shown) that engages with the surrounding tissue at the deployment site. In some implementations, the anchors 1038 pierce the surrounding tissue while the other parts of the frame 1030 act as a pledget to limit the penetration depth of the anchors 1038. In addition, in some embodiments the covering component can provide a seal around the penetration site. In such ways, the risk of pericardial effusion related to penetration of the anchors 1038 can be mitigated. In some implementations, the anchors 1038 engage the surrounding tissue without penetration.

Figure 58:
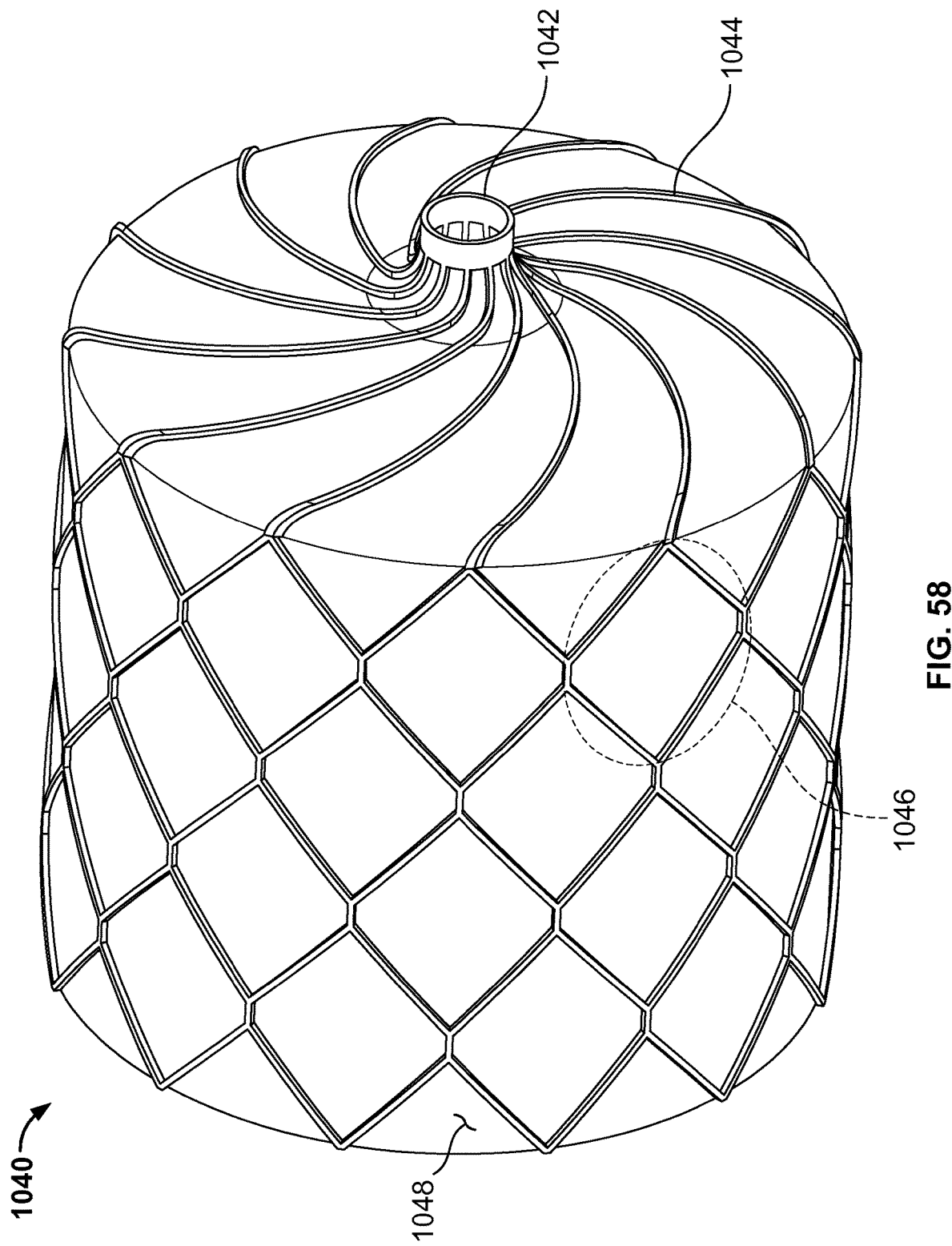
FIG. 58 is a perspective view of another example occlusive device in accordance with embodiments provided herein.

FIG. 58 illustrates a perspective view of an example occluder device 1040. The depicted embodiment of occluder device 1040 includes a hub 1042, curved struts 1044, a covering component 1048, and cells 1046. The curved struts 1044 extend along a curved path from the hub 1042 to form an occlusive face of the occluder device 1040. The curved struts 1044 bifurcate to join with adjacent bifurcated curved struts 1044 to form the cells 1046. The depicted embodiment of occluder device 1040 includes four rows of the cells 1046 that are hexagonal. In some embodiments, fewer than four or more than four rows of cells 1046 can be included in the occluder device 1040; for example, the occluder device 1040 may include one, two, three, four, five, six, seven, eight, or more than eight rows of cells 1046.

The occlusive device 1040 can have advantageous properties owing to the curved struts 1044. Such advantageous properties can include, but are not limited to, enhanced conformability (e.g., at the occlusive face of the device 1040), enhanced sealing capabilities, enhanced durability and fatigue resistance, and a low delivery profile.

Figure 59:
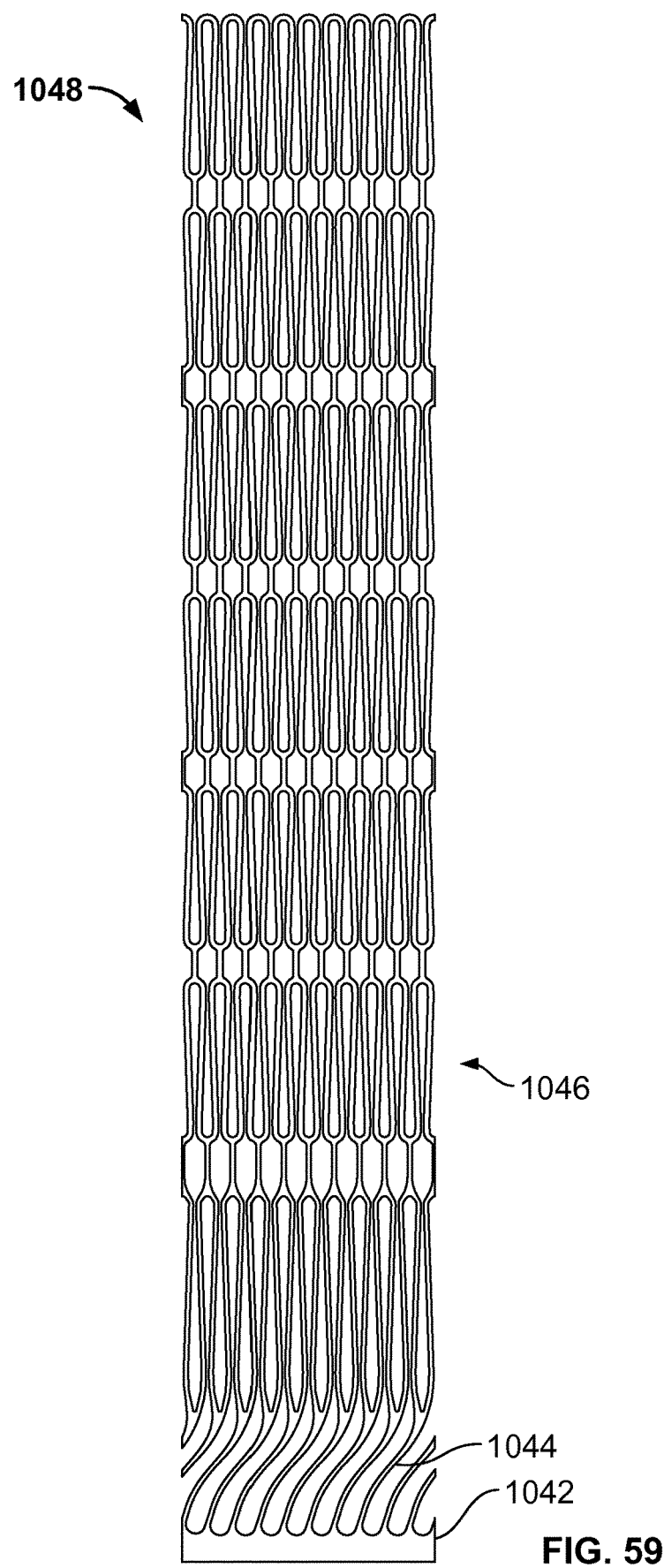
FIG. 59 is a cutting pattern that can be used to cut a tube (or a planar sheet of material) to create the frame of the occlusive device of FIG. 58.

FIG. 59 illustrates a material cutting pattern 1048 that can be used to form the occlusion device 1040. The portions of the cutting pattern 1048 that will form the hub 1042, the curved struts 1044, and the hexagonal cells 1046 are identified. Using pattern 1048, the frame of the occluder device 1040 can be formed as a unitary member. In some cases, the material cutting pattern 1048 can be utilized for laser-cutting a tube of material. In some such cases, the frame of the occluder device 1020 is a unitary and seamless construct. Or, in some cases a planar sheet of material can be cut as shown and the sheet can thereafter be formed into a tube. In some embodiments, chemical etching, machining, water jet cutting, or other techniques can be used to create the frame of the occluder device 1040 in accordance with the material cutting pattern 1048.

Figure 60:
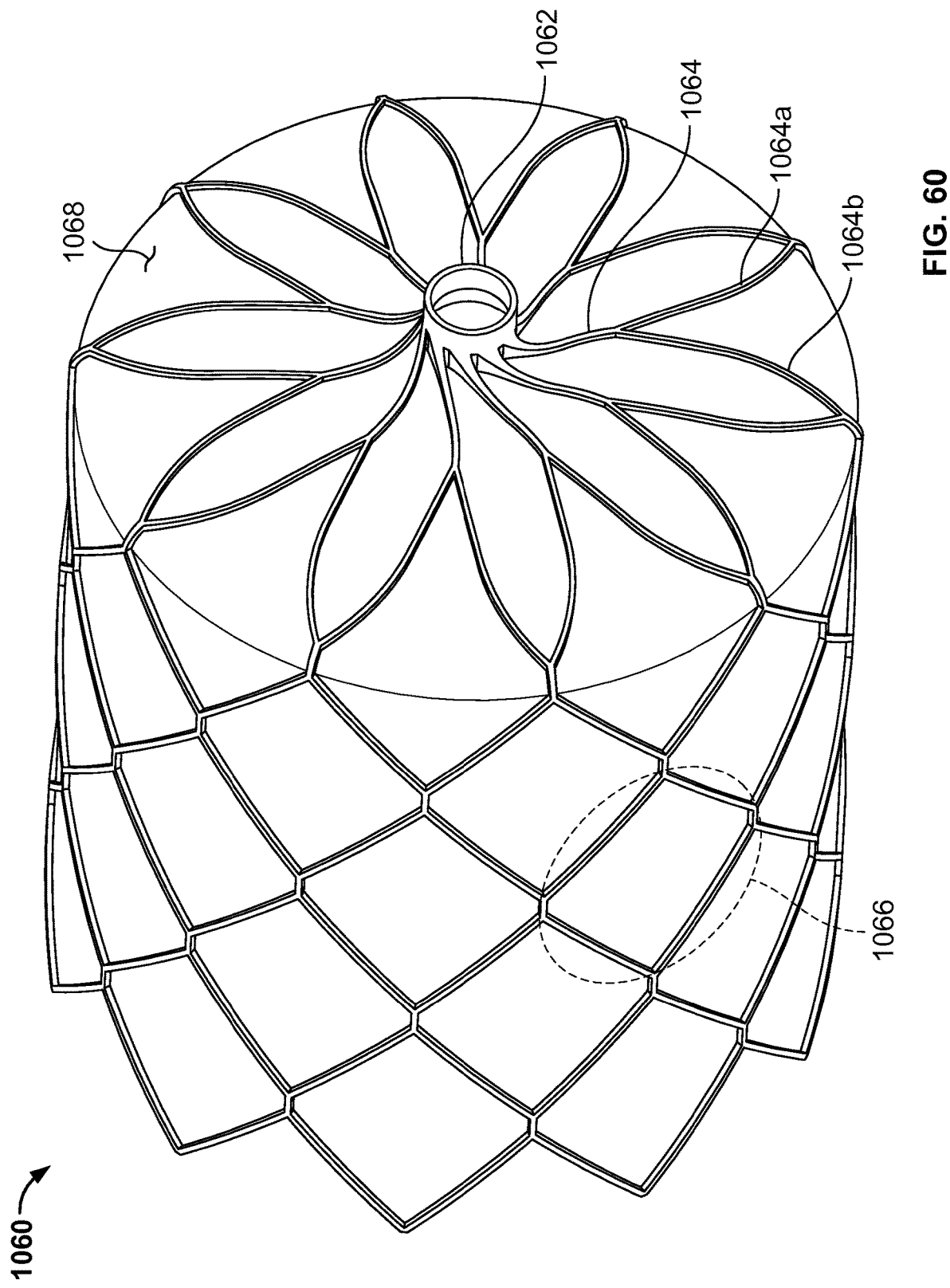
FIG. 60 is a perspective view of another example occlusive device in accordance with embodiments provided herein.

FIG. 60 illustrates a perspective view of an example occluder device 1060. The depicted embodiment of occluder device 1060 includes a hub 1062, radial struts 1064, a covering component 1068, and cells 1066. The radial struts 1064 extend generally radially from the hub 1062 and then bifurcate into a first radial strut portion 1064a and a second radial strut portion 1064b. The radial struts 1064 in combination with the first radial strut portion 1064a and the second radial strut portion 1064b form an occlusive face of the occluder device 1060. The first radial strut portion 1064a joins with an adjacent second radial strut portion 1064b such that the cells 1066 can be defined. The depicted embodiment of occluder device 1060 includes five rows of the cells 1066 that are hexagonal. In some embodiments, fewer than five or more than five rows of cells 1066 can be included in the occluder device 1060; for example, the occluder device 1060 may include one, two, three, four, five, six, seven, eight, or more than eight rows of cells 1066.

The occluder device 1060 can have advantageous properties owing to the design of the radial struts 1064. The design of the radial struts 1064 combines some features of the radially symmetrical designs (e.g., FIGS. 51 and 52) with their advantageous deployment reliability, durability, and conformability, along with the curved strut designs (e.g., FIGS. 56 and 58) with their advantageous conformability, sealing capabilities, durability and fatigue resistance, and low delivery profile.

Figure 61:
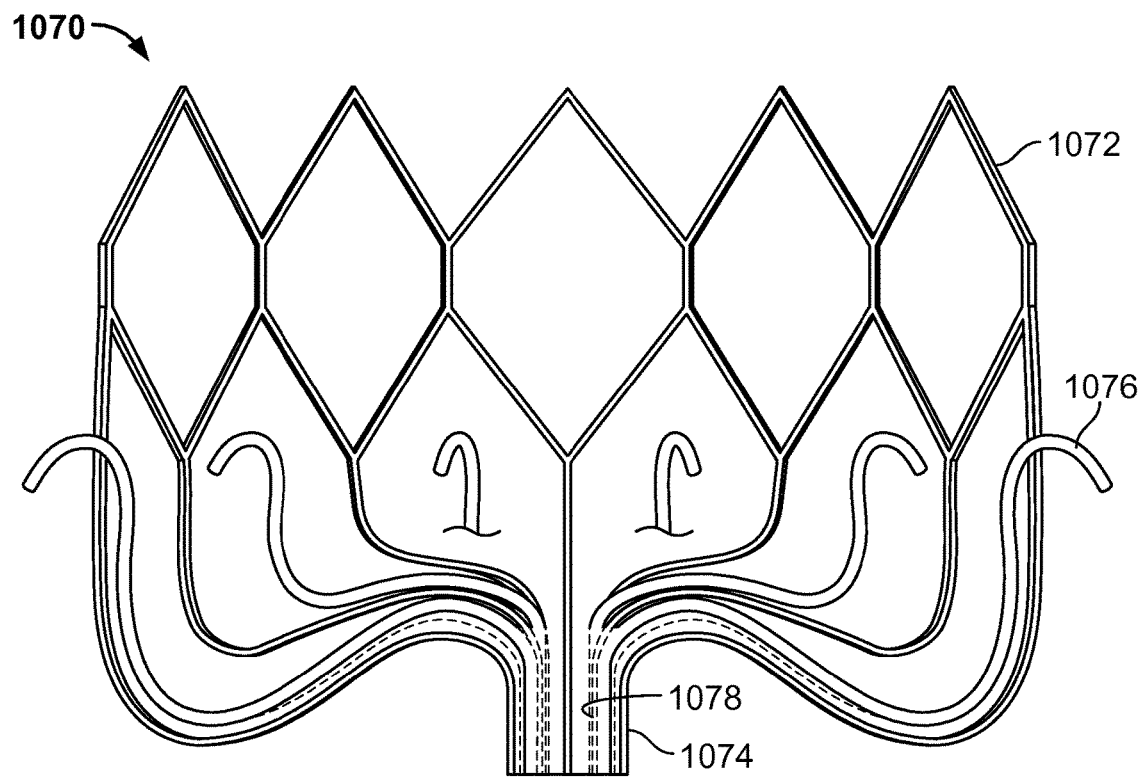
FIG. 61 is a schematic illustration of another example occlusive device in accordance with embodiments provided herein.

FIG. 61 schematically depicts an occluder device 1070 including an occlusion frame 1072 and an anchor frame 1076. The occlusion frame 1072 includes a hub 1074, and the anchor frame 1076 includes a hub 1078. The occlusion frame 1072 can comprise one or more rows of cells in some embodiments; for example, the occlusion frame 1072 may include one, two, three, four, five, six, seven, eight, or more than eight rows of cells.

FIG. 61 is drawn to highlight particular frame features that can be incorporated into the designs of the occlusive devices provided herein. For example, the designs of the hubs 1074 and 1076 and/or other frame features are highlighted. It should be understood that one or more of the features that are highlighted in this figure can be included in any of the occlusive devices described elsewhere herein, and that such features (and other features described herein) can be mixed and matched to create hybrid designs that are entirely within the scope of this disclosure. In this figure, no covering component is shown and some portions of the frames are not shown so that the highlighted frame features are more readily visible. It should be understood that the occlusive device of FIG. 61 can be combined with a covering component in some embodiments. The covering component can share any or all of the features, characteristics, properties, etc. as described above in reference to the covering component 156 and/or any other exemplary covering components described herein.

In the depicted embodiment of occluder device 1070, the occlusion frame 1072 and the anchor frame 1076 are both individually formed by cutting material (e.g., laser cutting tubular materials (e.g., NiTi) or planar materials). The hub 1074 of the formed occlusion frame 1072 and the hub 1078 of the formed anchor frame 1076 are then coupled together in a nested arrangement. The hubs 1074 and 1078 can be coupled by being press-fit together, welded together, adhered together, mechanically interlocking, and the like, and combinations thereof.

The occluder device 1070 can provide advantageous features owing to the construction of the device 1070. For example, because the occlusion frame 1072 and the anchor frame 1076 are only coupled at their hubs 1074 and 1078 in the depicted embodiment, substantial independence of movement between the occlusion frame 1072 and the anchor frame 1076 is facilitated. In addition, the occlusion frame 1072 and the anchor frame 1076 can be formed from differing materials, differing elongate element sizes, and so on, so that the properties of the occlusion frame 1072 and the anchor frame 1076 can be independently selected as desired. For example, in some embodiments the anchor frame 1076 can be a bioabsorbable polymer while the occlusion frame 1072 is NiTi. Any and all such above-described variations, combinations, permutations, and sub-combinations of: materials, components, constructions, features, and configurations of the occlusion frame 1072 and the anchor frame 1076 are envisioned within the scope of this disclosure.

In the depicted embodiment of occluder device 1070, the anchor frame 1076 is within the occlusion frame 1072, except that the free ends of the anchor frame 1076 extend beyond the outer lateral profile of the occlusion frame 1072. In some embodiments, the occlusion frame 1072 is within the anchor frame 1076 such that the hub 1074 within the hub 1078.

Figure 62A:
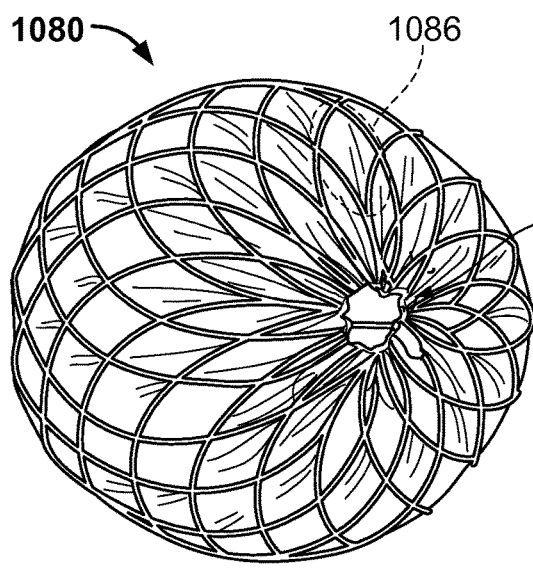
FIG. 62A is a perspective view of another example occlusive device in accordance with embodiments provided herein.
Figure 62B:
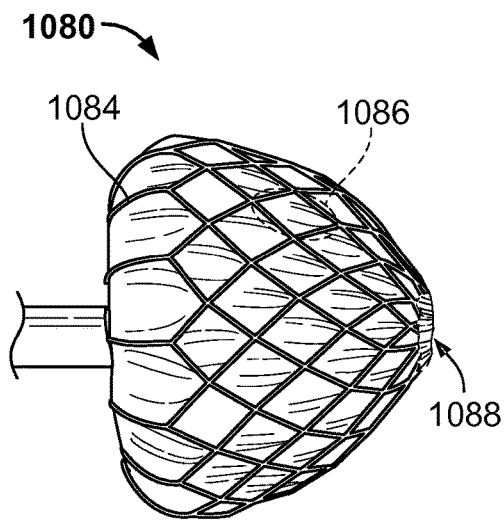
FIG. 62B is a side view of the example occlusive device of FIG. 62A.

FIGS. 62A and 62B illustrate another example occluder device 1080. The frame of the occluder device 1080 can be constructed, for example, like any of the occluder devices 970, 980, 990, 1010, 1020, 1030, 1040, and 1060 described above. For example, the occluder device 1080 includes a hub (not shown), radial struts 1084, and multiple rows of diamond-shaped cells 1086 (and may also include anchors, etc.). However, the occluder device 1080 is distinct from the depicted embodiments of the occluder devices 970, 980, 990, 1010, 1020, 1030, 1040, and 1060 in that the distal end of the occluder device 1080 is gathered to form an apex 1088. The gathering of the frame to form the apex 1088 can be accomplished, for example, by weaving a gathering member (e.g., a suture or wire) through the apices of the distal-most row of diamond-shaped cells 1086, and fixing the gathering member such that the distal-most row of diamond-shaped cells 1086 are gathered together to a desired extent. In some embodiments, in some embodiments the same shape is attained by heat-setting rather than gathering. The advantage is that the frame will endure less strain than the gathering (more fatigue resistant).

The gathering of the frame of occluder device 1080 to form the apex 1088 has the effect of reshaping the occluder device 1080 to create a tapered outer profile and more a rounded proximal end. In result, the following advantages may potentially be realized: 1) tucking apical points into a condensed blunt and flattened distal end may make the distal end of the occluder device 1080 more atraumatic; 2) the distal end of occluder device 1080 is made stiffer (potentially helping to improve anchor retention with greater radial force); 3) the gathered distal end creates structure that helps organize and radially balance the frame for enhanced deployment reliability, because the frame is allowed to compress more evenly without allowing the frame to flare or pleat—thereby helping with catheter loading, deployment, and repositioning; 4) the shape may conform better with a LAA. In some embodiments, the gathered distal end can be replaced or enhanced by the addition of a film disc (to provide further coverage of the distal end) and/or an internal solid hub component (to improve alignment of all distal apices).

In general, for any of the designs described as being laser-cut from a tube, the designs may similarly be cut from a planar sheet of material, and the sheet may thereafter be formed into a tube.

In addition to the materials previously discussed wires for the frames or tubes for the frames can be made from a variety of suitable materials. For example, the wires or tubes can be made of nitinol (NiTi), L605 steel, MP35N steel, stainless steel, a polymeric material, Pyhnox, Elgiloy, or any other appropriate biocompatible material.

In general, the frames for any of the devices described herein may be constructed from one or more elongate members. For frames or sub-frames comprising wires, the frames or sub-frames may be constructed using a modular tool, in some examples, or by using a jig apparatus in other examples.

While the occlusion devices have been described with respect to an LAA, in some embodiments, the occlusion devices can be used to occlude or seal other apertures within a body of a patient, such as a right atrial appendage, a fistula, a patent ductus arteriousus, an atrial septal defect, a ventricular septal defect, a paravalvular leak, an arteriovenous malformation, or a body vessel.

The examples discussed herein have focused on occlusion devices, but it is contemplated that the features described herein may also be used with other types of medical devices or accessories. Examples of implantable devices and accessories include, without limitation, occlusion and closure devices, filters (e.g. inferior vena cava filter or an embolic protection filter), catheter based grabbers or retrieval devices, temporary filtration devices, stents, stent-grafts, and vessel sizers. For embodiments where the device is designed to filter, the covering component may be porous, where the pores are sized to generally permit blood to pass through the pores, but are sized to prevent emboli or thrombi from passing through the pores of the covering component.

For additional examples of hub features that can be used with the devices discussed herein, see the provisional application titled "Joint Assembly for Medical Devices," having inventors Coby C. Larsen, Steven J. Masters, and Thomas R. McDaniel, filed on 16 Nov. 2012, and which is herein incorporated by reference in its entirety for all purposes, and see also the provisional application titled "Space Filling Devices," having inventors Coby C. Larsen, Brandon A. Lurie, Steven J. Masters, Thomas R. McDaniel, and Stanislaw L. Zukowski, filed on 15 Mar. 2013, and which is herein incorporated by reference in its entirety for all purposes. For additional examples of delivery system devices, systems, and techniques that can be used to deliver, deploy, reposition, and retrieve the devices discussed herein, see the provisional application titled "Implantable Medical Device Deployment System," having inventors Steven J. Masters and Thomas R. McDaniel, filed on 16 Nov. 2012, and which is herein incorporated by reference in its entirety for all purposes.

Several characteristics and advantages have been set forth in the preceding description, including various alternatives together with details of the structure and function of the devices and/or methods. The disclosure is intended as illustrative only and as such is not intended to be exhaustive. It will be evident to those skilled in the art that various modifications may be made, especially in matters of structure, materials, elements, components, shapes, sizes, and arrangements of parts including combinations within the principles described herein, to the full extent indicated by the broad, general meaning of the terms in which the appended claims are expressed. To the extent that these various modifications depart from the spirit and scope of the appended claims, they are intended to be encompassed therein. All references, publications, and patents referred to herein, including the figures and drawings included therewith, are incorporated by reference in their entirety.

What is claimed is:

1. An occlusive device comprising:
 a unitary frame having a tapered outer profile configured to conform to an appendage of a patient, the frame including:
  a hub;
  a plurality of curved radial struts extending radially outward from the hub and defining an occlusive face of the frame;
  a plurality of cells extending from the plurality of curved radial struts in a distal direction, wherein the plurality of cells are arranged in interconnected rows of cells to define a lateral outer surface of the frame;
  a gathered distal end including a blunt apex formed by apical points of the struts joined together at the apical points to form the gathered distal end,
   wherein the struts are fixed to one another at a distal-most row of the plurality of cells at a distal end of the occlusive device to thereby define the gathered distal end,
   wherein the gathered distal end is configured to radially balance the frame and enhance deployment reliability, and
   wherein the plurality of curved radial struts include a constant curvature along the lateral outer surface of the frame extending from the occlusive face of the frame to the gathered distal end; and
 a covering component attached to the frame such that at least a portion of the covering component modulates passage of blood or thrombus through at least a portion of the occlusive device.

2. The occlusive device of claim 1, wherein the frame further comprises a plurality of anchor elements that extend radially outward from the lateral outer surface of the frame.

3. The occlusive device of claim 2, wherein the plurality of anchor elements are at least partially positioned in interstitial spaces defined by at least some cells of the plurality cells.

4. The occlusive device of claim 1, wherein the frame is formed from a single tubular piece of precursor material.

5. The occlusive device of claim 1, wherein at least some of the cells are helically biased hexagonal cells that comprise rectangular shapes.

6. The occlusive device of claim 1, further comprising a gathering member, wherein the gathering member is interwoven through apices of an end-most row of cells.

7. The occlusive device of claim 6, wherein the gathering member is in tension such that each cell of the end-most row of cells is made to be positioned nearer to the other cells of the end-most row of cells than without the tension.

8. The occlusive device of claim 1, wherein at least some of the cells comprise a diamond shape or a hexagon shape.

9. An occlusive device comprising:
 a unitary frame having a tapered outer profile configured to conform to an appendage of a patient, the frame including:
  a hub;
  a plurality of curved radial struts extending radially outward from the hub and defining an occlusive face of the frame; and
  a plurality of cells extending from the plurality of curved radial struts in a distal direction, wherein the plurality of cells are arranged in interconnected rows of cells to define a lateral outer surface of the frame including a constant curvature along the lateral outer surface of the frame extending from the occlusive face of the frame to a distal end of the frame;
 a covering component attached to the frame such that at least a portion of the covering component modulates passage of blood or thrombus through at least a portion of the occlusive device; and a gathering member, wherein the gathering member is interwoven through apices of an end-most row of cells so as to fix the apices together at a distal end of the occlusive device to form a gathered distal end including a blunt apex, wherein the gathered distal end is configured to radially balance the frame and enhance deployment reliability.

10. The occlusive device of claim 9, wherein the gathering member is in tension such that each cell of the end-most row of cells is made to be positioned nearer to the other cells of the end-most row of cells than without the tension.

11. The occlusive device of claim 9, wherein the frame further comprises a plurality of anchor elements that extend radially outward from the lateral outer surface of the frame.

12. The occlusive device of claim 11, wherein the plurality of anchor elements are at least partially positioned in interstitial spaces defined by at least some cells of the plurality of cells.

13. The occlusive device of claim 9, wherein at least some of the cells comprise hexagon shapes.

14. The occlusive device of claim 13, wherein the hexagon shaped cells are helically biased and comprise rectangular shapes.

* * * * *